(12) United States Patent
Casteel et al.

(10) Patent No.: US 9,382,256 B2
(45) Date of Patent: *Jul. 5, 2016

(54) FORMULATION OF SYK INHIBITORS

(71) Applicant: Gilead Connecticut, Inc., Foster City, CA (US)

(72) Inventors: Melissa Jean Casteel, Hayward, CA (US); Bei Li, Foster City, CA (US); Rowchanak Pakdaman, San Carlos, CA (US); Diana Sperger, Belmont, CA (US); Dimitrios Stefanidis, Mountain View, CA (US)

(73) Assignee: Gilead Connecticut, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/445,970

(22) Filed: Jul. 29, 2014

(65) Prior Publication Data
US 2015/0038504 A1    Feb. 5, 2015

Related U.S. Application Data

(60) Provisional application No. 61/860,198, filed on Jul. 30, 2013.

(51) Int. Cl.
*A61K 31/495* (2006.01)
*C07D 487/04* (2006.01)
*A61K 9/20* (2006.01)
*C07C 309/66* (2006.01)
*A61K 31/5377* (2006.01)
*A61K 9/28* (2006.01)

(52) U.S. Cl.
CPC ............ *C07D 487/04* (2013.01); *A61K 9/2027* (2013.01); *A61K 9/2095* (2013.01); *A61K 31/5377* (2013.01); *C07C 309/66* (2013.01); *A61K 9/2866* (2013.01)

(58) Field of Classification Search
USPC ....................................................... 544/117
See application file for complete search history.

(56) References Cited

U.S. PATENT DOCUMENTS

| 5,593,997 | A | 1/1997 | Dow et al. |
| 5,658,857 | A | 8/1997 | Andree et al. |
| 5,783,576 | A | 7/1998 | Roos et al. |
| 5,846,514 | A | 12/1998 | Foster et al. |
| 6,334,997 | B1 | 1/2002 | Foster et al. |
| 6,919,340 | B2 | 7/2005 | Currie et al. |
| 6,919,341 | B2 | 7/2005 | Paruch et al. |
| 7,160,885 | B2 | 1/2007 | Currie et al. |
| 7,189,723 | B2 | 3/2007 | Mitchell et al. |
| 7,259,164 | B2 | 8/2007 | Mitchell et al. |
| 7,312,341 | B2 | 12/2007 | DeSimone et al. |
| 7,405,295 | B2 | 7/2008 | Currie et al. |
| 8,440,667 | B2 * | 5/2013 | Mitchell et al. ............. 514/249 |
| 8,450,321 | B2 * | 5/2013 | Mitchell et al. ............. 514/249 |
| 8,455,493 | B2 * | 6/2013 | Mitchell et al. ............. 514/249 |
| 8,697,699 | B2 | 4/2014 | Mitchell et al. |
| 8,748,607 | B2 * | 6/2014 | Mitchell et al. ............. 544/350 |
| 8,765,761 | B2 | 7/2014 | Mitchell et al. |
| 8,796,270 | B2 | 8/2014 | Mitchell |
| 8,962,835 | B2 * | 2/2015 | Mitchell et al. ............. 544/350 |
| 9,120,811 | B2 | 9/2015 | Mitchell et al. |
| 2003/0212073 | A1 | 11/2003 | Currie et al. |
| 2004/0063715 | A1 | 4/2004 | Paruch et al. |
| 2004/0067951 | A1 | 4/2004 | DeSimone et al. |
| 2004/0072835 | A1 | 4/2004 | Paruch et al. |
| 2004/0102455 | A1 | 5/2004 | Burns et al. |
| 2004/0220189 | A1 | 11/2004 | Sun et al. |
| 2005/0009832 | A1 | 1/2005 | Sun et al. |

(Continued)

FOREIGN PATENT DOCUMENTS

| CA | 2175837 A1 | 5/1995 |
| DE | 4337609 A1 | 5/1995 |

(Continued)

OTHER PUBLICATIONS

Paulekuhn et al. J. Med. Chem. (2007), 50, 6665-6672.*
Berge et al. Journal of Pharmaceutical Sciences (1977) 66(1), 1-19.*
Al-Dabbagh, S. G. et al. (1984). "Species Differences in Oxidative Drug Metabolism: Some Basic Considerations." Archives of Toxicology. Supplement. Archive fur Toxikologie. Supplement, 7:219-231.
Bastin et al, (2000), Org. Proc. Res. Dev., vol. 4, No. 5, pp. 427-435.
Berge et al, J Pharm Sci 1977, vol. 66, Issue 1, pp. 1-19.
Bouloc et al., Bioorg Med Chem Ltrs vol. 20 Iss 20 (2010) pp. 5988-5993.

(Continued)

*Primary Examiner* — Nyeemah A Grazier

(57) ABSTRACT

Disclosed are pharmaceutical compositions comprising a compound having the formula:

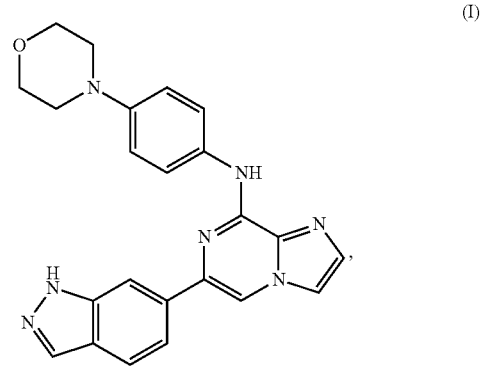

or a pharmaceutically acceptable salt thereof, or a hydrate of thereof, and at least one pharmaceutically acceptable polymer. The pharmaceutically acceptable salt of the compound of Formula I, or a hydrate thereof, can be a mesylate salt, including, for example, a mono-mesylate or a bis-mesylate salt, or a hydrate thereof. Also disclosed are methods of use for the pharmaceutical composition.

57 Claims, 21 Drawing Sheets

(56) References Cited

U.S. PATENT DOCUMENTS

| | | |
|---|---|---|
| 2005/0054648 A1 | 3/2005 | Mitchell et al. |
| 2005/0054649 A1 | 3/2005 | Currie et al. |
| 2005/0085484 A1 | 4/2005 | Mitchell et al. |
| 2005/0090499 A1 | 4/2005 | Currie et al. |
| 2005/0101604 A1 | 5/2005 | Currie et al. |
| 2005/0288295 A1 | 12/2005 | Currie et al. |
| 2006/0069084 A1 | 3/2006 | Burns et al. |
| 2006/0084650 A1 | 4/2006 | Dong et al. |
| 2006/0183746 A1 | 8/2006 | Currie et al. |
| 2007/0117804 A1 | 5/2007 | Zhao et al. |
| 2009/0221612 A1 | 9/2009 | Mitchell et al. |
| 2010/0152159 A1 | 6/2010 | Mitchell et al. |
| 2010/0222323 A1 | 9/2010 | Mitchell et al. |
| 2012/0220582 A1 | 8/2012 | Mitchell et al. |
| 2013/0023499 A1 | 1/2013 | Mitchell et al. |
| 2013/0210802 A1 | 8/2013 | Blomgren et al. |
| 2013/0231330 A1* | 9/2013 | Mitchell et al. .......... 514/210.21 |
| 2013/0237520 A1 | 9/2013 | Mitchell et al. |
| 2013/0237521 A1 | 9/2013 | Mitchell et al. |
| 2013/0267496 A1* | 10/2013 | Mitchell et al. .......... 514/210.21 |
| 2013/0310363 A1 | 11/2013 | Mitchell et al. |
| 2013/0338142 A1 | 12/2013 | Blomgren et al. |
| 2014/0148430 A1 | 5/2014 | Blomgren et al. |
| 2014/0357627 A1 | 12/2014 | Mitchell et al. |
| 2015/0038488 A1 | 2/2015 | Currie et al. |
| 2015/0038504 A1 | 2/2015 | Casteel et al. |
| 2015/0038505 A1* | 2/2015 | Elford et al. ............... 514/233.2 |
| 2015/0150881 A1 | 6/2015 | Di Paolo et al. |
| 2015/0175616 A1 | 6/2015 | Blomgren et al. |
| 2015/0175626 A1* | 6/2015 | Cagulada et al. .......... 514/233.2 |

FOREIGN PATENT DOCUMENTS

| | | |
|---|---|---|
| EP | 480713 A1 | 4/1992 |
| JP | 2001-302667 A | 10/2001 |
| JP | 2004-528295 A | 9/2004 |
| JP | 2005-530739 A | 10/2005 |
| JP | 2008-519843 A | 6/2008 |
| JP | 2010-546786 A | 2/2009 |
| JP | 2011-511835 A | 4/2011 |
| NZ | 593460 A | 11/2013 |
| WO | WO-88/04298 A1 | 6/1988 |
| WO | WO-95/12594 A1 | 5/1995 |
| WO | WO-96/04298 A1 | 2/1996 |
| WO | WO-96/34866 A1 | 11/1996 |
| WO | WO-99/28322 A1 | 6/1999 |
| WO | WO-01/27119 A2 | 4/2001 |
| WO | WO-01/83485 A1 | 11/2001 |
| WO | WO-02/10170 A1 | 2/2002 |
| WO | WO-02/30428 A1 | 4/2002 |
| WO | WO-02/060492 | 8/2002 |
| WO | WO-02/066481 A1 | 8/2002 |
| WO | WO-02/076985 A1 | 10/2002 |
| WO | WO-03/070732 A1 | 8/2003 |
| WO | WO-03/089434 A2 | 10/2003 |
| WO | WO-03/089434 A3 | 10/2003 |
| WO | WO-2004/022562 A1 | 3/2004 |
| WO | WO-2004/026310 A1 | 4/2004 |
| WO | WO-2004/026867 A2 | 4/2004 |
| WO | WO-2004/026877 A1 | 4/2004 |
| WO | WO-2004/072080 A1 | 8/2004 |
| WO | WO-2004/072081 A1 | 8/2004 |
| WO | WO-2005/005429 A1 | 1/2005 |
| WO | WO-2005/014599 A1 | 2/2005 |
| WO | WO-2005/019220 A2 | 3/2005 |
| WO | WO 2005/047290 A2 | 5/2005 |
| WO | WO-2005/085252 A1 | 9/2005 |
| WO | WO-2006/044687 A2 | 4/2006 |
| WO | WO-2006/053121 A2 | 5/2006 |
| WO | WO-2008/025821 A1 | 3/2008 |
| WO | WO-2009/077334 A1 | 6/2009 |
| WO | WO-2009/102468 A1 | 8/2009 |
| WO | WO-2010/006947 A1 | 1/2010 |
| WO | WO-2010/027500 A1 | 3/2010 |
| WO | WO-2010/068257 A1 | 6/2010 |
| WO | WO-2010/068258 A1 | 6/2010 |
| WO | WO 2010068257 A1 * | 6/2010 |
| WO | WO-2011/112995 A1 | 9/2011 |
| WO | WO-2014/028665 A1 | 2/2014 |

OTHER PUBLICATIONS

Bundgaard, H., (1985). *Design of Prodrugs*, Elsevier Science Publishers, B.V., The Netherlands, p. 1.

Dean, D.C. (2000). "Recent Advances in the Synthesis and Applications of Radiolabeled Compounds for Drug Discovery and Development," *Curr. Pharm Des.* 6(10): Preface, 1 page.

Ding, S. et al. (2002) "A Combinatorial Scaffold Approach Toward Kinase-Directed Heterocycle Libraries," *J. Am Chem Soc.*, 124(8):1594-1596.

Elder, et al, (2010) J Pharm Sci, vol. 99, Issue 7, pp. 2948-2961.

European Communication mailed on Jun. 18, 2013, for EP Patent Application No. 11 709 600.8 filed on Mar. 11, 2011, 6 pages.

European Communication mailed on Jun. 6, 2013, for EP Patent Application No. 09 832 228.2 filed on Jun. 21, 2011, 5 pages.

European Communication mailed on Oct. 24, 2012, for European Patent Application No. 09710901.1, filed on Feb. 12, 2009, five pages.

Evans, E.A. (1981). "Synthesis of Radiolabeled Compounds," *J. Radioanal. Chem.* 64(1-2):9-32.

Extended European Search Report mailed on Apr. 26, 2012, for EP 09 83 2229, filed on Jun. 21, 2011, 6 pages.

Extended European Search Report mailed on July 27, 2012, for EP 09 83 2228.2, filed on Jun. 21, 2011, 12 pages.

Extended European Search Report mailed on Mar. 12, 2014, for EP 13005979.3, filed on Dec. 20, 2013, 5 pages.

Final Office Action mailed on Jan. 27, 2012, for U.S. Appl. No. 12/632,151, filed Dec. 7, 2009, 15 pages.

Final Office Action mailed on May 2, 2013 for U.S. Appl. No. 13/343,624, filed Jan. 4, 2012, 9 pages.

Final Office Action mailed on May 25, 2012, for U.S. Appl. No. 12/632,140, filed Dec. 7, 2009, 9 pages.

Final Office Action mailed on Oct. 30, 2012, for U.S. Appl. No. 12/632,140, filed Dec. 7, 2009, 9 pages.

Final Office Action mailed on Sep. 15, 2011, for U.S. Appl. No. 12/632,140, filed Dec. 7, 2009, 15 pages.

Final Office Action mailed on Sep. 5, 2012, for U.S. Appl. No. 12/632,151, filed Dec. 7, 2009, 11 pages.

GenBank Accession No. AY050647.1, created on Oct. 7, 2001, located at <http://www.ncbi.nlm.nih.gov/nuccore/AY050647.1>, last visited on Dec. 28, 2011, 1 page.

Hackam, D.G. et al. (2006). "Translation of Research Evidence From Animals to Humans," *JAMA* 296(14):1731-1732.

International Preliminary Examination Report mailed on Aug. 5, 2004, for PCT Application No. PCT/US2003/12222, filed Apr. 21, 2003, 11 pages.

International Preliminary Examination Report mailed on Oct. 27, 2004, for PCT Application No. PCT/US2003/28329, filed on Sep. 9, 2003, 5 pages.

International Preliminary Report on Patentability mailed on Jan. 5, 2011, for PCT Application No. PCT/US2009/006445, filed on Dec. 7, 2009, 6 pages.

International Preliminary Report on Patentability mailed on Jun. 8, 2011, for PCT Application No. PCT/US/2009/006446, filed on Dec. 7, 2009, 6 pages.

International Preliminary Report on Patentablility mailed on May 12, 2009, for PCT Application No. PCT/US2009/000919, filed on Feb. 12, 2009, 8 pages.

International Search Report and Written Opinion mailed Oct. 13, 2014, for PCT Application No. PCT/US2014/048741, Filed Jul. 29 2014.

International Search Report and Written Opinion mailed on Dec. 30, 2004, for PCT Application No. PCT/US2004/018227, filed on Jun. 4, 2004, 10 pages.

International Search Report and Written Opinion mailed on Dec. 8, 2004, for PCT Application No. PCT/US2004/021150, filed on Jun. 30, 2004, 10 pages.

(56) References Cited

OTHER PUBLICATIONS

International Search Report and Written Opinion mailed on Feb. 1, 2005 for PCT Application No. PCT/US2004/025884, filed on Aug. 11, 2004, 8 pages.
International Search Report and Written Opinion mailed on Jul. 7, 2004, for PCT Application No. PCT/US2004/003922, filed on Feb. 10, 2004, 12 pages.
International Search Report and Written Opinion mailed on Jul. 7, 2004, for PCT Application No. PCT/US2004/003923, filed on Feb. 10, 2004, 12 pages.
International Search Report and Written Opinion mailed on Jun. 23, 2005, for PCT Application No. PCT/US2004/037433, filed on Nov. 10, 2004, 15 pages.
International Search Report and Written Opinion mailed on Oct. 8, 2014, for PCT Application No. PCT/US2014/048733, filed on Jul. 29, 2014.
International Search Report mailed Apr. 26, 2011, for Application No. PCT/US2011/028194, filed on Mar. 11, 2011, 5 pages.
International Search Report mailed on Feb. 12, 2010, for PCT Application No. PCT/US/2009/006446, filed on Dec. 7, 2009, 3 pages.
International Search Report mailed on Feb. 12, 2010, for PCT Application No. PCT/US2009/006445, filed on Dec. 7, 2009, 3 pages.
International Search Report mailed on Feb. 9, 2004, for PCT Application No. PCT/US2003/28329, filed on Sep. 9, 2003.
International Search Report mailed on May 12, 2009, for PCT Application No. PCT/US2009/000919, filed on Feb. 12, 2009, 5 pages.
International Search Report mailed on May 3, 2015, for PCT Application No. PCT/US2014/071842, filed Dec. 22, 2014, 3 pgs.
International Search Report mailed on Oct. 22, 2003, for PCT Application No. PCT/US2003/12222, filed on Apr. 21, 2003.
Invitation to Pay Additional Fees with Partial International Search Report mailed May 3, 2005, for PCT Application No. PCT/US2004/037433, filed on Nov. 10, 2004, 9 pages.
Japanese Decision of Patent mailed Feb. 4, 2014, for Japanese Patent Application No. 2010-546786, filed on Aug. 1, 2010, 4 pages. (with English translation).
Japanese Notice of Reasons for Rejection mailed on Feb. 4, 2014 for Japanese Patent Application No. 2011-539524, filed on Jun. 6, 2011, 10 pages. (with English translation).
Japanese Notice of Reasons for Rejection mailed on Feb. 6, 2014, for Japanese Patent Application No. 2011-539525, filed on Jun. 6, 2011, 11 pages. (with English translation).
Jeffrey, T.K. et al. (1998). "Phosphodiesterase III and V Inhibitors on Pulmonary Artery from Pulmonary Hypertensive Rats: Differences Between Early and established Pulmonary Hypertension", *J. Cardiovascular Pharmacology*, 32(2): 213-219.
Jordan, V.C. (Mar. 2003). "Tamoxifen: A Most Unlikely Pioneering Medicine" *Nature Reviews: Drug Discovery* 2:205-213.
Kabalka, G.W. et al. (1989). "The Synthesis of Radiolabeled Compounds via Organometallic Intermediates," *Tetrahdron* 45(21):6601-21.
Kuhnz, W. et al. (Jun. 11, 1998). "Predicting the Oral Bioavailability of 19-Nortestosterone Progestins In Vivo From Their Metabolic Stability in Human Liver Microsomal Preparation In Vitro," *The American Society for Pharmacology and Experimental Therapeutics* 26(11)1120-1127.
Lumma, JR., W.C. et al. (1983) "Piperazinylimidazo [1,2-a]pyrazines with Selective affinity for in Vitro a-Adrenergic Receptor Subtypes," *J. Med. Chem.* 26(3):357-363.
Non-Final Office Action mailed on Apr. 13, 2011 for U.S. Appl. No. 12/370,103, filed Feb. 12, 2009, 11 pages.
Non-Final Office Action mailed on Apr. 3, 2006, for U.S. Appl. No. 10/776,002, filed Feb. 10, 2004, 13 pages.
Non-Final Office Action mailed on Dec. 31, 2013, for U.S. Appl. No. 13/901,523, filed May 23, 2013, 22 pages.
Non-Final Office Action mailed on Feb. 17, 2012 for U.S. Appl. No. 12/632,140, filed Dec. 7, 2009, 11 pages.
Non-Final Office Action mailed on Jan. 25, 2013, for U.S. Appl. 13/343,624, filed Jan. 4, 2012, 18 pages.
Non-Final Office Action mailed on Jan. 8, 2007, for U.S. Appl. No. 10/915,696, filed Aug. 11, 2004, 8 pages.
Non-Final Office Action mailed on Jun. 29, 2011, for U.S. Appl. No. 12/632,151, filed on Dec. 7, 2009, 17 pages.
Non-Final Office Action mailed on May 10, 2011 for U.S. Appl. No. 12/632,140, filed Dec. 7, 2009, 18 pages.
Non-Final Office Action mailed on May 17, 2012, for U.S. Appl. No. 12/632,151, filed Dec. 7, 2009, 15 pages.
Non-Final Office Action mailed on May 24, 2006, for U.S. Appl. No. 10/776,631, filed Feb. 10, 2004, 10 pages.
Non-Final Office Action mailed on Nov. 4, 2013, for U.S. Appl. No. 13/862,147, filed Apr. 12, 2013, 18 pages.
Non-Final Office Action mailed on Oct. 11, 2012, for U.S. Appl. No. 13/441,441, filed on Apr. 6, 2012, 8 pages.
Non-Final Office Action mailed on Oct. 11, 2013, for U.S. Appl. No. 13/868,967, filed Apr. 23, 2013, 17 pages.
Non-Final Office Action mailed on Oct. 16, 2013, for U.S. Appl. No. 13/868,971, filed Apr. 23, 2013, 16 pages.
Non-Final Office Action mailed on Sep. 26, 2006, for U.S. Appl. No. 10/658,121, filed Sep. 9, 2003, 7 pages.
Notice of Allowance mailed Apr. 20, 2007, for U.S. Appl. No. 10/915,696, filed Aug. 11, 2004, 7 pages.
Notice of Allowance mailed Aug. 11, 2006, for U.S. Appl. No. 10/776,002, filed Feb. 10, 2004, 10 pages.
Notice of Allowance mailed Aug. 8, 2007, for U.S. Appl. No. 10/658,121, filed Sep. 9, 2003, 4 pages.
Notice of Allowance mailed Mar. 6, 2007, for U.S. Appl. No. 10/658,121, filed Sep. 9, 2003, 6 pages.
Notice of Allowance mailed on Aug. 12, 2013, for U.S. Appl. No. 13/343,624, filed Jan. 4, 2012 , 9 pages.
Notice of Allowance mailed on Dec. 26, 2013, for U.S. Appl. No. 13/343,624, filed Jan. 4, 2012, 10 pages.
Notice of Allowance mailed on Feb. 12, 2014, for U.S. Appl. No. 13/862,147, filed Apr. 12, 2013, 9 pages.
Notice of Allowance mailed on Feb. 5, 2014, for U.S. Appl. No. 13/868,967, filed Apr. 23, 2013, 8 pages.
Notice of Allowance mailed on Jan. 14, 2013, for U.S. Appl. No. 12/632,151, filed Dec. 7, 2009, 8 pages.
Notice of Allowance mailed on Jan. 25, 2013, for U.S. Appl. No. 12/632,140, filed Dec. 7, 2009, 8 pages.
Notice of Allwance mailed on Jan. 28, 2013, for U.S. Appl. No. 13/441,441, filed Apr. 6, 2012, 8 pages.
Notice of Allowance mailed on Jan. 30, 2014, for U.S. Appl. No. 13/868,971, filed Apr. 23, 2013, 8 pages.
Notice of Allowance mailed Sep. 7, 2006, for U.S. Appl. No. 10/776,631, filed Feb. 10, 2004, 7 pages.
Office Action Dated Dec. 15, 2014 for Japan Patent Application No. 2014-095907.
Office Action Dated Jan. 15, 2015 for Chilean Patent Application No. 1360-11.
Office Action Dated Jan. 30, 2015 for Vietnamese Patent Application No. 1-2011-01623.
Office Action Dated Feb. 18, 2015 for Eurasian Patent Application No. 201400197.
Office Action Dated Mar. 30, 2015 for European Patent Application No. 13 005 979.3.
Oravcova, J. et al. (1996). "Drug Protein Binding Studies New Trends in Analytical and Experimental Methodolgy," *J Chromatogr B* 677:1-28.
Paulekuhn et al., J Med Chem 2007, 50, pp. 6665-6672.
Resolution Dated Dec. 18, 2014 for Colombian Patent Application No. 14-049.611.
Restriction Requirement mailed Dec. 8, 2010, for U.S. Appl. No. 12/632,140, filed Dec. 7, 2009, 10 pages.
Restriction Requirement mailed Jan. 27, 2006, for U.S. Appl. No. 10/776,631, filed Feb. 10, 2004, 6 pages.
Restriction Requirement mailed Jan. 30, 2006, for U.S. Appl. No. 10/658,121, filed Sep. 9, 2003, 5 pages.
Restriction Requirement mailed Jan. 4, 2006, for U.S. Appl. No. 10/776,002, filed Feb. 10, 2004, 7 pages.
Restriction Requirement mailed May 18, 2006, for U.S. Appl. No. 10/658,121, filed Sep. 9, 2003, 5 pages.

(56) References Cited

OTHER PUBLICATIONS

Restriction Requirement mailed Oct. 13, 2006, for U.S. Appl. No. 10/915,696, filed Aug. 11, 2004, 5 pages.
Restriction Requirement mailed Oct. 20, 2004, for U.S. Appl. No. 10/419,682, filed Apr. 21, 2003, 9 pages.
Restriction Requirement mailed on Apr. 14, 2014, for U.S. Appl. No. 13/862,194, filed Apr. 12, 2013, 5 pages.
Restriction Requirement mailed on Dec. 8, 2010, for U.S. Appl. No. 12/632,151, filed Dec. 7, 2009, 10 pages.
Restriction Requirement mailed on Feb. 17, 2011, for U.S. Appl. No. 12/370,103, filed Feb. 12, 2009, 10 pages.
Restriction Requirement mailed on Jan. 27, 2014, for U.S. Appl. No. 13/609,068, filed Nov. 26, 2012, 8 pages.
Restriction Requirement mailed on Jul. 26, 2012, for U.S. Appl. No. 13/441,441, filed Apr. 6, 2012, 9 pages.
Restriction Requirement mailed on Jul. 3, 2013, for U.S. Appl. No. 13/868,971, filed Apr. 23, 2013, 5 pages.
Restriction Requirement mailed on Jun. 14, 2013, for U.S. Appl. No. 13/862,147, filed Apr. 12, 2013, 10 pages.
Restriction Requirement mailed on Jun. 24, 2013, for U.S. Appl. No. 13/868,967, filed Apr. 23, 2013, 10 pages.
Restriction Requirement mailed on Nov. 27, 2012, for U.S. Appl. No. 13/343,624, filed Jan. 4, 2012, 10 pages.
Restriction Requirement mailed on Oct. 15, 2013, for U.S. Appl. No. 13/901,523, filed May 23, 2013, 5 pages.
Restriction Requirement mailed on Sep. 8, 2014, for U.S. Appl. No. 14/274,618, filed May 9, 2014, 6 pages.
Second Written Opnion mailed on Apr. 13, 2004, for PCT Application No. PCT/US2003/12222, filed Apr. 21, 2003, 7 pages.
Silverman, R.B. (1992), *The Organic Chemistry of Drug Design and Drug Action*, Academic Press, Inc. San Diego, CA, pp. 352-400.
Stenberg, K.A.E. et al., (2000). "KinMutBase, a Database of Human Disease-Causing Protein Kinase Mutations", *Nucleic Acids Research* 28(1):369-371.
Taylor, R. et al., (1984). "Hydrogen-Bond Geometry in Organic Crystals", *Acc. Chem Res.* 17:320-326.
Vitse, O. et al. (1999). "New Imidazo [1,2α]pyrazine Derivatives with Bronchodilatory and Cyclic Nucleotide Phosphodiesterase Inhibitory Activities," *Bioorganic and Medicinal Chemistry* 7:1059-1065.
Written Opinion mailed Apr. 26, 2011, for Application No. PCT/US2011/028194, filed on Mar. 11, 2011, 6 pages.
Written Opinion mailed Dec. 5, 2003, for PCT Application No. PCT/US2003/12222, filed Apr. 21, 2003, 6 pages.
Written Opinion mailed Jul. 6, 2004, for PCT Application No. PCT/US2003/28329, filed on Sep. 9, 2003, 5 pages.
Written Opinion mailed on Feb. 12, 2010, for PCT Application No. PCT/US/2009/0066446, filed on Dec. 7, 2009, 4 pages.
Written Opinion mailed on Feb. 12, 2010, for PCT Application No. PCT/US2009/006445, filed on Dec. 7, 2009, 4 pages.
Written Opinion mailed on May 12, 2009, for PCT Application No. PCT/US2009/000919, filed on Feb. 12, 2009, 7 pages.
Zaragoza, D.F. (2005). *Side Reactions in Organic Synthesis: A Guide to Successful Synthesis Design*, Weinheim; Wiley-VCH Verlag GmbH &Co. KGaA, Preface, 2 pages.

\* cited by examiner

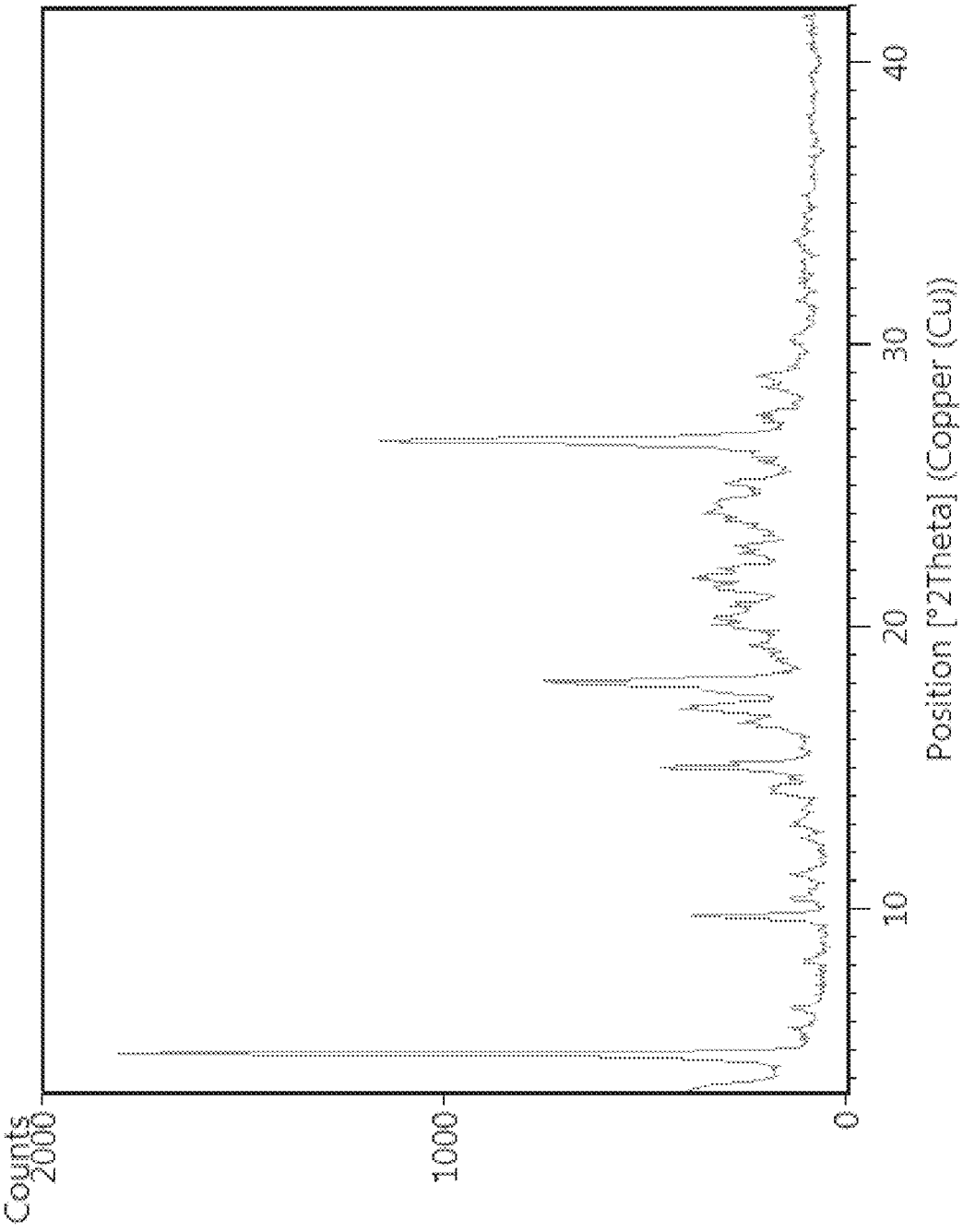

FORMULATION OF SYK INHIBITORS

CROSS REFERENCE TO RELATED APPLICATIONS

This application claims the benefit of U.S. Provisional Patent Application Ser. No. 61/860,198, filed Jul. 30, 2013, the disclosure of which is hereby incorporated herein by reference in its entirety.

FIELD

The present disclosure relates to pharmaceutical compositions of compounds that inhibit Spleen Tyrosine Kinase (Syk) activity. The disclosure also relates to methods of preparing such pharmaceutical compositions, and the use of such pharmaceutical compositions in treating subjects with various diseases, including cancer and inflammatory conditions.

BACKGROUND

A number of imidazopyrazine compounds are under investigation for inhibiting Spleen Tyrosine Kinase (Syk) activity. Syk is a non-receptor tyrosine kinase that plays critical roles in immunoreceptor- and integrin-mediated signaling in a variety of cell types, including B-cells, macrophages, monocytes, mast cells, eosinophils, basophils, neutrophils, dendritic cells, T-cells, natural killer cells, platelets, and osteoclasts.

Syk has been reported to play an important role in signaling through the B-cell receptor, known to be an important survival signal in B-cells. As such, inhibition of Syk activity may be useful for treating certain types of cancer, including B-cell lymphoma and leukemia. Additionally, the inhibition of Syk activity is believed to be useful for treating other diseases and conditions, including inflammatory diseases (e.g., rheumatoid arthritis), allergic disorders and autoimmune diseases.

One such compound that has been found to inhibit Syk activity is represented by Formula I:

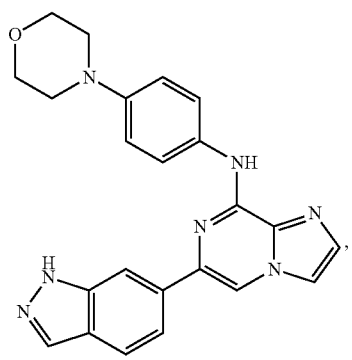

(I)

or a pharmaceutically acceptable salt thereof. This compound and its synthesis have been described in U.S. Pat. Nos. 8,450,321 and 8,455,493, which are hereby incorporated herein by reference in their entirety, and are hereby incorporated by reference specifically with reference to Examples 1 and 2.

Early clinical programs have focused on oral administration of the compound of Formula I. What is desired is an oral formulation of the compound of Formula I that has low inter-subject variability, extended dose linearity, and low drug-drug-interaction. Additionally, what is desired is a commercially viable manufacturing process for the formulation of the compound of Formula I. For example, what is desired is a process that has little or no variability when different batches of the active pharmaceutical ingredient are produced, and that can be easily handled and manufactured on a commercial scale. What is also desired is a formulation that is both chemically and physically stable during the manufacturing process and upon storage.

SUMMARY

Provided herein are pharmaceutical compositions (including, for example, formulations for oral administration) of the compound of Formula I, that address one or more of the unmet needs described above. The pharmaceutical compositions (including, for example, formulations for oral administration) provided may lower inter-subject variability of biopharmaceutical responses in subjects. Additionally, the pharmaceutical compositions (including, for example, formulations for oral administration) provided may exhibit extended dose linearity, which may lead to higher efficacy. The pharmaceutical compositions (including, for example, formulations for oral administration) provided may lower drug-drug-interaction of the compound of Formula I with other drugs, particularly with antacids, which may increase bioavailability of the compound of Formula I in subjects (e.g. humans) who may be taking such other drugs (e.g., antacids).

In particular, the pharmaceutical compositions provided have good biopharmaceutical performance; can be manufactured using a robust, scalable and commercially viable solid dosage formulation and process; and exhibit physical and chemical stability, both during the manufacturing process and after the manufacturing process (e.g., on storage).

In some aspects, provided is a composition comprising a compound of Formula I, or a salt thereof, or hydrate of the foregoing, and a carrier. The composition may be a pharmaceutical composition (such as a pharmaceutical composition formulated for oral administration), or a precursor composition (such as a feed solution for spray drying or the spray-dried powder formed from spray drying) used in manufacturing a pharmaceutical composition in tablet form. The composition may be in liquid form (e.g., when the composition is a feed solution for spray drying) or in solid form (e.g., when the composition is a tablet or is in the form of a spray-dried powder).

In some aspects, provided is a composition comprising a pharmaceutically acceptable salt of the compound of Formula I, or a hydrate thereof, and a pharmaceutically acceptable carrier. In certain embodiments, the pharmaceutically acceptable carrier is a pharmaceutically acceptable polymer.

In certain aspects, provided is a composition comprising:
(i) a mesylate salt of a compound of Formula I:

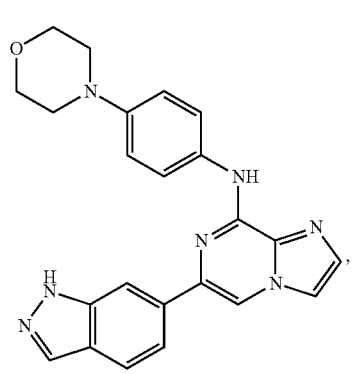

(I)

or a hydrate thereof,
wherein the mesylate salt comprises a cation of the compound of Formula I and a mesylate anion, and wherein the molar ratio of the mesylate anion to the cation of the compound of Formula I is at least 1:1; and
(ii) a pharmaceutically acceptable carrier.

In one variation, the molar ratio of the mesylate anion to the cation of the compound of Formula I is between 1:1 and 3.3:1. In another variation, the molar ratio of the mesylate anion to the cation of the compound of Formula I is between 1.9:1 and 3.3:1.

In some embodiments, the mesylate salt of a compound of Formula I, or a hydrate thereof, is a hydrate, bis-mesylate salt of the compound of Formula I. In certain embodiments, the mesylate salt of a compound of Formula I, or a hydrate thereof, is a monohydrate, bis-mesylate salt of the compound of Formula I. In other embodiments, the mesylate salt of a compound of Formula I, or a hydrate thereof, is a mono-mesylate salt of the compound of Formula I, or a hydrate thereof.

In certain aspects, provided is a composition comprising:
(i) a bis-mesylate salt of a compound of Formula I:

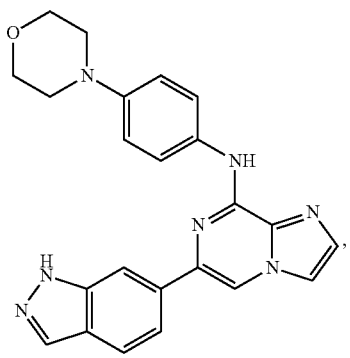

or a hydrate thereof, and
(ii) a pharmaceutically acceptable carrier.

In some embodiments, the bis-mesylate salt of a compound of Formula I, or a hydrate thereof, is a monohydrate, bis-mesylate salt of the compound of Formula I.

In another aspect, provided is a composition comprising:
(i) a compound of Formula I:

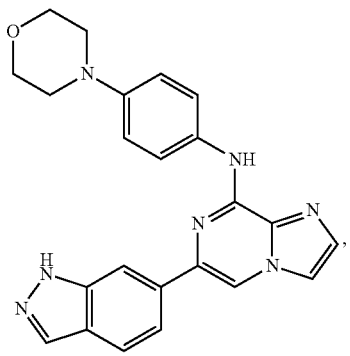

or a cation thereof;
(ii) methanesulfonic acid, or an anion thereof; and
(iii) a pharmaceutically acceptable carrier.

In some aspects, provided is a composition comprising a hydrate of a compound of Formula I, or a cation thereof, and methanesulfonic acid, or an anion thereof. In one variation, the hydrate is a monohydrate.

In some embodiments, the composition described herein (including, for example, the pharmaceutical compositions described herein) is a tablet. In one embodiment, a bis-mesylate salt of a compound of Formula I (such as a bis-mesylate salt of Formula IA) is formulated as a tablet. In one variation, a tablet provided herein comprises a hydrate of a bis-mesylate salt of a compound of Formula I. In another variation, a tablet provided herein comprises a monohydrate of a bis-mesylate salt of a compound of Formula I. In yet another variation, a tablet provided herein comprises polymorph Form 3, which is a polymorph of a monohydrate of a bis-mesylate salt of a compound of Formula I.

In another embodiment, a mono-mesylate salt of a compound of Formula I (such as a mono-mesylate salt of Formula IIA) is formulated as a tablet. In one variation, a tablet provided herein comprises a mono-mesylate salt of a compound of Formula I.

In some embodiments, compositions described herein (including, for example, the pharmaceutical compositions described herein) are formulated as a tablet comprising a solid dispersion. Such a tablet may be referred to herein as a "solid dispersion tablet". In certain embodiments, compositions described herein (including, for example, the pharmaceutical compositions described herein) are formulated as a tablet comprising a spray-dried solid dispersion. Such a tablet may be referred to herein as a "spray-dried solid dispersion tablet". In certain embodiments, tablets comprising a solid dispersion described herein (including, for example, the tablets comprising a spray-dried solid dispersion) further comprise a polymer matrix. In one variation, a bis-mesylate salt of a compound of Formula I (such as a bis-mesylate salt of Formula IA) is dispersed within the polymer matrix. In one variation, the polymer matrix is formed or obtainable from the pharmaceutically acceptable polymer. In another variation, the polymer matrix is formed or obtainable from hydroxypropylmethylcellulose.

In one variation, a tablet provided herein comprises a mesylate salt of a compound of Formula I. In another variation, a tablet provided herein comprises a mesylate salt of a compound of Formula I, or a hydrate thereof, wherein the mesylate salt comprises a cation of the compound of Formula I and a mesylate anion, and wherein the molar ratio of the mesylate anion to the cation of the compound of Formula I is between 1.9:1 and 3.3:1.

As described in further detail herein, a compound of Formula I, or a pharmaceutically acceptable salt thereof (including, for example, a bis-mesylate salt of the compound of Formula I), or a hydrate thereof, may be combined with a carrier (which may be a pharmaceutically acceptable carrier) to form a feed solution, which is spray dried to manufacture a spray-dried powder (also known as a solid dispersion or solid dispersion particles). In one variation, the feed solution further comprises water, and optionally additional solvent. Thus, also provided herein is a spray-dried powder comprising a compound of Formula I or a pharmaceutically acceptable salt thereof, such as a spray-dried powder comprising a bis-mesylate salt of a compound of Formula I. The spray-dried powder may then be combined with at least one additional pharmaceutically acceptable carrier (e.g., by dry granulation), and the resulting granulation may be compressed into a tablet. In one variation, at least one pharmaceutically acceptable carrier used in spray drying is a pharmaceutically acceptable polymer. The pharmaceutically acceptable polymer may form a polymer matrix. Thus, in one aspect is provided a composition comprising a pharmaceutically acceptable salt of the compound of Formula I, or a hydrate thereof (including, for example, a bis-mesylate salt of a compound of Formula I) dispersed within a polymer matrix. In another aspect, a composition is provided that comprises a pharmaceutically acceptable salt of the compound of Formula I, or a hydrate thereof (including, for example, a bis-mesylate salt of a compound of Formula I) and at least one pharmaceutically acceptable carrier dispersed within a polymer matrix. In a particular aspect, the polymer matrix is formed or obtainable from hydroxypropylmethylcellulose.

In certain embodiments, provided herein is a tablet comprising spray-dried powder, wherein the spray-dried powder comprises a compound of Formula I or a pharmaceutically acceptable salt thereof, such as a spray-dried powder comprising a bis-mesylate salt of a compound of Formula I, and such tablet is characterized by an X-ray diffraction pattern comprising 2θ-reflections (±0.2°) at 6.3 and between 26.1 to 26.6. It should be understood that ±0.2° can also be expressed as "plus or minus 0.2 degrees 2θ".

In other embodiments, the tablet is a dry granulation tablet. A tablet formed by dry granulation is referred to herein as a "dry granulation tablet". In one variation, the solid dispersion tablet, such as the spray-dried solid dispersion tablet, is a dry granulation tablet.

In another variation, as described in further detail herein, a pharmaceutically acceptable salt of a compound of Formula I (including, for example, a bis-mesylate salt of the compound of Formula I), or a hydrate thereof, may be manufactured into a tablet by combining the pharmaceutically acceptable salt of the compound of Formula I (including, for example, the bis-mesylate salt of a compound of Formula I), or a hydrate thereof, with a pharmaceutically acceptable carrier by dry granulation to form a granulation, and compressing the granulation into a tablet.

In certain embodiments, the tablet comprises a polymorph of a monohydrate, bis-mesylate salt of a compound of Formula I (which may also be referred to herein as "Form 3", "Form III" or "polymorph Form 3"), characterized by or having an X-ray diffraction pattern comprising 2θ-reflections (±0.2°) at 13.8, 16.9, 22.9, and 26.1. In other embodiments of the tablet, a polymorph of a monohydrate, bis-mesylate salt of a compound of Formula I is polymorph Form 3, characterized by or having an X-ray diffraction pattern comprising 2θ-reflections (±0.2°) at 7.7, 12.9, 17.7, and 18.1. In yet other embodiments of the tablet, a polymorph of a monohydrate, bis-mesylate salt of a compound of Formula I is polymorph Form 3, characterized by or having an X-ray diffraction pattern comprising 2θ-reflections (±0.2°) at 7.7, 12.9, 13.8, 16.9, 17.7, 18.1, 22.9, and 26.1. When describing the 2θ-reflections in the X-ray diffraction pattern, it should be understood that ±0.2° can also be expressed as "plus or minus 0.2 degrees 2θ". In some embodiments of the tablet, a polymorph of a monohydrate, bis-mesylate salt of a compound of Formula I is polymorph Form 3, characterized by or having an X-ray diffraction pattern substantially as shown in FIG. 1A. In other embodiments of the tablet, a polymorph of a monohydrate, bis-mesylate salt of a compound of Formula I is polymorph Form 3, characterized by or having an X-ray diffraction pattern substantially as shown in FIG. 1B.

In one aspect, provided is a pharmaceutical composition comprising a bis-mesylate salt of formula IA:

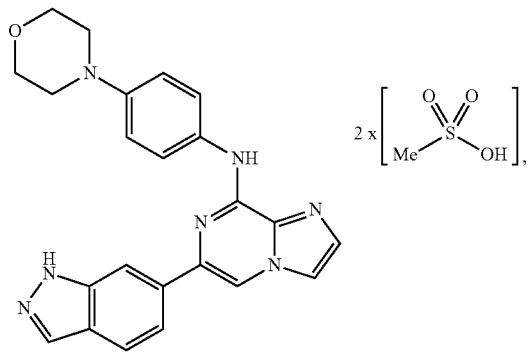

and at least one pharmaceutically acceptable polymer. One of skill in the art would understand that when the bis-mesylate salt is depicted as Formula IA above, the ionic form (e.g., the cationic form of the compound of Formula I and the anionic form of the methanesulfonic acid) is intended. In one variation, the bis-mesylate salt of formula IA is a hydrate.

In some embodiments, a bis-mesylate salt of formula IA is formulated as a tablet. Thus, in one aspect, tablets as detailed herein comprising a bis-mesylate salt of formula IA, or a hydrate thereof.

In certain embodiments, a bis-mesylate salt of formula IA, or a hydrate thereof, is formulated as a solid dispersion tablet. In one variation, the solid dispersion tablet is a spray-dried solid dispersion tablet. In certain embodiments, a solid dispersion tablet (such as a spray-dried solid dispersion tablet) comprising a bis-mesylate salt of formula IA, further comprises at least one pharmaceutically acceptable polymer, which may be in the form of a polymer matrix. In another variation, the at least one pharmaceutically acceptable polymer forms a polymer matrix. In yet another variation, the bis-mesylate salt of formula IA is dispersed within the polymer matrix.

In other embodiments, the tablet is a dry granulation tablet. In one variation, the bis-mesylate salt of formula IA, or a hydrate thereof, is a Form 3 polymorph characterized by or having an X-ray diffraction pattern comprising 2θ-reflections (±0.2°) at 13.8, 16.9, 22.9, and 26.1.

In some embodiments of the compositions described herein (including, for example, the pharmaceutical composition, tablet, feed solution, and spray-dried powder described herein) in which the compositions comprise a pharmaceutically acceptable polymer, the pharmaceutically acceptable polymer is a precipitation inhibitor. In one variation, the composition comprises a pharmaceutically acceptable polymer, wherein the pharmaceutically acceptable polymer is hydroxypropylmethylcellulose (HPMC). In another variation, the composition comprises a pharmaceutically acceptable polymer, wherein the pharmaceutically acceptable polymer is copovidone. In other embodiments, the pharmaceutical composition further comprises at least one diluent. As such, compositions are provided comprising a pharmaceutically acceptable polymer (such as HPMC and/or copovidone) and a diluent. In one variation, the composition comprises a diluent wherein the diluent is mannitol. In yet other embodiments, the composition comprises any one or more of crospovidone, poloxamer, colloidal silicon dioxide, magnesium stearate, and microcrystalline cellulose.

Provided is also a unit dosage form comprising a pharmaceutical composition as described above. In some embodiments, the unit dosage form is a tablet. Provided is also an article of manufacture comprising a pharmaceutical composition as described above, or a unit dosage form as described above.

In yet another aspect, provided is a method of treating a condition in a subject in need thereof, comprising administering to the subject a therapeutically effective amount of a pharmaceutical composition as described above, or therapeutically effective amount of a unit dosage form as described above, wherein the condition is selected from the group consisting of cancer and autoimmune disease. In some embodiments, the condition is selected from the group consisting of acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), mantle cell lymphoma (MCL), follicular lymphoma (FL), Waldestrom's macroglobulinemia (WM), T-cell lymphoma, B-cell lymphoma, diffuse large B-cell lymphoma (DLBCL), lymphoplasmacytic lymphoma (LPL), and marginal zone lymphoma (MZL). In certain embodiments, the condition is non-Hodgkin's lymphoma. In one variation, the NHL is indolent non-Hodgkin's lymphoma (iNHL). In another variation, the iNHL is refractory iNHL. In yet another variation, the iNHL is non-FL iNHL. In other embodiments, the condition is selected from the group consisting of asthma, rheumatoid arthritis, multiple sclerosis, and lupus. In some of the foregoing embodiments, the subject is human.

DESCRIPTION OF THE FIGURES

FIGS. 1C and 1D are exemplary XRPD patterns of polymorph Form 7. The XRPD pattern in FIG. 1D was obtained at 25° C. and 53% relative humidity (RH).

DETAILED DESCRIPTION

Figure 1A:
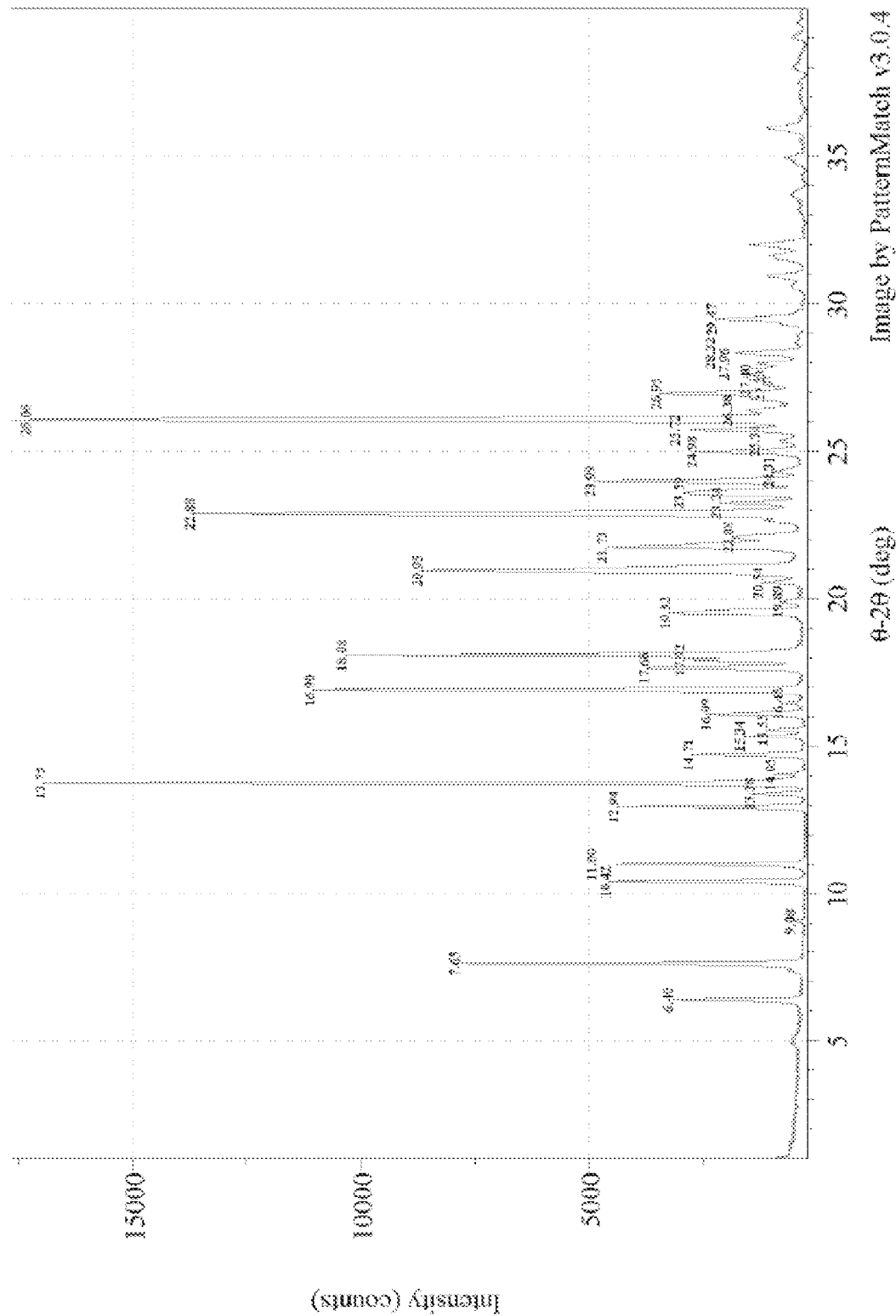
FIGS. 1A and 1B are exemplary X-ray powder diffraction pattern (XRPD) patterns of polymorph Form 3.

The following examples are included to illustrate embodiments of the disclosure, and are not intended to limit the scope of the disclosure. It should be appreciated by those of skill in the art that the techniques disclosed herein represent techniques that apply in the practice of the disclosure. Those of skill in the art would appreciate that, in light of the present disclosure, changes can be made in the examples herein without departing from the spirit and scope of the disclosure.

Provided herein are compositions comprising a pharmaceutically acceptable salt of a compound of Formula I:

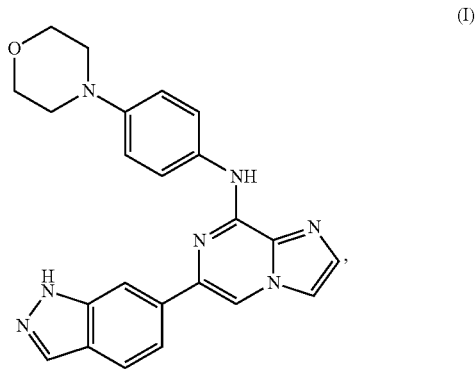 [SMILES: c1cn2cc(-c3ccc4cn[nH]c4c3)nc(Nc3ccc(N4CCOCC4)cc3)c2n1]

or a hydrate thereof, and at least one pharmaceutically acceptable carrier.

Various types of compositions are provided herein. In some variations, the composition is a pharmaceutical composition, such as a pharmaceutical composition formulated for oral administration. In certain variations, the composition is a tablet prepared by dry granulation and compression. In certain variations, the composition is a tablet prepared by formulating a compound of Formula I, or a pharmaceutically acceptable salt thereof, or a hydrate thereof, as a granulation. In other variations, the composition is a tablet prepared by formulating a compound of Formula I, or a pharmaceutically acceptable salt thereof, or hydrate thereof, as a solid dispersion, and formulating the solid dispersion in the tablet as a dry granulation. In other variations, the composition is a feed solution for spray drying. In yet other variations, the composition is a spray-dried powder formed from spray drying, which may be used in manufacturing a pharmaceutical composition in tablet form.

The term "pharmaceutically acceptable" indicates that the material does not have properties that would cause a reasonably prudent medical practitioner to avoid administration of the material to a subject (e.g. a human), taking into consideration the disease or conditions to be treated and the respective route of administration.

In one aspect, provided are pharmaceutical compositions comprising a pharmaceutically acceptable salt of the compound of Formula I:

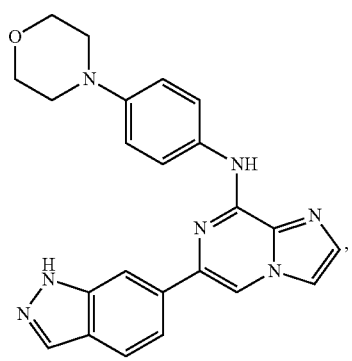

(I)

or a hydrate thereof, and at least one pharmaceutically acceptable carrier.

Such pharmaceutical compositions comprise a more soluble salt form of the compound of Formula I that was unexpectedly identified, and in one aspect comprise specific excipients selected to minimize precipitation of the salt form of the compound of Formula I, or hydrate thereof, once dissolved. Consequently, such compositions (including, for example, pharmaceutical compositions) may address the needs described above with respect to low inter-subject pharmacokinetic variability, extended dose linearity, and low drug-drug-interaction.

Additionally, pharmaceutical compositions provided herein have been observed to be chemically and physically stable during the manufacturing process and over time, and maintain the advantages of an effective therapeutic for the treatment of various diseases that involve the inhibition of Syk activity, including, for example, cancer and inflammatory conditions.

Methods of making and using such compositions are also provided, as are kits, unit dosage forms, and articles of manufacture comprising a pharmaceutically acceptable salt of a compound of Formula I, or a hydrate thereof.

Compound of Formula I, and Salts, Hydrates and Polymorphs Thereof

The compositions provided herein comprise a pharmaceutically acceptable salt of a compound of Formula I:

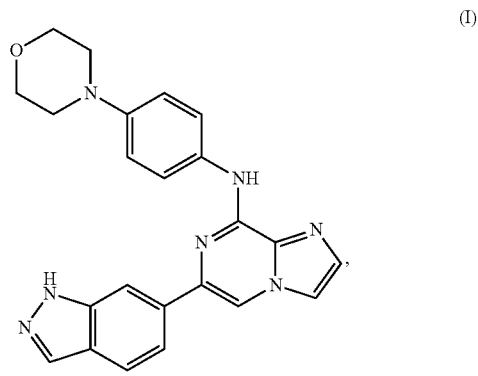 [SMILES: c1cn2cc(-c3ccc4cn[nH]c4c3)nc(Nc3ccc(N4CCOCC4)cc3)c2n1]

(I)

or a hydrate thereof. The compound of Formula I may exist as a free base or in various salt forms, or hydrates thereof, and compositions comprising any of these forms are provided herein. In some embodiments, the compositions, methods of making and using such compositions, kits, unit dosage forms and articles of manufacture provided herein comprise a mesylate salt of a compound of Formula I, or a hydrate thereof. In some variations, the mesylate salt is a mono-mesylate or a bis-mesylate salt, or a hydrate thereof.

In one variation, the compositions, methods of making and using such compositions, kits, unit dosage forms and articles of manufacture provided herein comprise a mono-mesylate salt of a compound of Formula I, or a hydrate thereof. In another variation, the compositions, methods of making and using such compositions, kits, unit dosage forms and articles of manufacture provided herein comprise a bis-mesylate salt of a compound of Formula I, or a hydrate thereof. In yet another variation, the compositions, methods of making and using such compositions, kits, unit dosage forms and articles of manufacture provided herein comprise a free base, mono-mesylate salt, bis-mesylate salt of the compound of Formula I, or a hydrate thereof, or any combinations of the foregoing. It should be understood that "mono-mesylate salt" may also be referred to herein as "mono-MSA salt", and that "bis-mesylate salt" may also be referred to herein as "bis-MSA salt".

The form in which a compound of Formula I, or a salt or hydrate thereof, is present in the composition may vary depending on the type of composition, and the method for preparing such composition. For example, a composition may be a tablet made by dry granulation and compression of a polymorph of a monohydrate, bis-mesylate salt of a compound of Formula I (e.g., polymorph Form 3). Thus, in one variation, provided is a composition (e.g., a tablet) comprising a polymorph of a monohydrate, bis-mesylate salt of a compound of Formula I (e.g., polymorph Form 3). In another example, the composition may be a tablet made by spray drying a feed solution comprising a mesylate salt of a compound of Formula I and methanesulfonic acid to form spray-dried powder (also referred to as a solid dispersion), and dry granulating and compressing the spray-dried powder to form the tablet. Thus, in other variations, provided is a composition (e.g., a feed solution, a spray-dried powder or solid dispersion, or a tablet) comprising a mesylate salt of a compound of Formula I.

Mesylate Salts Thereof

In some embodiments, the pharmaceutically acceptable salt of the compound of Formula I, or a hydrate thereof, is a mesylate salt of the compound of Formula I, or a hydrate thereof. The mesylate salt comprises a cation of the compound of Formula I and a mesylate anion. In one variation, the mesylate anion and the cation of the compound of Formula I are present in a molar ratio of the mesylate anion to the cation of the compound of Formula I of at least 1:1, or between 1:1 and 3.3:1, between 1.9:1 and 3.3:1, between 1.9:1 and 2.5:1, between 1.9:1 and 2.4:1, between 2:1 to 3.3:1, between 2:1 and 3:1, or between 2:1 and 2.7:1, or between 2.1:1 and 2.5:1, or between 2.2:1 and 2.4:1, or about 2.3:1, or about 2.4:1. In another variation, the molar ratio of the mesylate anion to the cation of the compound of Formula I is greater than 1:1 and less than 2:1. In yet another variation, the molar ratio of the mesylate anion to the cation of the compound of Formula I is greater than 2:1.

In certain embodiments, the pharmaceutically acceptable salt of the compound of Formula I, or a hydrate thereof, is a bis-mesylate salt of the compound of Formula I, or a hydrate thereof. The bis-mesylate salt may be depicted herein in various ways.

In one variation, a bis-mesylate salt is represented by Formula IA:

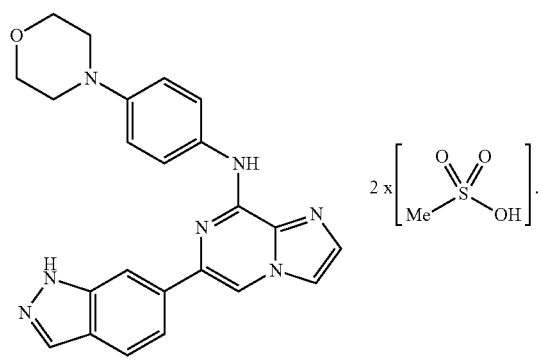

(IA)

One of skill in the art would understand that when the bis-mesylate salt is depicted as Formula IA above, the ionic form (e.g., the cationic form of the compound of Formula I and the anionic form of the methanesulfonic acid) is intended.

Without wishing to be bound by any theory, in another variation, a bis-mesylate salt may be represented by Formula IB:

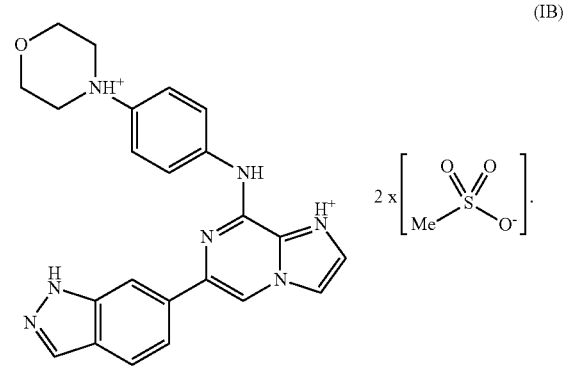

(IB)

Without wishing to be bound by any theory, in yet another variation, the bis-mesylate salt is a monohydrate, bis-mesylate salt of a compound of Formula I, which may be represented by Formula IC:

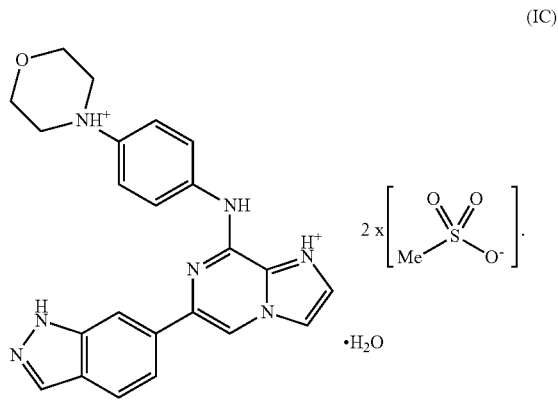

(IC)

In some embodiments, the pharmaceutically acceptable salt of the compound of Formula I, or a hydrate thereof, is a hydrate, bis-mesylate salt of the compound of Formula I. In some variations, the hydrate, bis-mesylate salt comprises at least two molecules of water. Without wishing to be bound by any theory, in one variation, a hydrate, bis-mesylate salt may be represented by Formula ID:

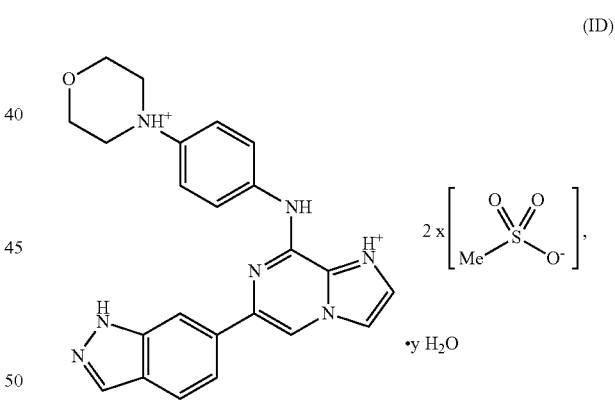

(ID)

wherein y is at least 0.5. In some variations, y is at least 1, at least 1.5, at least 2, at least 2.5, at least 3, at least 4, or between 0.5 and 5, between 0.5 and 4, between 0.5 and 2, between 0.5 and 1.5, or about 0.5, about 1, about 1.5, about 2, about 3, or about 4. In certain variations, y is an integer. For example, when y is 2, the compound of Formula ID is a bis-hydrate, bis-mesylate salt. In other variations, y is a non-integer.

Without wishing to be bound by any theory, in another variation, a hydrate, bis-mesylate salt may be represented by Formula IE:

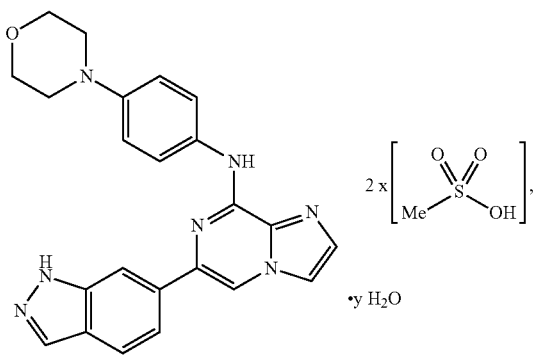

(IE)

wherein y is at least 0.5. In some variations, y is at least 1, at least 1.5, at least 2, at least 2.5, at least 3, or at least 4, or between 0.5 and 5, between 0.5 and 4, between 0.5 and 2, between 0.5 and 1.5, or about 0.5, about 1, about 1.5, about 2, about 3, or about 4. In certain variations, y is an integer. For example, when y is 2, the compound of Formula IE is a bis-hydrate, bis-mesylate salt. In other variations, y is a non-integer.

Pharmaceutical compositions comprising a bis-mesylate salt of a compound of Formula I, or a hydrate thereof, were surprisingly observed to have improved solubility, and thus, improved bioavailability compared to pharmaceutical compositions and formulations comprising other salts of the compound of Formula I.

As discussed above, other salts of the compound of Formula I include mono-mesylate salts. Thus, in certain embodiments, the pharmaceutically acceptable salt of the compound of Formula I, or a hydrate thereof, is a mono-mesylate salt of a compound of Formula I, or a hydrate thereof. In one variation, the mono-mesylate salt is represented by Formula IIA:

(IIA)

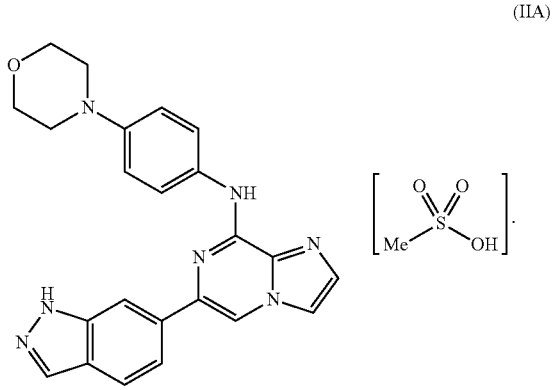

One of skill in the art would understand that when the mono-mesylate salt of the compound of Formula I is depicted as Formula IIA above, the ionic form (e.g., the cationic form of the compound of Formula I and the anionic form of the methanesulfonic acid) is intended.

Hydrates Thereof

In some embodiments, the pharmaceutically acceptable salt of the compound of Formula I, or a hydrate thereof, is a hydrate, mesylate salt of a compound of Formula I. In certain embodiments, the pharmaceutically acceptable salt of the compound of Formula I, or a hydrate thereof, is a monohydrate, mesylate salt of a compound of Formula I. In other embodiments, the pharmaceutically acceptable salt of the compound of Formula I, or a hydrate thereof, is a hydrate, bis-mesylate salt of a compound of Formula I. In one embodiment, the pharmaceutically acceptable salt of the compound of Formula I, or a hydrate thereof, is a monohydrate, bis-mesylate salt of a compound of Formula I.

Polymorphs Thereof

In some embodiments, the composition (including, for example, the pharmaceutical composition) comprises a polymorphic form of the pharmaceutically acceptable salt of the compound of Formula I, or a hydrate thereof. In certain embodiments, the polymorphic form is a polymorph of a bis-mesylate salt of the compound of Formula I, or a hydrate thereof, or any mixtures of polymorphic forms of the bis-mesylate salt of the compound of Formula I, or hydrates thereof. In any of the foregoing embodiments, the bis-mesylate salt of the compound of Formula I may be represented by Formula IA and IB; and a hydrate of the bis-mesylate salt of the compound of Formula I may be represented by Formula IC and ID.

In certain embodiments, polymorphic forms of the bis-mesylate salt of the compound of Formula I, or a hydrate thereof, suitable for use in the compositions (including without limitation the pharmaceutical compositions), methods of making and using such compositions, kits, unit dosage forms and articles of manufacture provided herein include: (i) polymorph Form 3, which is a polymorph of a monohydrate, bis-mesylate salt of a compound of Formula I, (ii) polymorph Form 7, which is a polymorph of a hydrate of a bis-mesylate salt of the compound of Formula I, and (iii) any combinations thereof. Polymorph Form 3 and polymorph Form 7 are described in further detail below.

Form 3

In some aspects, the compositions (including without limitation the pharmaceutical compositions), methods of making and using such compositions, kits, unit dosage forms and articles of manufacture provided herein comprise polymorph Form 3, which is a polymorph of a monohydrate, bis-mesylate salt of a compound of Formula I.

Throughout the present disclosure, it is understood that reference to "polymorph Form 3", "Form 3", "Form III", "bis-MSA salt of polymorph Form 3", or "bis-MSA salt Form 3" refers to the polymorph Form 3, which is a polymorph of a monohydrate, bis-mesylate salt of the compound of Formula I. As discussed above, the bis-mesylate salt may be depicted in various ways, including as a compound of Formula IA or IB. Furthermore, the monohydrate, bis-mesylate salt may be depicted by Formula IC or ID (wherein y is 1) or IE (wherein y is 1).

Figure 1B:
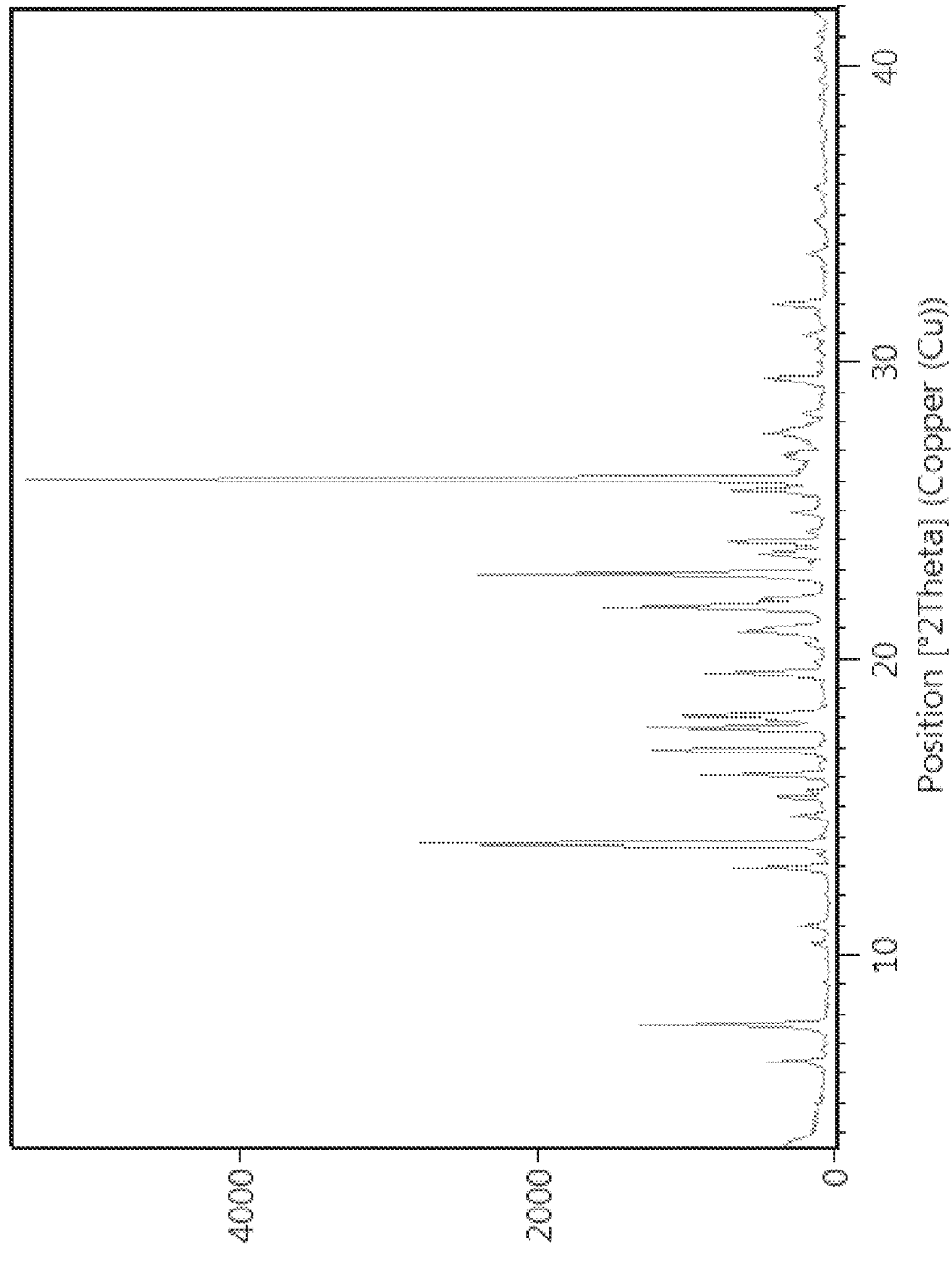

In some variations, polymorph Form 3 is characterized by or has an X-ray powder diffraction (XRPD) pattern substantially as shown in FIG. 1A or 1B. It should be understood, however, that relative intensities and assignments of the peaks of polymorphic forms depicted in the figures can vary depending on a number of factors, including sample preparation, mounting, and the instrument and analytical procedure and settings used to obtain the spectrum. As such, the peak observed in the figures and assignments listed herein (including in FIGS. 1A and 1B for polymorph Form 3) are intended to encompass variations of plus or minus 0.2 degrees 2θ.

In other variations, polymorph Form 3 is also characterized by or has an X-ray diffraction (XRPD) pattern comprising 2θ-reflections (±0.2 degrees): 13.8, 16.9, 22.9, and 26.1. In some embodiments, polymorph Form 3 is characterized by or has an X-ray diffraction (XRPD) pattern comprising at least one or more; at least two or more; or at least three or more of the 2θ-reflections (±0.2 degrees): 13.8, 16.9, 22.9, and 26.1. In some embodiments, polymorph Form 3 is characterized by or has an X-ray diffraction comprising 2θ-reflections (±0.2 degrees): 7.7, 12.9, 17.7, and 18.1. In some embodiments, polymorph Form 3 is characterized by or has an X-ray diffraction pattern comprising 2θ-reflections (±0.2 degrees) at 7.7, 12.9, 13.8, 16.9, 17.7, 18.1, 22.9, and 26.1. In some embodiments, polymorph Form 3 is characterized by or has an X-ray diffraction (XRPD) pattern comprising at least three or more; at least four or more; or at least five or more of the 2θ-reflections (±0.2 degrees): 7.7, 12.9, 13.8, 16.9, 17.7, 18.1, 22.9, and 26.1. When describing the 2θ-reflections in the X-ray diffraction pattern (e.g., of Form 3), it should be understood that ±0.2 degrees can also be expressed as "plus or minus 0.2 degrees 2θ".

In certain variations, polymorph Form 3 may also have one or more, two or more, three or more, four or more, five or more, or all of the following properties (i)-(vi):

(i) a unit cell as determined by crystal X-ray crystallography of the following dimensions: a=8.7831(6) Å; b=11.8484 (8) Å; c=14.2485(10) Å; α=98.108(6)°; β=100.955(6)°; and γ=98.861(6)°;

(ii) a triclinic crystal system;
(iii) a P-1 space group;
(iv) a volume of 1416.05(17) Å$^3$;
(v) a Z-value of 2; and
(vi) a density of 1.458 Mg/m$^3$.

Form 7

In some aspects, the compositions (including without limitation the pharmaceutical compositions), methods of making and using such compositions, kits, unit dosage forms and articles of manufacture provided herein comprise polymorph Form 7, which is a polymorph of a hydrate, bis-mesylate salt a compound of Formula I.

Throughout the application it is understood that reference to "polymorph Form 7", "Form 7", "Form VII", "bis-MSA salt of polymorph Form 7", or "bis-MSA salt Form 7" refers to the polymorph Form 7, which is a polymorph of a hydrate, bis-mesylate salt of a compound of Formula I. As discussed above, a bis-mesylate salt may be depicted in various ways, including as a compound of Formula IA or IB. Furthermore, a bis-mesylate salt having varying water content may be depicted by Formula ID.

In some variations, polymorph Form 7 is characterized by or has an X-ray diffraction (XRPD) pattern comprising 2θ-reflections (±0.2 degrees) at 4.9 and 9.8, and 2θ-reflections (±0.4 degrees) at 26.7. In certain variations, polymorph Form 7 is characterized by or has an X-ray diffraction (XRPD) pattern comprising 2θ-reflections (±0.2 degrees) at 4.9 and 9.8, and 2θ-reflections (±0.3 degrees) at 26.7. In certain variations, polymorph Form 7 is characterized by or has an X-ray diffraction (XRPD) pattern comprising 2θ-reflections (±0.2 degrees): 4.9, 9.8, and 26.7.

In some variations, polymorph Form 7 is characterized by or has an X-ray diffraction (XRPD) pattern comprising at least one or more; or at least two or more of 2θ-reflections at 4.9 (±0.2 degrees), 9.8 (±0.2 degrees), and 26.7 (±0.4 degrees). In some variations, polymorph Form 7 is characterized by or has an X-ray diffraction (XRPD) pattern comprising at least one or more; or at least two or more of 2θ-reflections at 4.9 (±0.2 degrees), 9.8 (±0.2 degrees), and 26.7 (±0.3 degrees). In certain variations, polymorph Form 7 is characterized by or has an X-ray diffraction (XRPD) pattern comprising at least one or more; or at least two or more of 2θ-reflections (±0.2 degrees): 4.9, 9.8, and 26.7.

In other embodiments, polymorph Form 7 is characterized by or has an X-ray diffraction pattern comprising 2θ-reflections (±0.2 degrees): 15.0 and 18.0. In some embodiments, polymorph Form 7 is characterized by or has an X-ray diffraction pattern comprising 2θ-reflections (±0.2 degrees) at 4.9, 9.8, 15.0 and 18.0, and 2θ-reflections (±0.4 degrees) at 26.7. In some embodiments, polymorph Form 7 is characterized by or has an X-ray diffraction pattern comprising 2θ-reflections (±0.2 degrees) at 4.9, 9.8, 15.0 and 18.0, and 2θ-reflections (±0.3 degrees) at 26.7. In some embodiments, polymorph Form 7 is characterized by or has an X-ray diffraction pattern comprising 2θ-reflections (±0.2 degrees) at 4.9, 9.8, 15.0, 18.0, and 26.7.

In other embodiments, polymorph Form 7 is characterized by or has an X-ray diffraction (XRPD) pattern comprising at least three or more; at least four or more; or each of the 2θ-reflections at 4.9 (±0.2 degrees), 9.8 (±0.2 degrees), 15.0 (±0.2 degrees), 18.0 (±0.2 degrees), and 26.7 (±0.4 degrees). In some embodiments, polymorph Form 7 is characterized by or has an X-ray diffraction (XRPD) pattern comprising at least three or more; at least four or more; or each of the 2θ-reflections at 4.9 (±0.2 degrees), 9.8 (±0.2 degrees), 15.0 (±0.2 degrees), 18.0 (±0.2 degrees), and 26.7 (±0.3 degrees). In some embodiments, polymorph Form 7 is characterized by or has an X-ray diffraction (XRPD) pattern comprising at least three or more; at least four or more; or each of the 2θ-reflections (±0.2 degrees) at 4.9, 9.8, 15.0, 18.0, and 26.7.

When describing the 2θ-reflections in the X-ray diffraction pattern (e.g., of Form 7), it should be understood that ±0.2 degrees, ±0.3 degrees, and ±0.4 degrees can also be expressed as "plus or minus 0.2 degrees 2θ", "plus or minus 0.3 degrees 2θ", and "plus or minus 0.4 degrees 2θ", respectively.

In other embodiments, polymorph Form 7 is a variable hydrate of a bis-mesylate salt of a compound of Formula I. A variable hydrate may have varying water content. For example, in one embodiment, polymorph Form 7 is a polymorph of a bis-mesylate salt having between 1.8% to 10% water. Various factors may affect the water content of polymorph Form 7, including, for example, the relative humidity conditions at which polymorph Form 7 is characterized.

Figure 1C:
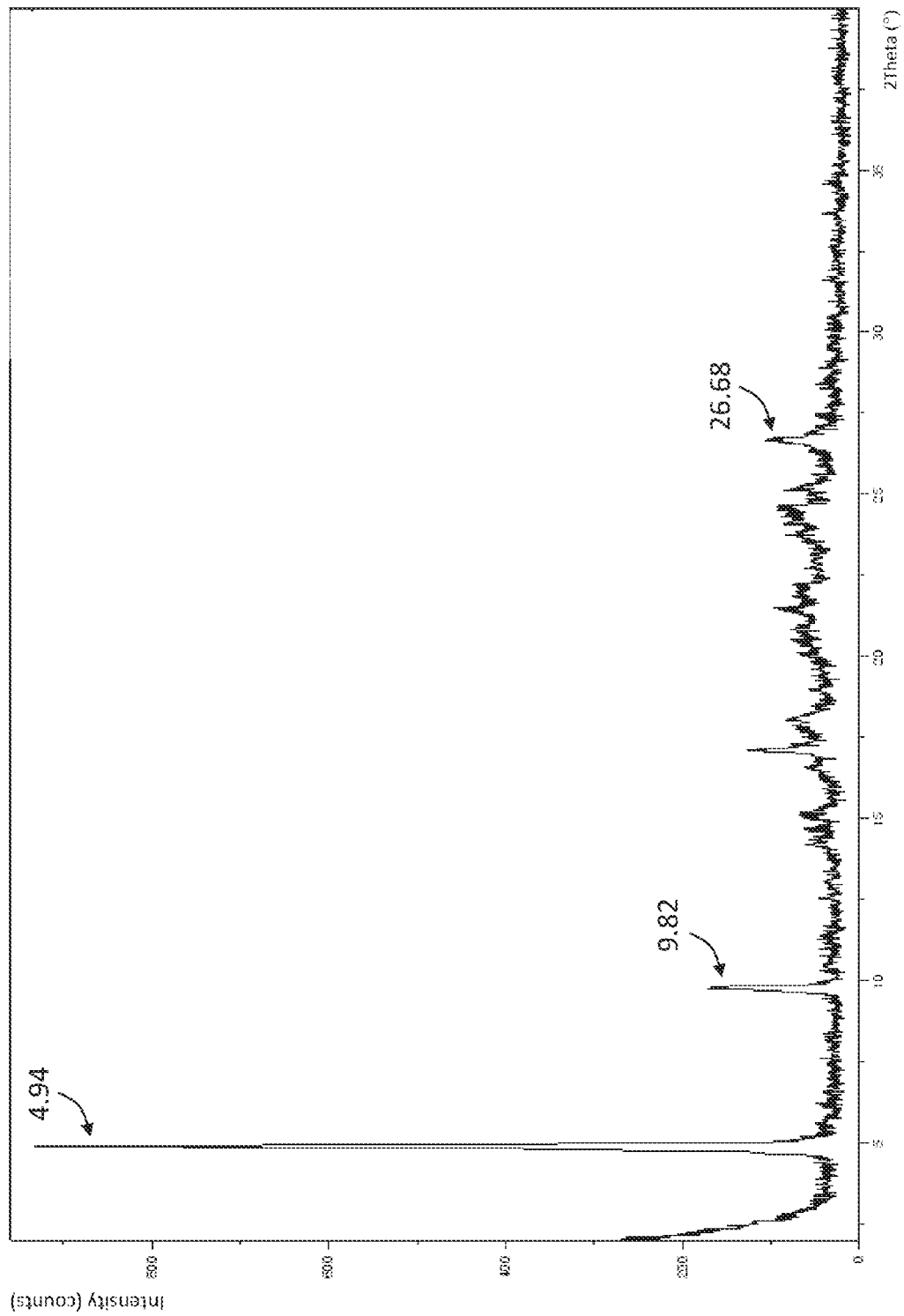

In some variations, polymorph Form 7 is also characterized by or has an XRPD pattern substantially as shown in FIG. 1C or 1D. It should be understood, however, that relative intensities and assignments of the peaks of polymorphic forms depicted in the figures can vary depending on a number of factors, including sample preparation, mounting, and the instrument and analytical procedure and settings used to obtain the spectrum. As such, the peak observed in the figures and assignments listed herein (including in FIGS. 1C and 1D for polymorph Form 7) are intended to encompass variations of plus or minus 0.2 degrees N. Further, in certain instances, the XRPD pattern of polymorph Form 7 may be moisture-dependent or vary based on the relative humidity at which Form 7 is characterized. For example, the XRPD in FIG. 1D was obtained at 25° C. and 53% relative humidity (RH).

In some embodiments, the term "substantially as shown in" when referring to an X-ray powder diffraction pattern means that a pattern that is not necessarily identical to those depicted herein, but that falls within the limits of experimental error or deviations, when considered by one of ordinary skill in the art, is encompassed.

In some embodiments, at least about 50%, at least about 60%, at least about 70%, at least about 80%, about 85%, about 90%, about 95%, about 96%, about 97%, about 98%, or about 99% of the composition (e.g., the pharmaceutical composition) is Form 3 as described above, Form 7 as described above, or a mixture thereof. In certain embodiments, at least about 50%, at least about 60%, at least about 70%, at least about 80%, about 85%, about 90%, about 95%, about 96%, about 97%, about 98%, or about 99% of the pharmaceutical composition is Form 3 as described above.

In other embodiments, less than about 50%, less than about 40%, less than about 30%, less than about 20%, about 15%, about 10%, about 5%, about 4%, about 3%, about 2%, or about 1% of the compound of Formula I present in the pharmaceutical composition of the compound of Formula I is other than polymorph Form 3 as described above, Form 7 as described above, or a mixture thereof. In certain embodiments, less than about 50%, less than about 40%, less than about 30%, less than about 20%, about 15%, about 10%, about 5%, about 4%, about 3%, about 2%, or about 1% of the compound of Formula I present in the pharmaceutical composition is other than polymorph Form 3 as described above.

In certain aspects, provided is a stable pharmaceutical composition comprising at least one polymorph of a pharmaceutically acceptable salt of the compound of Formula I, or a hydrate thereof, and at least one pharmaceutically acceptable carrier. In some embodiments, provided is a stable pharmaceutical composition comprising a polymorph of a pharmaceutically acceptable salt of the compound of Formula I, and at least one pharmaceutically acceptable carrier. In one variation, provided is a stable pharmaceutical composition comprising Form 3 (which is a polymorph of a monohydrate, bis-mesylate salt of Formula IA), and at least one pharmaceutically acceptable carrier.

The term "stable" refers to a pharmaceutical composition that remains substantially unchanged or substantially unaltered under conditions of manufacture and storage over a period of time under specific conditions. In one aspect, the pharmaceutical composition remains substantially unchanged or unaltered when kept at a temperature of about 65° C. or less, about 60° C. or less, about 50° C., about 40° C., about 30° C. or less, at about 25° C. or less, at about 15° C. or less, at about 5° C. or less, for at least one week, at least two weeks, at least three weeks or at least four weeks. For example, in one variation, a stable pharmaceutical composition remains substantially unchanged or unaltered (chemically and/or physically) when kept at a temperature of 40° C., 25° C., or 5° C., with relative humidity values of 75% or 60% for at least one or two or three or four weeks.

The pharmaceutically acceptable salt of the compound of Formula I, or a hydrate thereof, can be crystalline or non-crystalline, or can exhibit short-range order as in a semi-crystalline solid. The crystallinity of the salt, or hydrate thereof, in the compositions (e.g., the pharmaceutical compositions and formulations) may depend on the method of formulation and processing (e.g., incorporation of the salt, or hydrate thereof, by spray drying and/or dry granulation).

Crystalline Salt

In some embodiments of the compositions (including without limitation the pharmaceutical compositions), methods of making and using such compositions, kits, unit dosage forms and articles of manufacture provided herein, the pharmaceutically acceptable salt of a compound of Formula I, or a hydrate thereof, is crystalline. In a variation of the foregoing embodiment, the pharmaceutically acceptable salt of a compound of Formula I, or a hydrate thereof, may be: (i) a mesylate salt of a compound of Formula I, or a hydrate thereof; or (ii) a bis-mesylate salt of a compound of Formula I, or a hydrate thereof; (iii) a hydrate, bis-mesylate salt of a compound of Formula I; or (iv) a monohydrate bis-mesylate salt of a compound of Formula I, wherein the pharmaceutically acceptable salt, or a hydrate thereof, in each variation is crystalline. For example, a crystalline salt as described in the foregoing embodiments may be present in a tablet prepared by formulating polymorph Form 3 as a granulation.

The term "crystalline", in one variation, refers to a solid phase in which the material has a regular ordered internal structure at the molecular level and gives a distinctive X-ray diffraction pattern with defined peaks. The term "crystalline", in another variation, may also refer to a state in which the material exhibits long range order at the molecular level and gives a distinctive X-ray diffraction pattern with defined peaks. Such materials when heated sufficiently will also exhibit the properties of a liquid, but the change from solid to liquid is characterized by a phase change, typically first order (melting point).

In certain embodiments, the pharmaceutically acceptable salt of the compound of Formula I, or a hydrate thereof, is substantially crystalline. In a variation of the foregoing embodiment, the pharmaceutically acceptable salt of a compound of Formula I, or a hydrate thereof, may be: (i) a mesylate salt of a compound of Formula I, or a hydrate thereof; or (ii) a bis-mesylate salt of a compound of Formula I, or a hydrate thereof; (iii) a hydrate, bis-mesylate salt of a compound of Formula I; or (iv) a monohydrate bis-mesylate salt of a compound of Formula I, wherein the pharmaceutically acceptable salt, or a hydrate thereof, in each variation of the composition is substantially crystalline.

In some embodiments, a compound (e.g., a pharmaceutically acceptable salt or a hydrate thereof) that is substantially crystalline has greater than 50%; or greater than 55%; or greater than 60%; or greater than 65%; or greater than 70%; or greater than 75%; or greater than 80%; or greater than 85%; or greater than 90%; or greater than 95%, or greater than 99% of the compound (e.g., a pharmaceutically acceptable salt or a hydrate thereof) present in a composition in crystalline form. In other embodiments, a compound (e.g., a pharmaceutically acceptable salt or a hydrate thereof) that is substantially crystalline has no more than about 20%, or no more than about 10%, or no more than about 5%, or no more than about 2% of the compound in non-crystalline form. In other embodiments, a compound (e.g., a pharmaceutically acceptable salt or a hydrate thereof) that is substantially crystalline has no more than about 20%, or no more than about 10%, or no more than about 5%, or no more than about 2% of the compound in amorphous form.

Non-Crystalline

In other embodiments of the compositions (including without limitation the pharmaceutical compositions), methods of making and using such compositions, kits, unit dosage forms and articles of manufacture provided herein, the pharmaceutically acceptable salt of a compound of Formula I is non-crystalline. In a variation of the foregoing embodiment, the pharmaceutically acceptable salt of a compound of Formula I, may be: (i) a mesylate salt of a compound of Formula I; or (ii) a bis-mesylate salt of a compound of Formula I, wherein the pharmaceutically acceptable salt in each variation is crystalline. For example, a non-crystalline salt as described in the foregoing embodiments may be present in a spray-dried powder prepared from a compound of Formula I, or a pharmaceutically acceptable salt thereof, or hydrate thereof.

The term "non-crystalline" refers to a state in which the material lacks long range order at the molecular level. One of skill in the art would recognize that such materials do not typically exhibit sharp peaks in their X-ray diffraction patterns.

In some embodiments, the pharmaceutically acceptable salt of a compound of Formula I or hydrate thereof (including, for example, a bis-mesylate salt of Formula IA) formulated as a solid dispersion formulation (as discussed in further detail below) is substantially non-crystalline. In certain embodiment, a compound, or a pharmaceutically acceptable salt thereof, or hydrate thereof, that is substantially non-crystalline has greater than 50%; or greater than 55%; or greater than 60%; or greater than 65%; or greater than 70%; or greater than 75%; or greater than 80%; or greater than 85%; or greater than 90%; or greater than 95%, or greater than 99% of the compound, or a pharmaceutically acceptable salt thereof, present in a composition in non-crystalline form. In other embodiments, a compound, or a pharmaceutically acceptable salt thereof, or hydrate thereof, that is substantially non-crystalline has no more than about 20% crystallinity, or no more than about 10% crystallinity, or no more than about 5% crystallinity, or no more than about 2% crystallinity.

Amorphous

In some embodiments of the pharmaceutical composition, the pharmaceutically acceptable salt of the compound of Formula I, or a pharmaceutically acceptable salt thereof, or hydrate thereof, may be amorphous. In certain embodiments, the bis-mesylate salt of Formula IA may be amorphous.

The term "amorphous" refers to a state in which the material lacks order (e.g., long range order) at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order (e.g., glass transition).

For example, in one embodiment, the pharmaceutically acceptable salt of a compound of Formula I or hydrate thereof (including, for example, a bis-mesylate salt of Formula IA) formulated as a solid dispersion formulation (as discussed in further detail below) is substantially amorphous. In some embodiments, a compound that is substantially amorphous has greater than 50%; or greater than 55%; or greater than 60%; or greater than 65%; or greater than 70%; or greater than 75%; or greater than 80%; or greater than 85%; or greater than 90%; or greater than 95%, or greater than 99% of the compound present in a composition in amorphous form. In other embodiments, a compound that is substantially amorphous has no more than about 20% crystallinity, or no more than about 10% crystallinity, or no more than about 5% crystallinity, or no more than about 2% crystallinity.

Deuterated Compounds

Any formula or structure given herein, including a compound of Formula I and pharmaceutically acceptable salts thereof (including, for example, the mono-mesylate and the bis-mesylate salts), or a hydrate thereof, is also contemplated as an isotopically labeled form of the compounds, or salts, or hydrates thereof. Thus, although the unlabeled forms of compounds are provided, it is understood that the present disclosure also contemplates isotopically labeled compounds, even though such isotopes are not explicitly depicted. Isotopically labeled compounds, or salts, or hydrates thereof have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^{2}H$ (deuterium, D), $^{3}H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. For instance, isotopes of hydrogen, carbon, nitrogen, oxygen, phosphorous, fluorine and chlorine, such as, but not limited to $^{2}H$ (deuterium, D), $^{3}H$ (tritium), $^{11}C$, $^{13}C$, $^{14}C$, $^{15}N$, and $^{35}S$ may be incorporated into a compound of formula I, including a salt (e.g. a mesylate salt) of a compound of formula I, or a hydrate thereof. Various isotopically labeled compounds, or salts, or hydrates thereof of the present disclosure, for example those into which radioactive isotopes such as $^{3}H$, $^{13}C$ and $^{14}C$ are incorporated. Such isotopically labeled compounds or salts thereof may be useful in metabolic studies, reaction kinetic studies, detection or imaging techniques, such as positron emission tomography (PET) or single-photon emission computed tomography (SPECT) including drug or substrate tissue distribution assays or in radioactive treatment of subjects.

The disclosure also includes a compound of Formula I and pharmaceutically acceptable salts thereof (including, for example, the mono-mesylate and the bis-mesylate salts), or a hydrate thereof, in which from 1 to n hydrogens attached to a carbon atom is/are replaced by deuterium, in which n is the number of hydrogens in the molecule. Such compounds may exhibit increased resistance to metabolism and are thus useful for increasing the half life of a compound of Formula I, or pharmaceutically acceptable salts thereof, or hydrates thereof (including a bis-mesylate salt of Formula IA or IB, or a hydrate thereof; or a hydrate, bis-mesylate of Formula IC or ID) when administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

Deuterium labeled or substituted therapeutic compounds of the disclosure (including salts or hydrates thereof) may have improved DMPK (drug metabolism and pharmacokinetics) properties, relating to absorption, distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I and pharmaceutically acceptable salts thereof (including, for example, the mono-mesylate and the bis-mesylate salts), or hydrates thereof.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds or salts thereof of this disclosure any atom specifically designated as a deuterium (D) is meant to represent deuterium.

Pharmaceutically Acceptable Carriers

The term "carrier" refers to diluents, disintegrants, precipitation inhibitors, surfactants, glidants, binders, lubricants, and other excipients and vehicles with which the compound is administered. Carriers are generally described herein and also in "Remington's Pharmaceutical Sciences" by E.W. Martin. Examples of carriers include, but are not limited to, aluminum monostearate, aluminum stearate, carboxymethylcellulose, carboxymethylcellulose sodium, crospovidone, glyceryl isostearate, glyceryl monostearate, hydroxyethylcellulose, hydroxymethylcellulose, hydroxyoctacosanyl hydroxystearate, hydroxypropylcellulose, hydroxypropylmethylcellulose, lactose, lactose monohydrate, magnesium stearate, mannitol, microcrystalline cellulose, poloxamer 124, poloxamer 181, poloxamer 182, poloxamer 188, poloxamer 237, poloxamer 407, povidone, silicon dioxide, colloidal silicon dioxide, silicone, silicone adhesive 4102, and silicone emulsion. In some embodiments, the compositions (e.g., pharmaceutical compositions) provided herein comprise carriers selected from aluminum monostearate, aluminum stearate, carboxymethylcellulose, carboxymethylcellulose sodium, crospovidone, glyceryl isostearate, glyceryl monostearate, hydroxyethylcellulose, hydroxymethylcellulose, hydroxyoctacosanyl hydroxystearate, hydroxypropylcellulose, hydroxypropylmethylcellulose, lactose, lactose monohydrate, magnesium stearate, mannitol, microcrystalline cellulose, poloxamer 124, poloxamer 181, poloxamer 182, poloxamer 188, poloxamer 237, poloxamer 407, povidone, silicon dioxide, and colloidal silicon dioxide. It should be understood, however, that the carriers selected for the pharmaceutical compositions provided in the present disclosure, and the amounts of such carriers in the composition, may vary depending on the method of formulation and processing (e.g., incorporation by spray drying and/or dry granulation).

The term "diluent" generally refers to a substance that is used to dilute the compound of interest prior to delivery. Diluents can also serve to stabilize compounds. Examples of diluents may include starch, saccharides, disaccharides, sucrose, lactose, polysaccharides, cellulose, cellulose ethers, hydroxypropylcellulose, sugar alcohols, xylitol, sorbitol, maltitol, microcrystalline cellulose, calcium or sodium carbonate, lactose, lactose monohydrate, dicalcium phosphate, cellulose, compressible sugars, dibasic calcium phosphate dehydrate, mannitol, microcrystalline cellulose, and tribasic calcium phosphate.

The term "disintegrant" generally refers to a substance which, upon addition to a solid preparation, facilitates its break-up or disintegration after administration and permits the release of an active ingredient as efficiently as possible to allow for its rapid dissolution. Examples of disintegrants may include maize starch, sodium starch glycolate, croscarmellose sodium, crospovidone, microcrystalline cellulose, modified corn starch, sodium carboxymethyl starch, povidone, pregelatinized starch, and alginic acid.

The term "precipitation inhibitors" generally refers to a substance that prevents or inhibits precipitation of the active agent from a supersaturated solution. One example of a precipitation inhibitor is hydroxypropylmethylcellulose (HPMC).

The term "surfactants" generally refers to a substance that lowers the surface tension between a liquid and a solid, and could improve the wetting of the active agent or improve the solubility of the active agent. Examples of surfactants include poloxamer and sodium lauryl sulfate.

The term "glidant" generally refers to substances used in tablet and capsule formulations to improve flow-properties during tablet compression and to produce an anti-caking effect. Examples of glidants may include colloidal silicon dioxide, talc, fumed silica, starch, starch derivatives, and bentonite.

The term "binder" generally refers to any pharmaceutically acceptable substance (such as any pharmaceutically acceptable film) that can be used to bind together the active and inert components of the carrier to maintain cohesive and discrete portions. Examples of binders may include hydroxypropylcellulose, hydroxypropylmethylcellulose, povidone, copovidone, and ethyl cellulose.

The term "lubricant" generally refers to a substance that is added to a powder blend to prevent the compacted powder mass from sticking to the equipment during the tableting or encapsulation process. A lubricant can aid the ejection of the tablet form the dies, and can improve powder flow. Examples of lubricants may include magnesium stearate, stearic acid, silica, fats, calcium stearate, polyethylene glycol, sodium stearyl fumarate, or talc; and solubilizers such as fatty acids including lauric acid, oleic acid, and $C_8/C_{10}$ fatty acid.

In certain aspects, provided is a composition comprising at least one active agent (including, for example, a compound of Formula I, or a pharmaceutically acceptable salt thereof, or a hydrate thereof), and one or more of (a)-(g) below:
 a) at least one diluent;
 b) at least one disintegrant;
 c) at least one precipitation inhibitor;
 d) at least one surfactant;
 e) at least one glidant;
 f) at least one lubricant; and
 g) at least one binder.
It should be understood that a pharmaceutically acceptable carrier may be characterized by two or more the categories set forth in (a)-(g). For example, hydroxypropylmethylcellulose may be characterized as a precipitation inhibitor and a binder.

In one variation, provided is a pharmaceutical composition comprising at least one active agent (including, for example, a compound of Formula I, or a pharmaceutically acceptable salt thereof, or a hydrate thereof), and one or more of (a)-(f) below:
 a) at least one diluent;
 b) at least one disintegrant;
 c) at least one precipitation inhibitor;
 d) at least one surfactant;
 e) at least one glidant; and
 f) at least one lubricant.

In some embodiments, the pharmaceutical composition comprises two of (a)-(f) above, or three of (a)-(f) above, or four of (a)-(f) above, or five of (a)-(f) above, or all of (a)-(f) above.

In some embodiments, the pharmaceutical composition comprises at least one or at least two diluent(s). In one variation, the pharmaceutical composition comprises at least one diluent. In certain embodiments, the pharmaceutical composition comprises one or two diluent(s). In certain embodiments, the diluent is selected from the group consisting of mannitol, microcrystalline cellulose, lactose, dextrose, sucrose, ludiflash, F-melt, advantose, GalenIQ, and any mixtures thereof. In one embodiment, the diluent is mannitol, microcrystalline cellulose, or a mixture thereof. In one variation, the pharmaceutical composition comprises one or more diluents, and any one or more of (b)-(f) above.

In some embodiments, the pharmaceutical composition comprises at least one disintegrant. In certain embodiments, the pharmaceutical composition comprises only one disintegrant. In one embodiment, the disintegrant is croscarmellose sodium. In another embodiment, the disintegrant is crospovidone. In one variation, the pharmaceutical composition comprises one or more disintegrants, and any one or more of (a), (c)-(f) above.

In some embodiments, the pharmaceutical composition comprises at least one precipitation inhibitor. In certain embodiments, the pharmaceutical composition comprises one precipitation inhibitor. In one embodiment, the precipitation inhibitor is hydroxypropylmethylcellulose. In one variation, the pharmaceutical composition comprises at least one precipitation inhibitor, and at least one diluent; for example, hydroxypropylmethylcellulose and mannitol.

In some embodiments, the pharmaceutical composition comprises at least one surfactant. In certain embodiments, the pharmaceutical composition comprises only one surfactant. In one embodiment, the surfactant is poloxamer. In another embodiment, the surfactant is sodium lauryl sulfate.

In some embodiments, the pharmaceutical composition comprises at least one glidant. In certain embodiments, the pharmaceutical composition comprises only one glidant. In one embodiment, the glidant is colloidal silicon dioxide.

In some embodiments, the pharmaceutical composition comprises at least one lubricant. In certain embodiments, the pharmaceutical composition comprises only one lubricant. In one embodiment, the lubricant is magnesium stearate.

It should be understood that the composition (e.g., pharmaceutical composition) comprises pharmaceutically acceptable carriers detailed herein, the same as if each and every combination of pharmaceutically acceptable carrier were specifically and individually listed.

For example, in some variations, the pharmaceutical composition comprises a pharmaceutically acceptable salt of the compound of Formula I, or a hydrate thereof, and at least one precipitation inhibitor. In one variation, the pharmaceutical composition comprises a mesylate salt of a compound of Formula I, or a hydrate thereof, and at least one precipitation inhibitor. In another variation, the pharmaceutical composition comprises a mesylate salt of a compound of Formula I, or a hydrate thereof, at least one precipitation inhibitor, and at least one diluent. In another variation, the pharmaceutical composition comprises a mesylate salt of a compound of Formula I, or a hydrate thereof, at least one precipitation inhibitor, and at least one disintegrant. In another variation, the pharmaceutical composition comprises a mesylate salt of a compound of Formula I, or a hydrate thereof, at least one precipitation inhibitor, and at least one surfactant. In another variation, the pharmaceutical composition comprises a mesylate salt of a compound of Formula I, or a hydrate thereof, at least one precipitation inhibitor, and at least one glidant. In another variation, the pharmaceutical composition comprises a mesylate salt of a compound of Formula I, or a hydrate thereof, at least one precipitation inhibitor, and at least one lubricant. In another variation, the pharmaceutical composition comprises a mesylate salt of a compound of Formula I, or a hydrate thereof, at least one precipitation inhibitor, at least one diluent, and at least surfactant.

In any of the foregoing variations, the mesylate salt of the compound of Formula I, or a hydrate thereof, may be a mono-mesylate salt of the compound of Formula I, or a hydrate thereof; or a bis-mesylate salt of the compound of Formula I, or a hydrate thereof; or a hydrate, bis-mesylate salt of the compound of Formula I; or a monohydrate, bis-mesylate salt of the compound of Formula I; or polymorph Form 3, polymorph Form 7, or a combination thereof.

In some embodiments, the composition comprises a pharmaceutically acceptable salt of the compound of Formula I, or a hydrate thereof, hydroxypropylmethylcellulose, and at least one additional carrier. In one variation, the composition comprises a pharmaceutically acceptable salt of the compound of Formula I, or a hydrate thereof, hydroxypropylmethylcellulose, and at least one diluent. In another variation, the composition comprises a pharmaceutically acceptable salt of the compound of Formula I, or a hydrate thereof, hydroxypropylmethylcellulose, and at least one disintegrant. In another variation, the composition comprises a pharmaceutically acceptable salt of the compound of Formula I, or a hydrate thereof, hydroxypropylmethylcellulose, and at least one surfactant. In another variation, the composition comprises a pharmaceutically acceptable salt of the compound of Formula I, or a hydrate thereof, hydroxypropylmethylcellulose, and at least one glidant. In another variation, the composition comprises a pharmaceutically acceptable salt of the compound of Formula I, or a hydrate thereof, hydroxypropylmethylcellulose, and at least one lubricant. In another variation, the composition comprises a pharmaceutically acceptable salt of the compound of Formula I, or a hydrate thereof, hydroxypropylmethylcellulose, at least one diluent, and at least surfactant. In any embodiment in which the composition comprises hydroxypropylmethylcellulose, in one variation the composition comprises a polymeric matrix formed from hydroxypropylmethylcellulose (e.g., a composition in which a pharmaceutically acceptable salt of the compound of Formula I, such as a bis-mesylate salt of the compound of Formula I, or a hydrate thereof, or polymorph Form 3, polymorph Form 7, or a combination thereof, is dispersed within a polymeric matrix formable from hydroxypropylmethylcellulose).

In any of the foregoing variations, the pharmaceutically acceptable salt of the compound of Formula I, or a hydrate thereof, may be a mesylate salt of the compound of Formula I; or a mono-mesylate salt of the compound of Formula I, or a hydrate thereof; or a bis-mesylate salt of the compound of Formula I, or a hydrate thereof; or a hydrate, bis-mesylate salt of the compound of Formula I; or a monohydrate, bis-mesylate salt of the compound of Formula I; or polymorph Form 3, polymorph Form 7, or a combination thereof.

In other variations, the pharmaceutical composition comprises a bis-mesylate salt of Formula IA, or a hydrate thereof, hydroxypropylmethylcellulose, and at least one additional carrier. In one variation, the pharmaceutical composition comprises a bis-mesylate salt of Formula IA, or a hydrate thereof, hydroxypropylmethylcellulose, and at least one diluent. In another variation, the pharmaceutical composition comprises a bis-mesylate salt of Formula IA, or a hydrate thereof, hydroxypropylmethylcellulose, and at least one disintegrant. In another variation, the pharmaceutical composition comprises a bis-mesylate salt of Formula IA, or a hydrate thereof, hydroxypropylmethylcellulose, and at least one surfactant. In another variation, the pharmaceutical composition comprises a bis-mesylate salt of Formula IA, or a hydrate thereof, hydroxypropylmethylcellulose, and at least one glidant. In another variation, the pharmaceutical composition comprises a bis-mesylate salt of Formula IA, or a hydrate thereof, hydroxypropylmethylcellulose, and at least one lubricant. In another variation, the pharmaceutical composition comprises a bis-mesylate salt of Formula IA, or a hydrate thereof, hydroxypropylmethylcellulose, at least one diluent, and at least surfactant. In any of the foregoing variations, the bis-mesylate salt of Formula IA, or a hydrate thereof, is polymorph Form 3, polymorph Form 7, or a combination thereof.

In other embodiments, the composition comprises a monohydrate, bis-mesylate salt of a compound of Formula I, hydroxypropylmethylcellulose, and mannitol. In another variation, the composition comprises a monohydrate, bis-mesylate salt of a compound of Formula I, hydroxypropylmethylcellulose, and crospovidone. In another variation, the composition comprises a monohydrate, bis-mesylate salt of a compound of Formula I, hydroxypropylmethylcellulose, and poloxamer. In another variation, the composition comprises a monohydrate, bis-mesylate salt of a compound of Formula I, hydroxypropylmethylcellulose, and colloidal silicon dioxide. In another variation, the composition comprises a monohydrate, bis-mesylate salt of a compound of Formula I, hydroxypropylmethylcellulose, and microcrystalline cellulose. In another variation, the composition comprises a monohydrate, bis-mesylate salt of a compound of Formula I, hydroxypropylmethylcellulose, and magnesium stearate. In yet another variation, the composition comprises a monohydrate, bis-mesylate salt of a compound of Formula I, hydroxypropylmethylcellulose, mannitol, and crospovidone. In yet another variation, the composition comprises a monohydrate, bis-mesylate salt of a compound of Formula I, hydroxypropylmethylcellulose, mannitol, crospovidone, and colloidal silicon dioxide. In yet another variation, the composition comprises a monohydrate, bis-mesylate salt of a compound of Formula I, hydroxypropylmethylcellulose, mannitol, crospovidone, colloidal silicon dioxide, and microcrystalline cellulose. In yet another variation, the composition comprises a monohydrate, bis-mesylate salt of a compound of Formula I, hydroxypropylmethylcellulose, mannitol, crospovidone, colloidal silicon dioxide, microcrystalline cellulose, and magnesium stearate. In any embodiment in which the composition comprises hydroxypropylmethylcellulose, in one variation the composition comprises a polymeric matrix formed from hydroxypropylmethylcellulose (e.g., a composition in which a pharmaceutically acceptable salt of a compound of Formula I, such as a bis-mesylate salt of a compound of Formula I, or a hydrate thereof (and any other pharmaceutically acceptable carrier) is dispersed within a polymeric matrix formable from hydroxypropylmethylcellulose).

In yet other variations, the pharmaceutical composition comprises Form 3, hydroxypropylmethylcellulose, and mannitol. In another variation, the pharmaceutical composition comprises Form 3, hydroxypropylmethylcellulose, and crospovidone. In another variation, the pharmaceutical composition comprises Form 3, hydroxypropylmethylcellulose, and poloxamer. In another variation, the pharmaceutical composition comprises Form 3, hydroxypropylmethylcellulose, and colloidal silicon dioxide. In another variation, the pharmaceutical composition comprises Form 3, hydroxypropylmethylcellulose, and microcrystalline cellulose. In another variation, the pharmaceutical composition comprises Form 3, hydroxypropylmethylcellulose, and magnesium stearate. In yet another variation, the pharmaceutical composition comprises Form 3, hydroxypropylmethylcellulose, mannitol, and crospovidone. In yet another variation, the pharmaceutical composition comprises Form 3, hydroxypropylmethylcellulose, mannitol, crospovidone, and colloidal silicon dioxide. In yet another variation, the pharmaceutical composition comprises Form 3, hydroxypropylmethylcellulose, mannitol, crospovidone, colloidal silicon dioxide, and microcrystalline cellulose. In yet another variation, the pharmaceutical composition comprises Form 3, hydroxypropylmethylcellulose, mannitol, crospovidone, colloidal silicon dioxide, microcrystalline cellulose, and magnesium stearate. It should be understood that Form 3 is a polymorph of a monohydrate, bis-mesylate salt of a compound of Formula I, which may also be described as a polymorph of a monohydrate, bis-mesylate salt of Formula IA, IB, IC, ID (where y is 1), or IE (where y is 1).

In certain variations, the composition comprises a mesylate salt of a compound of Formula I, or a hydrate thereof, and at least one pharmaceutically acceptable carrier selected from the group consisting of hydroxypropylmethylcellulose, mannitol, crospovidone, poloxamer, colloidal silicon dioxide, microcrystalline cellulose, magnesium stearate, and any mixtures thereof. In another variation, the composition comprises a mesylate salt of a compound of Formula I, or a hydrate thereof, hydroxypropylmethylcellulose, and at least one additionally pharmaceutically acceptable carrier selected from the group consisting of mannitol, crospovidone, poloxamer, colloidal silicon dioxide, microcrystalline cellulose, magnesium stearate, and any mixtures thereof.

In any of the foregoing variations, the mesylate salt of the compound of Formula I, or a hydrate thereof, may be a mono-mesylate salt of the compound of Formula I, or a hydrate thereof; or a bis-mesylate salt of the compound of Formula I, or a hydrate thereof; or a hydrate, bis-mesylate salt of the compound of Formula I; or a monohydrate, bis-mesylate salt of the compound of Formula I.

In certain variations, the pharmaceutical composition comprises a bis-mesylate salt of Formula IA (including, for example, Form 3), and at least one pharmaceutically acceptable carrier selected from the group consisting of hydroxypropylmethylcellulose, mannitol, crospovidone, poloxamer, colloidal silicon dioxide, microcrystalline cellulose, magnesium stearate, and any mixtures thereof. In another variation, the pharmaceutical composition comprises a bis-mesylate salt of Formula IA (including, for example, Form 3), hydroxypropylmethylcellulose, and at least one additionally pharmaceutically acceptable carrier selected from the group consisting of mannitol, crospovidone, poloxamer, colloidal silicon dioxide, microcrystalline cellulose, magnesium stearate, and any mixtures thereof.

It should also be understood that the pharmaceutically acceptable carriers described above may perform one or more different functions in a given formulation, and may fall within one or more functional classes of carriers (e.g., disintegrants, lubricants, diluents).

It should further be understood that, in other embodiments, the pharmaceutical composition may comprise one or more additional carriers to improve flow, compression, hardness, taste, and tablet performance.

Pharmaceutically Acceptable Polymers

While the pharmaceutically acceptable carriers used in the pharmaceutical compositions provided may be described functionally, the pharmaceutically acceptable carriers may also be described structurally. Thus, the pharmaceutically acceptable carriers in one aspect are pharmaceutically acceptable polymers.

Provided is a composition (e.g., pharmaceutical composition) comprising a mesylate salt of a compound of Formula I, or a hydrate thereof, and at least one, at least two, or at least three pharmaceutically acceptable polymer(s). In the foregoing embodiment, the mesylate salt of the compound of Formula I, or a hydrate thereof, may be a mono-mesylate salt of the compound of Formula I, or a hydrate thereof; or a bis-mesylate salt of the compound of Formula I, or a hydrate thereof; or a hydrate, bis-mesylate salt of the compound of Formula I; or a monohydrate, bis-mesylate salt of the compound of Formula I.

The term "polymer" refers to a chemical compound or mixture of compounds consisting of repeating structural units, which may be created through a process of polymerization. Suitable polymers useful in this invention are described throughout. The term "pharmaceutically acceptable polymer" refers to a polymer that does not have properties that would cause a reasonably prudent medical practitioner to avoid administration of the material to a subject (e.g., human), taking into consideration the disease or conditions to be treated and the respective route of administration.

In certain variations, the composition (e.g., pharmaceutical composition) comprises a mesylate salt of a compound of Formula I (including, for example, a mono-mesylate or bis-mesylate salt), and one, two, three, or four pharmaceutically acceptable polymer(s). In one variation, the composition (e.g., pharmaceutical composition) comprises a mesylate salt of a compound of Formula I (including, for example, a mono-mesylate or bis-mesylate salt), at least one pharmaceutically acceptable polymer, and at least one, at least two, or at least three additional pharmaceutically acceptable carrier(s). In other variations, the composition (e.g., pharmaceutical composition) comprises a mesylate salt of a compound of Formula I (including, for example, a mono-mesylate or bis-mesylate salt), one, two, three, or four pharmaceutically acceptable polymer(s), and at least one, at least two, or at least three additional pharmaceutically acceptable carrier(s).

In some embodiments of the composition (e.g., pharmaceutical composition), at least one of the pharmaceutically acceptable polymers is hydroxypropylmethylcellulose (also known in the art as HPMC or by other common names such as hypromellose). HPMC is commonly used in the art as a pharmaceutically acceptable carrier in sustained release formulations, and may also be used for immediate release formulations as described herein.

It should be understood by a skilled artisan that the active agent may be formulated for sustained release or immediate release. A "sustained release formulation" is a formulation which is designed to slowly release an active agent in the subject over an extended period of time, whereas an "immediate release formulation" is a formulation which is designed to quickly release an active agent in the subject over a shortened period of time. In some cases, the immediate release formulation may be coated such that the active agent is only released once it reached the desired target in the subject, for example, in the stomach.

In another embodiment of the pharmaceutical composition, a pharmaceutically acceptable salt of a compound of Formula I, or a hydrate thereof, is formulated for immediate release. In the foregoing embodiment, the pharmaceutically acceptable salt of the compound of Formula I, or a hydrate thereof, may be a mesylate salt of the compound of Formula I; or a mono-mesylate salt of the compound of Formula I, or a hydrate thereof; or a bis-mesylate salt of the compound of Formula I, or a hydrate thereof; or a hydrate, bis-mesylate salt of the compound of Formula I; or a monohydrate, bis-mesylate salt of the compound of Formula I.

The use of hydroxypropylmethylcellulose in such immediate release formulation was observed to increase bioavailability of the pharmaceutically acceptable salt of a compound of Formula I, or a hydrate thereof, administered to the subject (e.g., a human) compared to a formulation of a compound of Formula I without the use of hydroxypropylmethylcellulose. Thus, in some aspects, provided is a method of increasing bioavailability of a pharmaceutically acceptable salt of a compound of Formula I, or a hydrate thereof, comprising administering to a human in need thereof a composition comprising (i) a pharmaceutically acceptable salt of a compound of Formula I, or a hydrate thereof, and (ii) hydroxypropylmethylcellulose, to increase bioavailability of the pharmaceutically acceptable salt of a compound of Formula I, or a hydrate thereof. In one variation, bioavailability is increased in the human compared to administering to the human a composition comprising a pharmaceutically acceptable salt of a compound of Formula I, or a hydrate thereof, in which hydroxypropylmethylcellulose is absent. In some embodiments, the composition is a tablet.

In some variations of the foregoing methods of increasing bioavailability, the pharmaceutically acceptable salt of a compound of Formula I, or a hydrate thereof, is a bis-mesylate salt of a compound of Formula I; and in one variation, the pharmaceutically acceptable salt of a compound of Formula I, or a hydrate thereof, is a monohydrate, bis-mesylate salt of a compound of Formula I.

In some instances, hydroxypropylmethylcellulose was observed to prolong supersaturation of the pharmaceutically acceptable salt of a compound of Formula I (including, for example, a mesylate salt of a compound of Formula I), or a hydrate thereof. Thus, in some aspects, provided is a method of prolonging supersaturation of a pharmaceutically acceptable salt of a compound of Formula I, or a hydrate thereof, in a composition, comprising adding hydroxypropylmethylcellulose to a composition comprising a pharmaceutically acceptable salt of a compound of Formula I, or a hydrate thereof, to prolong supersaturation. In one variation, supersaturation of a compound of Formula I, or a hydrate thereof in the composition is prolonged compared to a composition comprising a pharmaceutically acceptable salt of a compound of Formula I, or a hydrate thereof, in which hydroxypropylmethylcellulose is absent.

In some variations of the foregoing methods to prolong supersaturation, the pharmaceutically acceptable salt of a compound of Formula I, or a hydrate thereof, is a bis-mesylate salt of a compound of Formula I; and in one variation, the pharmaceutically acceptable salt of a compound of Formula I, or a hydrate thereof, is a monohydrate, bis-mesylate salt of a compound of Formula I. In some embodiments, supersaturation is prolonged over an hour, which gives a compound of Formula I a longer window to be absorbed in vivo. In some embodiments, the composition is a feed solution for spray drying.

In other instances, hydroxypropylmethylcellulose was observed to minimize crystallization of the pharmaceutically acceptable salt of a compound of Formula I (including, for example, a mesylate salt of a compound of Formula I), or a hydrate thereof, when combined with the pharmaceutically acceptable salt of a compound of Formula I (including, for example, a mesylate salt of a compound of Formula I), or a hydrate thereof in a solid dispersion. Thus, in other aspects, provided is a method of minimizing crystallization of a pharmaceutically acceptable salt of a compound of Formula I, or a hydrate thereof, in a composition, comprising adding hydroxypropylmethylcellulose to a composition comprising a pharmaceutically acceptable salt of a compound of Formula I, or a hydrate thereof, to minimize crystallization compared to a composition comprising a pharmaceutically acceptable salt of a compound of Formula I, or a hydrate thereof, in which hydroxypropylmethylcellulose is absent. In one variation, crystallization of a compound of Formula I, or a hydrate thereof, in the composition is minimized compared to a composition comprising a pharmaceutically acceptable salt of a compound of Formula I, or a hydrate thereof, in which hydroxypropylmethylcellulose is absent.

In some variations of the foregoing methods to minimize crystallization, the pharmaceutically acceptable salt of a compound of Formula I, or a hydrate thereof, is a bis-mesylate salt of a compound of Formula I; and in one variation, the pharmaceutically acceptable salt of a compound of Formula I, or a hydrate thereof, is a monohydrate, bis-mesylate salt of a compound of Formula I. In some embodiments, crystallization is prevented for more than nine months under 40° C./75% RT open conditions. In some embodiments, the composition is a feed solution for spray drying.

In one variation of the pharmaceutical composition, the bis-mesylate salt of Formula IA is formulated for immediate release. While hydroxypropylmethylcellulose is commonly used in the art for sustained release formulations, the use of hydroxypropylmethylcellulose in an immediate release formulation of the bis-mesylate salt of Formula IA was observed to increase bioavailability of the bis-mesylate salt of Formula IA administered to the subject compared to a formulation without the use of hydroxypropylmethylcellulose. In some instances, hydroxypropylmethylcellulose was observed to prolong supersaturation of a compound of Formula I, or a pharmaceutically acceptable salt thereof (including, for example, the mono-mesylate or bis-mesylate salt). In other instances, hydroxypropylmethylcellulose was observed to minimize crystallization of a compound of Formula I, or a pharmaceutically acceptable salt thereof (including, for example, the mono-mesylate or bis-mesylate salt) from a solution of a compound of Formula I, or a pharmaceutically acceptable salt thereof (including, for example, a mono-mesylate or bis-mesylate salt thereof).

In one variation, at least one of the pharmaceutically acceptable polymers is any pharmaceutically acceptable polymer (a) capable of prolonging supersaturation of a compound of Formula I, or a pharmaceutically acceptable salt thereof (including, for example, the mono-mesylate or bis-mesylate salt); (b) capable of minimizing crystallization of a compound of Formula I, or a pharmaceutically acceptable salt thereof (including, for example, the mono-mesylate or bis-mesylate salt) from a solution of a compound of Formula I, or a pharmaceutically acceptable salt thereof (including, for example, the mono-mesylate or bis-mesylate salt); or both (a) and (b).

In some embodiments, in addition to the mesylate salt (including, for example, the bis-mesylate salt) of a compound of Formula I, or a hydrate thereof, and hydroxypropylmethylcellulose, the pharmaceutical composition may further comprise one or more additional pharmaceutically acceptable polymers. Such additional polymers may include, for example, block copolymers and naturally occurring polymers. Suitable additional polymers may, for example, be selected from the group consisting of crospovidone, povidone, poloxamer, microcrystalline cellulose, and any combinations thereof.

In other embodiments, in addition to the mesylate salt (including, for example, the bis-mesylate salt) of a compound of Formula I, or a hydrate thereof, hydroxypropylmethylcellulose and one or more additional polymers, the pharmaceutical composition may further comprise one or more other pharmaceutically acceptable carriers. Such other carriers may be selected from the group consisting of lactose monohydrate, mannitol, sodium lauryl sulfate, colloidal silicon dioxide, magnesium stearate, and any combinations thereof.

It should be understood that the amount of individual components (e.g., the active agent and pharmaceutically acceptable carriers) of the pharmaceutical composition may vary depending on several factors, including the unit dosage form (e.g., a tablet incorporating the active agent by spray drying and/or dry granulation).

The term "% w/w" as used herein refers to the weight of a component based on the total weight of a composition comprising the component. For example, if component A is present in an amount of 50% w/w in a 100 mg composition, component A is present in an amount of 50 mg.

As used herein, "a" means one or more unless indicated otherwise.

The use of the term "about" includes and describes the value or parameter per se. For example, "about x" includes and describes "x" per se. In some embodiments, the term "about" when used in association with a measurement, or used to modify a value, a unit, a constant, or a range of values, refers to variations of ±10%. For example, "about 2:8" in some embodiments includes 1.8-2.2:7.2-8.8.

Table A below provides exemplary weight percent of certain components (e.g., active agent and carriers) for use in the formulations.

TABLE A

Exemplary weight percent of components in the formulation of a compound of Formula I, or a pharmaceutically acceptable salt thereof

| Component in Composition | Weight Percent of Component in Composition |
|---|---|
| Compound of Formula I, or pharmaceutically acceptable salt thereof (e.g., free base of a compound of Formula I, or mono-mesylate salt of a compound of Formula I, or bis-mesylate salt of a compound of Formula I), or a hydrate thereof; or polymorph Form 3, polymorph Form 7, or any combination thereof | From about 1% w/w to about 70% w/w, or about 1% w/w to about 60% w/w, or about 1% w/w to about 50% w/w, or from about 1% w/w to about 45% w/w, or from about 5% w/w to about 40% w/w, or from about 5% w/w to about 35% w/w, or from about 5% w/w to about 25% w/w, or from about 10% w/w to about 20% w/w, or from about 30% w/w and 40% w/w, or from about 35% w/w and 40% w/w; or at about 5% w/w, at about 10% w/w, at about 15% w/w, at about 20% w/w, at about 25% w/w, at about 30% w/w, at about 31% w/w, at about 32% w/w, at about 33% w/w, at about 34% w/w, at about 35% w/w, at about 36% w/w, at about 37% w/w, at about 38% w/w, at about 39% w/w, at about 40% w/w, at about 45% w/w, at about 50% w/w, at about 60%, or at about 70% |
| Precipitation inhibitor (e.g., HPMC) | From about 1% w/w to about 50% w/w, or from about 1% w/w to about 45% w/w, or from about 5% w/w to about 40% w/w, or from about 5% w/w to about 35% w/w, or from about 5% w/w to about 25% w/w, or from about 10% w/w to about 20% w/w; or at about 1% w/w, at about 2% w/w, at about 3% w/w, at about 4% w/w, at about 5% w/w, at about 10% w/w, at about 15% w/w, at about 20% w/w, at about 25% w/w, at about 26% w/w, at about 27% w/w, at about 28% w/w, at about 29% wow, at about 30% w/w, at about 35% w/w, at about 40% w/w, at about 45% w/w, or at about 50% w/w |
| Diluent (e.g., Mannitol, or Microcrystalline cellulose) | From about 1% w/w to about 50% w/w, or from about 1% w/w to about 45% w/w, or from about 5% w/w to about 40% w/w, or from about 5% w/w to about 35% w/w, or from about 5% w/w to about 25% w/w, or from about 10% w/w to about 20% w/w, or from about 20% w/w to about 30% w/w, or about 25% w/w to about 30% w/w, or from about 25% w/w and 35% w/w, or from about 25% w/w and 40% w/w; or at about 5% w/w, at about 10% w/w, at about 15% w/w, at about 20% w/w, at about 21% w/w, at |

TABLE A-continued

Exemplary weight percent of components in the formulation of a compound of Formula I, or a pharmaceutically acceptable salt thereof

| Component in Composition | Weight Percent of Component in Composition |
|---|---|
| | about 22% w/w, at about 23% w/w, at about 24% w/w, at about 25% w/w, at about 28% w/w, at about 30% w/w, at about 35% w/w, at about 40% w/w, at about 45% w/w, or at about 50% w/w |
| Disintegrant (e.g., Crospovidone) | From about 1% w/w to about 25% w/w, or from about 1 to about 10% w/w, or from about 1% w/w to about 5% w/w; or at about 1% w/w, at about 2% w/w, at about 3% w/w, at about 4% w/w, at about 5% w/w, at about 10% w/w, at about 15% w/w, at about 20% w/w, or at about 25% w/w |
| Surfactant (e.g., Poloxomer) | From about 1% w/w to about 25% w/w, or from about 1 to about 10% w/w, or from about 1% w/w to about 5% w/w; or at about 1% w/w, at about 2% w/w, at about 3% w/w, at about 4% w/w, at about 5% w/w, at about 10% w/w, at about 15% w/w, at about 20% w/w, or at about 25% w/w |
| Glidant (e.g., Colloidal silicon dioxide) | From about 0.1% w/w to about 10% w/w, or from about 0.1% w/w to about 5% w/w, or from about 0.5% w/w to about 1% w/w, or from about 0.5% to about 10%, or from 1% w/w to about 25% w/w, or from about 1 to about 10% w/w, or from about 1% w/w to about 5% w/w; or at about 1% w/w, at about 1.25% w/w, at about 1.5% w/w, at about 2% w/w, at about 3% w/w, at about 4% w/w, at about 5% w/w, at about 10% w/w, at about 15% w/w, at about 20% w/w, or at about 25% w/w |
| Lubricant (e.g., Magnesium stearate) | From about 0.1% w/w to about 10% w/w, or from about 0.1% w/w to about 5% w/w, or from about 0.5% w/w to about 1% w/w; or at about 0.1% w/w, at about 0.5% w/w, at about 0.75% w/w, at about 1% w/w, at about 1.25% w/w, at about 1.5% w/w, at about 2% w/w, at about 3% w/w, at about 4% w/w, or at about 5% w/w |

It is understood that the components in the pharmaceutical compositions provided may be present in amounts that result in one or more advantageous properties as described in the present disclosure. In one variation, the amounts are as described in Table A. Thus, the pharmaceutical compositions described may comprise the formulation components in a weight percentage detailed herein, the same as if each and every combination of component and weight percent were specifically and individually listed.

For example, in some variations, the pharmaceutical composition comprises from about 30% w/w to about 45% w/w of a pharmaceutically acceptable salt (including, for example, a mesylate salt) of a compound of Formula I, or a hydrate thereof, from about 8% w/w to 13% w/w of one or more disintegrants, about 3% w/w of one or more surfactants; and about 19% w/w to 28% w/w of one or more diluents. In other variations, the pharmaceutical composition comprises from about 30% w/w to about 45% w/w of a mesylate salt (including, for example, mono-mesylate or bis-mesylate salt) of a compound of Formula I, from about 8% w/w to 13% w/w of one or more disintegrants, about 3% w/w of one or more surfactants; and about 19% w/w to 28% w/w of one or more diluents.

In some variations, the pharmaceutical composition comprises from about 30% w/w to about 45% w/w of a pharmaceutically acceptable salt (including, for example, a mesylate salt) of a compound of Formula I, or a hydrate thereof, from about 10% w/w to 30% w/w hydroxypropylmethylcellulose, and from about 20% w/w to about 30% w/w mannitol. In other variations, the pharmaceutical composition comprises from about 30% w/w to about 45% w/w Form 3 (which is a polymorph of a monohydrate, bis-mesylate salt of Formula IA), from about 10% w/w to 30% w/w hydroxypropylmethylcellulose, and from about 20% w/w to about 30% w/w mannitol.

In other variations, the pharmaceutical composition comprises from about 30% w/w to about 45% w/w of a pharmaceutically acceptable salt (including, for example, a mesylate salt) of a compound of Formula I, or a hydrate thereof, from about 10% w/w to 30% w/w hydroxypropylmethylcellulose, and from about 5% w/w to about 15% w/w crospovidone. In another variation, the pharmaceutical composition comprises from about 30% w/w to about 45% w/w Form 3 (which is a polymorph of a monohydrate, bis-mesylate salt of Formula IA), from about 10% w/w to 30% w/w hydroxypropylmethylcellulose, and from about 5% w/w to about 15% w/w crospovidone.

In other variations, the pharmaceutical composition comprises from about 30% w/w to about 45% w/w of a pharmaceutically acceptable salt (including, for example, a mesylate salt) of a compound of Formula I, or a hydrate thereof, from about 10% w/w to 30% w/w hydroxypropylmethylcellulose, and from about 1% w/w to about 5% w/w poloxamer. In another variation, the pharmaceutical composition comprises from about 30% w/w to about 45% w/w Form 3 (which is a polymorph of a monohydrate, bis-mesylate salt of Formula IA), from about 10% w/w to 30% w/w hydroxypropylmethylcellulose, and from about 1% w/w to about 5% w/w poloxamer.

In yet other variations, the pharmaceutical composition comprises from about 30% w/w to about 45% w/w of a pharmaceutically acceptable salt (including, for example, a mesylate salt) of a compound of Formula I, or a hydrate thereof, from about 10% w/w to 30% w/w hydroxypropylmethylcellulose, and from about 0.1% w/w to about 2% w/w colloidal silicon dioxide. In another variation, the pharmaceutical composition comprises from about 30% w/w to about 45% w/w Form 3 (which is a polymorph of a monohydrate, bis-mesylate salt of Formula IA), from about 10% w/w to 30% w/w hydroxypropylmethylcellulose, and from about 0.1% w/w to about 2% w/w colloidal silicon dioxide.

In yet other variations, the pharmaceutical composition comprises from about 30% w/w to about 45% w/w of a pharmaceutically acceptable salt (including, for example, a mesylate salt) of a compound of Formula I, or a hydrate thereof, from about 10% w/w to 30% w/w hydroxypropylmethylcellulose, and from about 1% w/w to about 5% w/w microcrystalline cellulose. In another variation, the pharmaceutical composition comprises from about 30% w/w to about 45% w/w Form 3 (which is a polymorph of a monohydrate, bis-mesylate salt of Formula IA), from about 10% w/w to 30% w/w hydroxypropylmethylcellulose, and from about 1% w/w to about 5% w/w microcrystalline cellulose.

In yet other variations, the pharmaceutical composition comprises from about 30% w/w to about 45% w/w of a pharmaceutically acceptable salt (including, for example, a mesylate salt) of a compound of Formula I, or a hydrate thereof, from about 10% w/w to 30% w/w hydroxypropylmethylcellulose, and from about 0.5% w/w to about 2% w/w magnesium stearate. In another variation, the pharmaceutical composition comprises from about 30% w/w to about 45% w/w Form 3 (which is a polymorph of a monohydrate, bis-mesylate salt of Formula IA), from about 10% w/w to 30% w/w hydroxypropylmethylcellulose, and from about 0.5% w/w to about 2% w/w magnesium stearate.

In yet other variations, the pharmaceutical composition comprises from about 30% w/w to about 45% w/w of a pharmaceutically acceptable salt (including, for example, a mesylate salt) of a compound of Formula I, or a hydrate thereof, from about 10% w/w to 30% w/w hydroxypropylmethylcellulose, from about 20% w/w to about 30% w/w mannitol, and from about 5% w/w to about 15% w/w crospovidone. In yet another variation, the pharmaceutical composition comprises from about 30% w/w to about 45% w/w Form 3 (which is a polymorph of a monohydrate, bis-mesylate salt of Formula IA), from about 10% w/w to 30% w/w hydroxypropylmethylcellulose, from about 20% w/w to about 30% w/w mannitol, and from about 5% w/w to about 15% w/w crospovidone.

In yet other variations, the pharmaceutical composition comprises from about 30% w/w to about 45% w/w of a pharmaceutically acceptable salt (including, for example, a mesylate salt) of a compound of Formula I, or a hydrate thereof, from about 10% w/w to 30% w/w hydroxypropylmethylcellulose, from about 20% w/w to about 30% w/w mannitol, from about 5% w/w to about 15% w/w crospovidone, and from about 0.1% w/w to about 2% w/w colloidal silicon dioxide. In yet another variation, the pharmaceutical composition comprises from about 30% w/w to about 45% w/w Form 3 (which is a polymorph of a monohydrate, bis-mesylate salt of Formula IA), from about 10% w/w to 30% w/w hydroxypropylmethylcellulose, from about 20% w/w to about 30% w/w mannitol, from about 5% w/w to about 15% w/w crospovidone, and from about 0.1% w/w to about 2% w/w colloidal silicon dioxide.

In yet another variation, the pharmaceutical composition comprises from about 30% w/w to about 45% w/w of a pharmaceutically acceptable salt (including, for example, a mesylate salt) of a compound of Formula I, or a hydrate thereof, from about 10% w/w to 30% w/w hydroxypropylmethylcellulose, from about 20% w/w to about 30% w/w mannitol, from about 5% w/w to about 15% w/w crospovidone, from about 0.1% w/w to about 2% w/w colloidal silicon dioxide, and from about 1% w/w to about 5% w/w microcrystalline cellulose. In yet another variation, the pharmaceutical composition comprises from about 30% w/w to about 45% w/w Form 3 (which is a polymorph of a monohydrate, bis-mesylate salt of Formula IA), from about 10% w/w to 30% w/w hydroxypropylmethylcellulose, from about 20% w/w to about 30% w/w mannitol, from about 5% w/w to about 15% w/w crospovidone, from about 0.1% w/w to about 2% w/w colloidal silicon dioxide, and from about 1% w/w to about 5% w/w microcrystalline cellulose.

In yet other variations, the pharmaceutical composition comprises from about 30% w/w to about 45% w/w of a pharmaceutically acceptable salt (including, for example, a mesylate salt) of a compound of Formula I, or a hydrate thereof, from about 10% w/w to 30% w/w hydroxypropylmethylcellulose, mannitol, from about 5% w/w to about 15% w/w crospovidone, from about 0.1% w/w to about 2% w/w colloidal silicon dioxide, from about 1% w/w to about 5% w/w microcrystalline cellulose, and from about 0.5% w/w to about 2% w/w magnesium stearate. In yet another variation, the pharmaceutical composition comprises from about 30% w/w to about 45% w/w Form 3 (which is a polymorph of a monohydrate, bis-mesylate salt of Formula IA), from about 10% w/w to 30% w/w hydroxypropylmethylcellulose, mannitol, from about 5% w/w to about 15% w/w crospovidone, from about 0.1% w/w to about 2% w/w colloidal silicon dioxide, from about 1% w/w to about 5% w/w microcrystalline cellulose, and from about 0.5% w/w to about 2% w/w magnesium stearate.

In certain variations of any of the foregoing pharmaceutical compositions, the mesylate salt, or a hydrate thereof, comprises a cation of a compound of Formula I and a mesylate anion, wherein the mesylate anion and the cation of a compound of Formula I are present in a molar ratio of the mesylate anion tp the cation of a compound of Formula I:
(i) at least 1:1, or between 1:1 and 3.3:1, between 1.9:1 and 3.3:1, between 1.9:1 and 2.5:1, between 1.9:1 and 2.4:1, between 2:1 to 3.3:1, between 2:1 and 3:1, or between 2:1 and 2.7:1, or between 2.1:1 and 2.5:1, or between 2.2:1 and 2.4:1, or about 2.3:1, or about 2.4:1; or
(ii) greater than 1:1 and less than 2:1; or
(iii) greater than 2:1.

In other variations of any of the foregoing pharmaceutical compositions, the mesylate salt is a bis-mesylate salt of a compound of Formula I, or a hydrate thereof. In one variation, the mesylate salt is a monohydrate, bis-mesylate salt of a compound of Formula I. It should also be understood that in any of the foregoing pharmaceutical compositions, the bis-mesylate salt may be represented by Formula IA, IB, IC, ID or IE as described above.

Tablets

The pharmaceutical compositions provided in the present disclosure are typically administered orally. Administration may be via capsule, tablet, or the like. In certain embodiments, the composition provided herein is a tablet.

Dry Granulation

In some embodiments, the composition is a tablet prepared by dry granulation formulation (e.g., a tablet prepared by formulating a compound of Formula I or a pharmaceutically acceptable salt or hydrate thereof as a granulation). As used herein, "dry granulation formulation" refers to a formulation prepared through a dry granulation process. Dry granulation (also referred to as dry granulating) generally refers to the process of forming granules without using a liquid solution. A "granulation" refers to a product obtained by dry granulation. In one variation, provided is a dry granulation tablet. A tablet formed by dry granulation and compression is referred to herein as a "dry granulation tablet."

In some variations, the tablet is prepared by dry granulating a bis-mesylate salt of a compound of Formula I, or a hydrate thereof, to form a granulation; and compressing the granulation. In certain variations, the tablet is prepared by dry granulating a monohydrate, a bis-mesylate salt of a compound of Formula I to form a granulation; and compressing the granulation. In one variation, the tablet is prepared by dry granulating polymorph Form 3, which is a polymorph of a monohydrate, a bis-mesylate salt of a compound of Formula I to form a granulation; and compressing the granulation.

In some aspects, provided herein is a tablet, comprising:
(i) a bis-mesylate salt of a compound of Formula I:

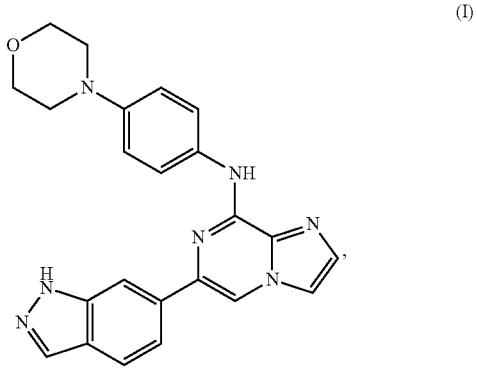 [SMILES: c1cn2cc(-c3ccc4cn[nH]c4c3)nc(Nc3ccc(N4CCOCC4)cc3)c2n1]

(I)

or a hydrate thereof, and
(ii) at least one pharmaceutically acceptable carrier.

In certain aspects, provided herein is a tablet, comprising: (i) Form 3, which is a polymorph of a monohydrate, bis-mesylate salt of a compound of Formula I; and (ii) at least one pharmaceutically acceptable carrier.

In one variation, the polymorph of the monohydrate, bis-mesylate salt of the compound of Formula I (e.g., Form 3) is characterized by or has an X-ray diffraction pattern comprising 2θ-reflections (±0.2°) at 13.8, 16.9, 22.9, and 26.1. In another variation, the polymorph of the monohydrate, bis-mesylate salt of the compound of Formula I is characterized by or has an X-ray diffraction pattern comprising 2θ-reflections (±0.2°) at 7.7, 12.9, 17.7, and 18.1. In other variations, the polymorph of the monohydrate, bis-mesylate salt of the compound of Formula I is characterized by or has an X-ray diffraction pattern comprising 2θ-reflections (±0.2°) at 7.7, 12.9, 13.8, 16.9, 17.7, 18.1, 22.9, and 26.1. In yet other variations, the polymorph of the monohydrate, bis-mesylate salt of the compound of Formula I is characterized by or has an X-ray diffraction pattern comprising at least three or more; at least four or more; or at least five or more of the 2θ-reflections (±0.2 degrees): 7.7, 12.9, 13.8, 16.9, 17.7, 18.1, 22.9, and 26.1. When describing the 2θ-reflections in the X-ray diffraction pattern (e.g., of polymorph Form 3, also referred to herein as "Form 3" or "Form III"), it should be understood that ±0.2° can also be expressed as "plus or minus 0.2 degrees 2θ".

In one variation, the polymorph of the monohydrate, bis-mesylate salt of the compound of Formula I (e.g., Form 3) is characterized by or has an X-ray diffraction pattern substantially as shown in FIG. 1A. In another variation, the polymorph of the monohydrate, bis-mesylate salt of the compound of Formula I (e.g., Form 3) is characterized by or has an X-ray diffraction pattern substantially as shown in FIG. 1B. In yet another variation, the polymorph of the monohydrate, bis-mesylate salt of the compound of Formula I (e.g., Form 3) is characterized by a unit cell as determined by crystal X-ray crystallography of the following dimensions: a=8.7831(6) Å; b=11.8484(8) Å; c=14.2485(10) Å; α=98.108(6)°; β=100.955(6)°; and γ=98.861(6)°.

In certain embodiments of the tablet, at least one pharmaceutically acceptable carrier is a precipitation inhibitor. In one variation, the precipitation inhibitor is hydroxypropylmethylcellulose (HPMC). In another variation, the precipitation inhibitor is copovidone.

In other embodiments, the tablet further comprises at least one diluent, binder, disintegrant, surfactant, glidant, or lubricant, or any combinations thereof. For example, any suitable diluents, binders, disintegrants, surfactants, glidants, or lubricants described herein may be present in the tablet. In certain variations, the tablet comprises at least one diluent. In one variation, the diluent is mannitol. In other variations, the tablet further comprises any one or more of crospovidone, poloxamer, colloidal silicon dioxide, magnesium stearate, and microcrystalline cellulose.

Thus, in some variations, the tablet comprises (i) a bis-mesylate salt of a compound of Formula I, or a hydrate thereof, and (ii) hydroxypropylmethylcellulose. In certain variations, the tablet comprises (i) a monohydrate, bis-mesylate salt of a compound of Formula I, and (ii) hydroxypropylmethylcellulose. In one variation, the tablet comprises (i) polymorph Form 3, which is a polymorph of a monohydrate, bis-mesylate salt of a compound of Formula I, and (ii) hydroxypropylmethylcellulose.

In other variations, the tablet comprises (i) a bis-mesylate salt of a compound of Formula I, or a hydrate thereof, (ii) hydroxypropylmethylcellulose; and (iii) mannitol. In certain variations, the tablet comprises (i) a monohydrate, bis-mesylate salt of a compound of Formula I, (ii) hydroxypropylmethylcellulose; and (iii) mannitol. In one variation, the tablet comprises (i) polymorph Form 3, which is a polymorph of a monohydrate, bis-mesylate salt of a compound of Formula I, (ii) hydroxypropylmethylcellulose; and (iii) mannitol.

In other variations, the tablet comprises (i) a bis-mesylate salt of a compound of Formula I, or a hydrate thereof, (ii) hydroxypropylmethylcellulose; (iii) mannitol, and (iv) one or more, two or more, three or more, four or more, or all five of crospovidone, poloxamer, colloidal silicon dioxide, magnesium stearate, and microcrystalline cellulose. In certain variations, the tablet comprises (i) a monohydrate, bis-mesylate salt of a compound of Formula I, (ii) hydroxypropylmethylcellulose; (iii) mannitol, and (iv) one or more, two or more, three or more, four or more, or all five of crospovidone, poloxamer, colloidal silicon dioxide, magnesium stearate, and microcrystalline cellulose. In one variation, the tablet comprises (i) Form 3, which is a polymorph of a monohydrate, bis-mesylate salt of a compound of Formula I, (ii) hydroxypropylmethylcellulose; (iii) mannitol, and (iv) one or more, two or more, three or more, four or more, or all five of crospovidone, poloxamer, colloidal silicon dioxide, magnesium stearate, and microcrystalline cellulose.

A skilled artisan would further recognize that the amounts of components used in the formulation may vary, depending on the method and technique used.

In certain variations, the pharmaceutical composition is a tablet (e.g., a tablet prepared by formulating a compound of Formula I or a pharmaceutically acceptable salt or hydrate thereof as a granulation) comprising a mono-mesylate or bis-mesylate salt of a compound of Formula I, or a hydrate thereof, and at least one precipitation inhibitor. In one variation, the precipitation inhibitor is hydroxypropylmethylcellulose.

In another variation, the pharmaceutical composition is a tablet (e.g., a tablet prepared by formulating a compound of Formula I or a pharmaceutically acceptable salt or hydrate thereof as a granulation) comprising a mono-mesylate or bis-mesylate salt of a compound of Formula I, or a hydrate thereof, comprising at least one precipitation inhibitor, and at least one diluent.

In another variation, the pharmaceutical composition is a tablet (e.g., a tablet prepared by formulating a compound of Formula I or a pharmaceutically acceptable salt or hydrate thereof as a granulation) comprising a mono-mesylate or bis-mesylate salt of a compound of Formula I, or a hydrate thereof, at least one precipitation inhibitor, and at least one disintegrant.

In another variation, the pharmaceutical composition is a tablet (e.g., a tablet prepared by formulating a compound of Formula I or a pharmaceutically acceptable salt or hydrate thereof as a granulation) comprising a mono-mesylate or bis-mesylate salt of a compound of Formula I, or a hydrate thereof, at least one precipitation inhibitor, and at least one surfactant.

In another variation, the pharmaceutical composition is a tablet (e.g., a tablet prepared by formulating a compound of Formula I or a pharmaceutically acceptable salt or hydrate thereof as a granulation) comprising a mono-mesylate or bis-mesylate salt of a compound of Formula I, or a hydrate thereof, at least one precipitation inhibitor, and at least one glidant.

In another variation, the pharmaceutical composition is a tablet (e.g., a tablet prepared by formulating a compound of Formula I or a pharmaceutically acceptable salt or hydrate thereof as a granulation) comprising the mono-mesylate or bis-mesylate salt of the compound of Formula I, or a hydrate thereof, at least one precipitation inhibitor, and at least one lubricant.

In another variation, the pharmaceutical composition is a tablet (e.g., a tablet prepared by formulating a compound of Formula I or a pharmaceutically acceptable salt or hydrate thereof as a granulation) comprising a mono-mesylate or bis-mesylate salt of a compound of Formula I, or a hydrate thereof, at least one precipitation inhibitor, at least one diluent, and at least surfactant.

In any of the foregoing embodiments of the tablet prepared by formulating a compound of Formula I or a pharmaceutically acceptable salt or hydrate thereof as a granulation, the bis-mesylate salt of a compound of Formula I, or a hydrate thereof, is a hydrate, bis-mesylate salt of a compound of Formula I. In one variation, the bis-mesylate salt of a compound of Formula I, or a hydrate thereof, is a monohydrate, bis-mesylate salt of a compound of Formula I.

In other variations, the pharmaceutical composition is a tablet (e.g., a tablet prepared by formulating a compound of Formula I or a pharmaceutically acceptable salt or hydrate thereof as a granulation) comprising polymorphic Form 3, at least one precipitation inhibitor, at least one diluent, and at least surfactant.

In other variations, the pharmaceutical composition is a tablet (e.g., a tablet prepared by formulating a compound of Formula I or a pharmaceutically acceptable salt or hydrate thereof as a granulation) comprising Form 3, hydroxypropylmethylcellulose, and mannitol.

In another variation, the pharmaceutical composition is a tablet (e.g., a tablet prepared by formulating a compound of Formula I or a pharmaceutically acceptable salt or hydrate thereof as a granulation) comprising Form 3, hydroxypropylmethylcellulose, and crospovidone.

In another variation, the pharmaceutical composition is a tablet (e.g., a tablet prepared by formulating a compound of Formula I or a pharmaceutically acceptable salt or hydrate thereof as a granulation) comprising Form 3, hydroxypropylmethylcellulose, and poloxamer.

In another variation, the pharmaceutical composition is a tablet (e.g., a tablet prepared by formulating a compound of Formula I or a pharmaceutically acceptable salt or hydrate thereof as a granulation) comprising Form 3, hydroxypropylmethylcellulose, and colloidal silicon dioxide.

In another variation, the pharmaceutical composition is a tablet (e.g., a tablet prepared by formulating a compound of Formula I or a pharmaceutically acceptable salt or hydrate thereof as a granulation) comprising Form 3, hydroxypropylmethylcellulose, and microcrystalline cellulose.

In another variation, the pharmaceutical composition is a tablet (e.g., a tablet prepared by formulating a compound of Formula I or a pharmaceutically acceptable salt or hydrate thereof as a granulation) comprising Form 3, hydroxypropylmethylcellulose, and magnesium stearate.

In yet another variation, the pharmaceutical composition is a tablet (e.g., a tablet prepared by formulating a compound of Formula I or a pharmaceutically acceptable salt or hydrate thereof as a granulation) comprising Form 3, hydroxypropylmethylcellulose, mannitol, and crospovidone.

In yet another variation, the pharmaceutical composition is a tablet (e.g., a tablet prepared by formulating a compound of Formula I or a pharmaceutically acceptable salt or hydrate thereof as a granulation) comprising Form 3, hydroxypropylmethylcellulose, mannitol, crospovidone, and colloidal silicon dioxide.

In yet another variation, the pharmaceutical composition is a tablet (e.g., a tablet prepared by formulating a compound of Formula I or a pharmaceutically acceptable salt or hydrate thereof as a granulation) comprising Form 3, hydroxypropylmethylcellulose, mannitol, crospovidone, colloidal silicon dioxide, and microcrystalline cellulose.

In yet another variation, the pharmaceutical composition is a tablet (e.g., a tablet prepared by formulating a compound of Formula I or a pharmaceutically acceptable salt or hydrate thereof as a granulation) comprising Form 3, hydroxypropylmethylcellulose, mannitol, crospovidone, colloidal silicon dioxide, microcrystalline cellulose, and magnesium stearate.

In certain variations, the pharmaceutical composition is a tablet (e.g., a tablet prepared by formulating a compound of Formula I or a pharmaceutically acceptable salt or hydrate thereof as a granulation) comprising Form 3, and at least one pharmaceutically acceptable carrier selected from the group consisting of hydroxypropylmethylcellulose, mannitol, crospovidone, poloxamer, colloidal silicon dioxide, microcrystalline cellulose, magnesium stearate, and any mixtures thereof.

In another variation, the pharmaceutical composition is a tablet (e.g., a tablet prepared by formulating a compound of Formula I or a pharmaceutically acceptable salt or hydrate thereof as a granulation) comprising Form 3, hydroxypropylmethylcellulose, and at least one additionally pharmaceutically acceptable carrier selected from the group consisting of mannitol, crospovidone, poloxamer, colloidal silicon dioxide, microcrystalline cellulose, magnesium stearate, and any mixtures thereof.

In any of the foregoing variations, it is understood that Form 3 is a polymorph of a monohydrate, bis-mesylate salt of a compound of Formula I (or a polymorph of a monohydrate of a bis-mesylate salt of Formula IA or IB).

It should be understood that the weight percent of the components of the tablet prepared by formulating a compound of Formula I or a pharmaceutically acceptable salt or hydrate thereof as a granulation may be as provided in Table A above, the same as if each and every combination of pharmaceutically acceptable carrier were specifically and individually listed.

The pharmaceutical compositions provided in the present disclosure that are prepared by dry granulation (e.g., tablet prepared by formulating a compound of Formula I or a pharmaceutically acceptable salt or hydrate thereof as a granulation) may comprise, in some embodiments, a mesylate salt of the compound of Formula I, or a hydrate thereof; or in certain embodiments, a mono-mesylate of the compound of Formula I; or in certain embodiments, a bis-mesylate salt of the compound of Formula I, or a hydrate thereof; or in certain embodiments, a bis-mesylate salt of Formula IA, or a hydrate thereof, including crystalline, non-crystalline, or amorphous salts; or in one embodiment, polymorphic Form 3, Form 7, or a mixture thereof, which are polymorphs of a bis-mesylate salt of Formula IA.

In certain aspects, provided herein are methods of manufacturing a tablet, comprising:

a) dry granulating: (i) a pharmaceutically acceptable salt (e.g., a bis-mesylate salt) of a compound of Formula I or a hydrate thereof, and (ii) at least one pharmaceutically acceptable carrier to form a granulation; and b) compressing the granulation to form the tablet.

A skilled artisan would recognize suitable methods and techniques to prepare a tablet by dry granulation. Exemplary methods and techniques to prepare powders for compression into a tablet include dry granulation or wet granulation. Wet granulation generally refers to the process of adding a liquid solution to powders to granulate.

In some embodiments, the tablets provided herein are prepared by dry granulation. For example, in some embodiments, a pharmaceutically acceptable salt (including, for example, a bis-mesylate salt) of a compound of Formula I or a hydrate thereof, and pharmaceutically acceptable carriers are blended, milled, and compressed to form a tablet, which may be coated and packaged. In certain embodiments, the mesylate salt (including, for example, the mono-mesylate or bis-mesylate salt) of a compound of Formula I and pharmaceutically acceptable carriers are blended, dry granulated, milled, and compressed to form a tablet, which may be coated and packaged. An exemplary manufacturing process for preparing a tablet of the bis-mesylate salt of a compound of Formula I by dry granulation is described in Example B1 below. In certain variations, the dry granulation employs roller compaction.

In certain embodiments, the tablets provided herein (e.g., a tablet comprising a bis-mesylate salt of a compound of Formula I) are prepared from a granulation with a mean particle size between 200 μm to 400 μm, or between 250 μm to 350 μm, which may be beneficial for production of tablets. In certain embodiments, the tablets provided herein are formulated with a granulation having Flodex between 10 to 20 nm, or between 10 to 15 nm, which may be beneficial for production of tablets. In certain embodiments, the tablets provided herein are formulated with a granulation having a bulk density of between 0.4 g/mL to 0.7 g/mL, or between 0.5 g/mL to about 0.6 g/mL, which may be beneficial for production of tablets. In certain embodiments, the tablets provided herein are formulated with a granulation having a tap density between 0.5 g/mL to 0.9 g/mL, or between 0.6 g/mL to 0.8 g/mL tap density, which may be beneficial for production of tablets.

Provided is also a tablet (e.g., a dry granulation tablet) produced according to any of the foregoing methods.

Spray Drying

In some variations, the tablet is prepared by spray drying a compound of Formula I, or a pharmaceutically acceptable salt thereof, or a hydrate thereof, to form a solid dispersion; and dry granulating the solid dispersion. In certain variations, the tablet is prepared by spray drying a compound of Formula I and methanesulfonic acid to form a solid dispersion; and dry granulating the solid dispersion. In certain variations, the tablet is prepared by spray drying a mesylate salt of a compound of Formula I, or a hydrate thereof, and optionally methanesulfonic acid, to form a solid dispersion; and dry granulating the solid dispersion. In certain variations, the tablet is prepared by spray drying a mono-mesylate salt of compound of Formula I, or a hydrate thereof, and methanesulfonic acid, to form a solid dispersion; and dry granulating the solid dispersion. In one variation, the tablet is prepared by spray drying a bis-mesylate salt of a compound of Formula I, or a hydrate thereof, and optionally methanesulfonic acid, to form a solid dispersion; and dry granulating the solid dispersion. In another variation, the tablet is prepared by spray drying a hydrate, bis-mesylate salt of a compound of Formula I, and optionally methanesulfonic acid, to form a solid dispersion; and dry granulating the solid dispersion. In yet another variation, the tablet is prepared by spray drying a monohydrate, bis-mesylate salt of a compound of Formula I, and optionally methanesulfonic acid, to form a solid dispersion; and dry granulating the solid dispersion. In yet another variation, the tablet is prepared by spray drying polymorphic Form 3, which is a polymorph of a monohydrate, bis-mesylate salt of a compound of Formula I, and optionally methanesulfonic acid, to form a solid dispersion; and dry granulating the solid dispersion.

In each of the foregoing variations, dry granulating of the solid dispersion forms a granulation; and the method further comprises compressing the granulation to form a tablet. In any of the foregoing variations, the solid dispersion is a spray-dried solid dispersion, which is also referred to herein as spray-dried powder.

Thus, the compositions (including, for example, pharmaceutical compositions) provided herein may, in certain embodiments, be a tablet comprising a spray-dried solid dispersion. Such tablets may also be referred to herein as a "spray-dried solid dispersion tablet".

In some aspects, provided herein is a tablet comprising:

(i) a bis-mesylate salt of a compound of Formula I:

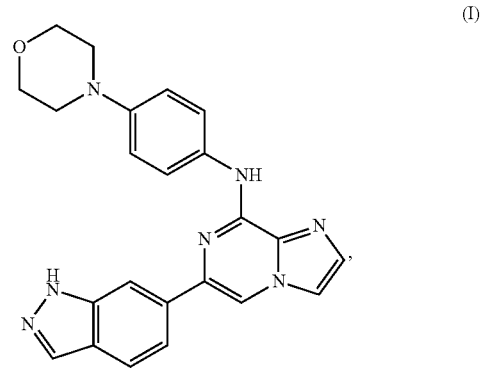 [SMILES: c1cn2cc(-c3ccc4cn[nH]c4c3)nc(Nc3ccc(N4CCOCC4)cc3)c2n1]

(I)

and (ii) at least one pharmaceutically acceptable carrier.

In some embodiments, the tablet further comprises additional methanesulfonic acid, or an anion thereof.

In other aspects, provided herein is a tablet, comprising:
(i) a mesylate salt of a compound of Formula I:

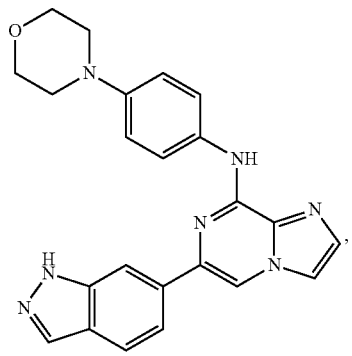

(I)

wherein the mesylate salt comprises a cation of the compound of Formula I and a mesylate anion; and
(ii) at least one pharmaceutically acceptable carrier.

In one variation of the tablet, the molar ratio of the mesylate anion to the cation of the compound of Formula I is at least 1:1, or between 1:1 and 3.3:1, between 1.9:1 and 3.3:1, between 1.9:1 and 2.5:1, between 1.9:1 and 2.4:1, between 2:1 to 3.3:1, between 2:1 and 3:1, or between 2:1 and 2.7:1, or between 2.1:1 and 2.5:1, or between 2.2:1 and 2.4:1, or about 2.3:1, or about 2.4:1. In another variation, the molar ratio of the mesylate anion to the cation of the compound of Formula I is greater than 1:1 and less than 2:1. In yet another variation, the molar ratio of the mesylate anion to the cation of the compound of Formula I is greater than 2:1.

In yet other aspects, provided herein is a tablet comprising:
(i) a compound of Formula I:

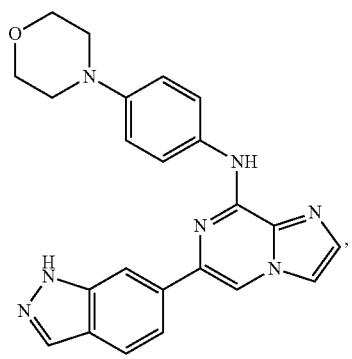

(I)

or a cation thereof;
(ii) methanesulfonic acid, or an anion thereof; and
(iii) at least one pharmaceutically acceptable carrier.

In some embodiments of the tablet, the methanesulfonic acid or an anion thereof, and the compound of Formula I or a cation thereof, are present in the tablet in a molar ratio of the methanesulfonic acid or an anion thereof, to the compound of Formula I or a cation thereof, of at least 1:1, or between 1:1 and 3.3:1, between 1.9:1 and 3.3:1, between 1.9:1 and 2.5:1, between 1.9:1 and 2.4:1, between 2:1 to 3.3:1, between 2:1 and 3:1, or between 2:1 and 2.7:1, or between 2.1:1 and 2.5:1, or between 2.2:1 and 2.4:1, or about 2.3:1, or about 2.4:1. In another variation, the molar ratio of the methanesulfonic acid or an anion thereof, to the compound of Formula I or a cation thereof, is greater than 1:1 and less than 2:1. In yet another variation, the molar ratio of the methanesulfonic acid or an anion thereof, to the compound of Formula I or a cation thereof, is greater than 2:1.

In certain embodiments of the tablet, at least one pharmaceutically acceptable carrier is a precipitation inhibitor. The precipitation inhibitor in the spray-dried solid dispersion tablet may include any of the precipitation inhibitors described above. In one variation, the precipitation inhibitor is hydroxypropylmethylcellulose (HPMC). In another variation, the precipitation inhibitor is copovidone.

In other variations of the tablet, at least one pharmaceutically acceptable carrier is a non-ionic polymer. Suitable non-ionic polymers may include, for example, hydroxypropylmethylcellulose, copovidone, povidone, methyl cellulose, hydroxyethylcellulose, hydroxypropylcellulose, ethylcellulose, pyroxylin, polyethylene oxide, polyvinyl alcohol, polyethylene glycol, and polyvinyl caprolactam-polyvinyl acetate-polyethylene glycol.

In other variations of the tablet, at least one pharmaceutically acceptable carrier is an ionic polymer. Suitable ionic polymers may include, for example, hydroxypropylmethylcellulose acetate-succinate, hydroxypropylmethylcellulose phthalate, cellulose acetate phthalate, and methacrylic acid copolymers.

In some embodiments, the tablet comprises a polymer matrix obtainable from the at least one pharmaceutically acceptable polymer (e.g., hydroxypropylmethylcellulose). In one variation, the spray-dried solid dispersion tablet comprises a polymer matrix obtainable from the hydroxypropylmethylcellulose and a surfactant. In certain embodiments, the compound of Formula I or a cation thereof, and the methanesulfonic acid or an anion thereof, are dispersed within the polymer matrix.

A skilled artisan would further recognize that the amounts of components used in the formulation may vary, depending on the method and technique used.

In certain variations, the pharmaceutical composition is a tablet (e.g., a tablet prepared by spray drying a compound of Formula I or a pharmaceutically acceptable salt or hydrate thereof, and dry granulating and compressing the resulting solid dispersion) comprising a mono-mesylate or bis-mesylate salt of a compound of formula I, and at least one precipitation inhibitor. In one variation, the precipitation inhibitor is hydroxypropylmethylcellulose.

In another variation, the pharmaceutical composition is a tablet (e.g., a tablet prepared by spray drying a compound of Formula I or a pharmaceutically acceptable salt or hydrate thereof, and dry granulating and compressing the resulting solid dispersion) comprising a mono-mesylate or bis-mesylate salt of a compound of formula I, comprising at least one precipitation inhibitor, and at least one diluent.

In another variation, the pharmaceutical composition is a tablet (e.g., a tablet prepared by spray drying a compound of Formula I or a pharmaceutically acceptable salt or hydrate thereof, and dry granulating and compressing the resulting solid dispersion) comprising a mono-mesylate or bis-mesylate salt of a compound of formula I, at least one precipitation inhibitor, and at least one disintegrant.

In another variation, the pharmaceutical composition is a tablet (e.g., a tablet prepared by spray drying a compound of Formula I or a pharmaceutically acceptable salt or hydrate thereof, and dry granulating and compressing the resulting solid dispersion) comprising a mono-mesylate or bis-mesylate salt of a compound of Formula I, at least one precipitation inhibitor, and at least one surfactant.

In another variation, the pharmaceutical composition is a tablet (e.g., a tablet prepared by spray drying a compound of Formula I or a pharmaceutically acceptable salt or hydrate thereof, and dry granulating and compressing the resulting solid dispersion) comprising a mono-mesylate or bis-mesylate salt of a compound of formula I, at least one precipitation inhibitor, and at least one glidant.

In another variation, the pharmaceutical composition is a tablet (e.g., a tablet prepared by spray drying a compound of Formula I or a pharmaceutically acceptable salt or hydrate thereof, and dry granulating and compressing the resulting solid dispersion) comprising a mono-mesylate or bis-mesylate salt of a compound of Formula I, at least one precipitation inhibitor, and at least one lubricant.

In another variation, the pharmaceutical composition is a tablet (e.g., a tablet prepared by spray drying a compound of Formula I or a pharmaceutically acceptable salt or hydrate thereof, and dry granulating and compressing the resulting solid dispersion) comprising a mono-mesylate or bis-mesylate salt of a compound of Formula I, at least one precipitation inhibitor, at least one diluent, and at least surfactant.

In other embodiments, the pharmaceutical composition is a tablet (e.g., a tablet prepared by spray drying a compound of Formula I or a pharmaceutically acceptable salt or hydrate thereof, and dry granulating and compressing the resulting solid dispersion) comprising a mono-mesylate or bis-mesylate salt of a compound of Formula I, and (i) a non-ionic polymer, (ii) an ionic polymer, or a combination of (i) and (ii). In one variation, the non-ionic polymer is selected from the group consisting of hydroxypropylmethylcellulose, copovidone, povidone, methyl cellulose, hydroxyethylcellulose, hydroxypropylcellulose, ethylcellulose, pyroxylin, polyethylene oxide, polyvinyl alcohol, polyethylene glycol, and polyvinyl caprolactam-polyvinyl acetate-polyethylene glycol. In one variation, the ionic polymers is selected from the group consisting of hydroxypropylmethylcellulose acetate-succinate, hydroxypropylmethylcellulose phthalate, cellulose acetate phthalate, and methacrylic acid copolymers.

In one embodiment, the pharmaceutical composition is a tablet (e.g., a tablet prepared by spray drying a compound of Formula I or a pharmaceutically acceptable salt or hydrate thereof, and dry granulating and compressing the resulting solid dispersion) comprising a mono-mesylate or bis-mesylate salt of a compound of Formula I, hydroxypropylmethylcellulose, and a surfactant.

The pharmaceutical compositions provided in the present disclosure that are prepared by spray drying, followed by dry granulation and compression (e.g., a tablet prepared by spray drying a compound of Formula I or a pharmaceutically acceptable salt or hydrate thereof, and dry granulating and compressing the resulting solid dispersion) may comprise, in some embodiments, a mesylate salt of the compound of Formula I; or in certain embodiments, a mono-mesylate of the compound of Formula I; or in certain embodiments, a bis-mesylate salt of the compound of Formula I; or in certain embodiments, a bis-mesylate salt of Formula IA.

In other embodiments, the tablet (e.g., spray-dried solid dispersion tablet) is characterized by an X-ray diffraction pattern comprising 2θ-reflections (±0.2°) at 6.3 and between 26.1 to 26.6. In one variation, the spray-dried solid dispersion tablet is characterized by an X-ray diffraction pattern comprising 2θ-reflections at 6.3 (±0.2°) and between 26.1 to 26.6. It should be understood that ±0.2° can also be expressed as "plus or minus 0.2 degrees 2θ".

In some aspects, provided herein are methods of manufacturing a tablet, comprising: formulating a compound of Formula I, or a pharmaceutically acceptable salt thereof, or a hydrate thereof as a solid dispersion; and formulating the solid dispersion in the tablet as a dry granulation). In one variation, the tablet is prepared by a spray-dried solid dispersion (e.g., the solid dispersion is prepared by spray drying). Thus, in certain aspects, provided herein are methods of manufacturing a tablet, comprising: a) forming spray-dried powder from a feed solution; b) dry granulating the spray-dried powder and at least one pharmaceutically acceptable carrier to form a granulation; and c) compressing the granulation to form the tablet.

"Solid dispersion" refers to the dispersion of one or more active agents in a polymer matrix at solid state. The pharmaceutical compositions provided in the present disclosure that are formulated as a solid dispersion comprise, in some embodiments, a pharmaceutically acceptable salt of a compound of Formula I; or in certain embodiments, a mesylate salt of a compound of Formula I; or in certain embodiments, a mono-mesylate or bis-mesylate salt of a compound of Formula I; or in certain embodiments, the bis-mesylate salt of Formula IA. Thus, in some embodiments, the pharmaceutical compositions are tablets comprising a solid dispersion; or in certain embodiments, the pharmaceutical compositions are tablets comprising a spray-dried solid dispersion.

A skilled artisan would recognize suitable methods and techniques to prepare a solid dispersion and a tablet comprising such solid dispersion. Exemplary methods and techniques to prepare such solid dispersions include melt-extrusion, spray-drying, lyophilization, and solution-evaporation. In some embodiments, the solid dispersion is prepared by spray drying. For example, the mesylate salt (including, for example, the mono-mesylate or bis-mesylate salt) of a compound of Formula I and at least one pharmaceutically acceptable polymer (including, for example, HPMC) are dissolved, or at least partially dissolved, in water, and spray dried to form a solid dispersion. The solid dispersion may then be blended with other pharmaceutically acceptable carriers, and then dried granulated, followed by compression and coating. An exemplary manufacturing process for preparing a solid dispersion and tablet of the bis-mesylate salt of a compound of Formula I is described in Example C1 below.

In one aspect, provided herein is a method of manufacturing a tablet, comprising:

a) forming spray-dried powder from a feed solution, wherein the feed solution comprises: (i) a compound of Formula I, or a cation thereof; (ii) methanesulfonic acid, or an anion thereof; (iii) at least one pharmaceutically acceptable carrier; and (iv) water;

b) dry granulating the spray-dried powder and at least one pharmaceutically acceptable carrier to form a granulation; and c) compressing the granulation to form the tablet.

It should be understood that various forms of a compound of Formula I, or a salt or hydrate thereof, may be used to form the feed solution that is spray dried to manufacture solid dispersion particles. In certain embodiments, a compound of Formula I (e.g., as a free base), or a mono-mesylate or bis-mesylate salt of a compound of Formula I, or a hydrate thereof, or any combinations thereof, may be used to prepare the feed solution. For example, the starting material used for preparing the feed solution (e.g., for forming the solid dispersion) may include one or more forms of a mesylate salt of a compound of Formula I, or in certain embodiments, a bis-mesylate salt of Formula IA.

Provided is also a tablet (e.g., a spray-dried solid dispersion tablet) produced according to any of the foregoing methods.

Feed Solution

Provided herein are also methods of preparing feed solution for spray drying, comprising combining:
(i) either:
(A) a compound of Formula I and methanesulfonic acid; or
(B) a mesylate salt of a compound of Formula I, or a hydrate thereof;
(ii) at least one pharmaceutically acceptable carrier; and
(iii) water to form a feed solution.

In embodiments where the mesylate salt, or a hydrate thereof, is combined with the at least one pharmaceutically acceptable carrier and water to form the feed solution, the method further comprises combining methanesulfonic acid with the feed solution.

In one variation, the feed solution may be prepared by combining a compound of Formula I and methanesulfonic acid. In another variation, the feed solution may be prepared by combining a mesylate salt of a compound of Formula I and additional methanesulfonic acid. In one variation, the mesylate salt may be a mono-mesylate salt or a bis-mesylate salt, or a combination thereof. In another variation, the mesylate salt is a monohydrate, bis-mesylate salt of a compound of Formula I. In another variation, the mesylate salt is polymorph Form 3, a monohydrate, bis-mesylate salt of a compound of Formula I.

In some embodiments, the methanesulfonic acid, or an anion thereof, and the compound of Formula I, or a cation thereof, are present in the feed solution in a molar ratio of between 2:1 and 3:1, or between 2:1 and 2.7:1, or between 2.1:1 and 2.5:1, or between 2.2:1 and 2.4:1, or about 2.3:1, or about 2.4:1. In another variation, the molar ratio of the methanesulfonic acid or an anion thereof, to the compound of Formula I or a cation thereof, is greater than 1:1 and less than 2:1. In yet another variation, the molar ratio of the methanesulfonic acid or an anion thereof, to the compound of Formula I or a cation thereof, is greater than 2:1.

In other embodiments, the feed solution is prepared with at least 1% w/w, or between 1% w/w and 10% w/w, or about 5% w/w of the compound of Formula I, or a cation thereof.

In other embodiments, the compound of Formula I, or a cation thereof, and the water are present in the feed solution in a molar ratio of between 1:1 to 1:2, or about 1:1.5.

Spray-Dried Powder

The feed solution described herein may undergo spray drying to form a spray-dried powder, which is also known as a spray-dried solid dispersion.

Provided herein is also a spray-dried powder, comprising:
(i) a bis-mesylate salt of a compound of Formula I:

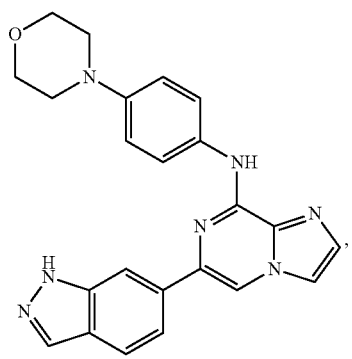

(I)

and
(ii) at least one pharmaceutically acceptable carrier.

In some embodiments of the spray-dried powder, the bis-mesylate salt is a bis-mesylate salt of the compound of Formula I.

In other embodiments, the spray-dried powder further comprises additional methanesulfonic acid, or an anion thereof.

In other aspects, provided herein is also a spray-dried powder, comprising:
(i) a mesylate salt of a compound of Formula I:

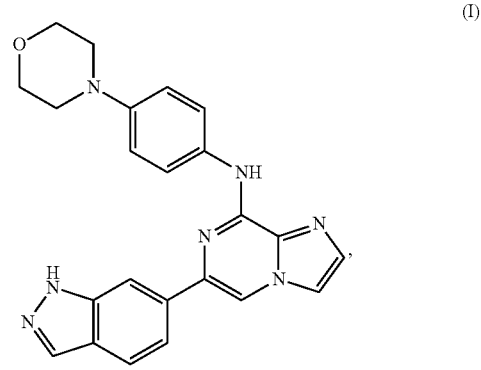 [SMILES: c1cn2cc(-c3ccc4cn[nH]c4c3)nc(Nc3ccc(N4CCOCC4)cc3)c2n1]

(I)

wherein the mesylate salt comprises a cation of the compound of Formula I and a mesylate anion; and
(ii) at least one pharmaceutically acceptable carrier.

In one variation of the foregoing aspect of the spray-dried powder, the molar ratio of the mesylate anion to the cation of the compound of Formula I is at least 1:1, or between 1:1 and 3.3:1, between 1.9:1 and 3.3:1, between 1.9:1 and 2.5:1, between 1.9:1 and 2.4:1, between 2:1 to 3.3:1, between 2:1 and 3:1, or between 2:1 and 2.7:1, or between 2.1:1 and 2.5:1, or between 2.2:1 and 2.4:1, or about 2.3:1, or about 2.4:1. In another variation, the molar ratio of the mesylate anion to the cation of the compound of Formula I is greater than 1:1 and less than 2:1. In yet another variation, the molar ratio of the mesylate anion to the cation of the compound of Formula I is greater than 2:1.

When such molar ratio in the spray-dried powder is greater than 2:1, the spray-dried powder was unexpectedly observed to exhibit improved stability. For example, improved stability may entail minimizing crystallization of the spray-dried powder (e.g., minimizing crystallization of the other polymorphic forms, such as Form 7 of the bis-mesylate salt of a compound of Formula I). For example, when such molar ratio is 2.3:1 or greater, for example, between 2.3:1 and 2.5:1, the spray-dried solid dispersion may remain stable for at least two months at room temperature and 75% relative humidity.

In yet other aspects, provided herein is a spray-dried powder comprising:

(i) a compound of Formula I:

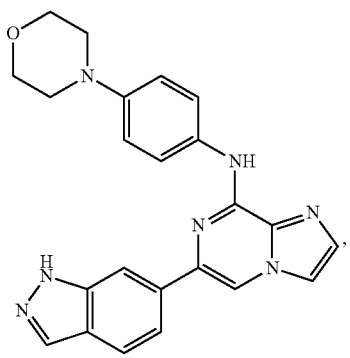

or a cation thereof;

(ii) methanesulfonic acid, or an anion thereof; and (iii) at least one pharmaceutically acceptable carrier.

In some embodiments of the foregoing aspect of the spray-dried powder, the methanesulfonic acid or an anion thereof, and the compound of Formula I or a cation thereof, are present in the spray-dried powder in a molar ratio between 2:1 and 3:1, or between 2:1 and 2.7:1, or between 2.1:1 and 2.5:1, or between 2.2:1 and 2.4:1, or about 2.3:1, or about 2.4:1. In another variation, the molar ratio of the methanesulfonic acid or an anion thereof, to the compound of Formula I or a cation thereof, is greater than 1:1 and less than 2:1. In yet another variation, the molar ratio of the methanesulfonic acid or an anion thereof, to the compound of Formula I or a cation thereof, is greater than 2:1.

In certain embodiments, the spray-dried powder is characterized by an X-ray diffraction pattern comprising 2θ-reflections (±0.2°) at 6.3 and between 26.1 to 26.6. It should be understood that ±0.2° can also be expressed as "plus or minus 0.2 degrees 2θ".

In certain embodiments of the spray-dried powder, at least one pharmaceutically acceptable carrier is a precipitation inhibitor. In one variation, the precipitation inhibitor is hydroxypropylmethylcellulose (HPMC). In another variation, the precipitation inhibitor is copovidone.

The spray-dried solid dispersion tablet is formed from the spray-dried powder by dry granulation and compression as described herein. For example, in certain embodiments, the spray-dried powder and pharmaceutically acceptable carriers are blended, dry granulated, milled, and compressed to form a tablet, which may be coated and packaged.

In some embodiments, upon formulating as a solid dispersion, the resulting active agent may be amorphous. Thus, in one variation, the pharmaceutical compositions described in the present disclosure comprises an amorphous active agent, where the term "amorphous active agent" refers to an amorphous solid dispersion contains inactive agent in a substantially amorphous solid state form. In another variation, active agent is dispersed with the polymer matrix, and the resulting solid dispersion may be an amorphous solid dispersion. The term "amorphous solid dispersion" as used herein, refers to stable solid dispersions comprising an amorphous active agent and a polymer.

In some embodiments, upon formulating as a solid dispersion, the resulting active agent may be non-crystalline. Thus, in some variations, the pharmaceutical compositions described in the present disclosure comprises a non-crystalline active agent, where the term "non-crystalline active agent" refers to an non-crystalline solid dispersion comprising an active agent in a substantially non-crystalline solid state form. In one variation, the pharmaceutical compositions described in the present disclosure comprises a non-crystalline compound of Formula I or a pharmaceutically acceptable salt thereof. In another variation, the term "non-crystalline active agent" may refer to a non-crystalline solid dispersion comprising a compound of Formula I or a pharmaceutically acceptable salt thereof in a substantially non-crystalline solid state form.

In other variations, active agent is dispersed with the polymer matrix, and the resulting solid dispersion may be a non-crystalline solid dispersion. The term "non-crystalline solid dispersion" as used herein, refers to stable solid dispersions comprising an non-crystalline active agent and a polymer. In one variation, a compound of Formula I or a pharmaceutically acceptable salt thereof is dispersed with the polymer matrix. In another variation, the term "non-crystalline solid dispersion" may refer to stable solid dispersions comprising a non-crystalline compound of Formula I or a pharmaceutically acceptable salt thereof and a polymer. In certain variations, both the compound of Formula I or a pharmaceutically acceptable salt thereof and the polymer may be substantially non-crystalline.

Provided is also a tablet produced according to such methods described above. In some variations, the tablets provided herein are formulated with a mean solid dispersion particle size between 1 μm to 100 μm, or between 1 μm to 75 μm, or between 5 μm to 50 μm, which may be beneficial for production of dry granulations and tablets. In certain embodiments, the tablets provided herein are formulated with a solid dispersion with bulk density between 0.1 g/mL to 0.7 g/mL, or between 0.15 g/mL to 0.4 g/mL, or between 0.2 g/mL to 0.35 g/mL, which may be beneficial for production of dry granulations and tablets. In certain embodiments, the tablets provided herein are formulated with a solid dispersion with tap density between 0.1 g/mL to 0.7 g/mL, or between 0.15 g/mL to 0.4 g/mL, or between 0.2 g/mL to 0.35 g/mL, which may be beneficial for production of dry granulations and tablets. In certain embodiments, the tablets provided herein are formulated with a solid dispersion with a $T_g$ of between 120° C. to 175° C., or between 130° C. to 150° C., or between 135° C. to 140° C., which may be beneficial for production of dry granulations and tablets.

Unit Dosage Forms

In some embodiments, the compositions as described herein are pharmaceutical compositions formulated in a unit dosage form. In some embodiments, the unit dosage form is a tablet. The term "unit dosage forms" refers to physically discrete units suitable as unitary dosages for subjects (e.g., human subjects and other mammals), each unit containing a predetermined quantity of active material calculated to produce the desired therapeutic effect, in association with a suitable pharmaceutical carrier. A pharmaceutically acceptable salt (such as a mesylate salt) of a compound of Formula I, or a hydrate thereof (including a bis-mesylate salt of Formula IA or a hydrate thereof), may be administered in a pharmaceutically effective amount. In some embodiments, each dosage unit contains from 1 mg to 2 g of a mesylate salt of a compound of Formula I or a hydrate thereof, or in certain embodiments, of a mono-mesylate or bis-mesylate salt of a compound of Formula I, or a hydrate thereof.

In some embodiments, the unit dosage form comprises from about 10 mg to about 1800 mg, or about 10 mg to about 1500 mg, or about 10 mg to about 1300 mg, or about 10 mg to about 1000 mg, or about 10 mg to about 800 mg, or about 10 mg to about 600 mg, or about 10 mg to about 300 mg, or about 10 mg to about 200 mg, or about 10 mg to about 100 mg, or about 100 mg to about 800 mg, or about 100 mg to about 600 mg, or about 100 mg to about 300 mg, or about 100 mg to about 200 mg, or about 200 mg to about 350 mg, or about 250 mg to about 300 mg, or about 200 mg to about 400 mg, or about 400 mg to about 600 mg, or about 400 mg to about 800 mg, or about 600 mg to about 800 mg, or about 800 mg to about 1200 mg, or about 1200 mg to about 1600 of a mesylate salt of a compound of Formula I, or a hydrate thereof; or in certain embodiments, of a mono-mesylate or bis-mesylate salt of a compound of Formula I, a hydrate thereof; or in one embodiment, of a monohydrate, bis-mesylate salt of a compound of Formula I; or in another embodiment, polymorph Form 3, polymorph Form 7, or a combination thereof. In certain embodiments, the unit dosage form comprises about 25 mg, about 50 mg, about 75 mg, about 100 mg, about 200 mg, about 250 mg, about 300 mg, about 350 mg, about 400 mg, about 450 mg, about 500 mg, about 550 mg, about 600 mg, about 700 mg, about 800 mg, about 900 mg, about 1000 mg, about 1100 mg, about 1200 mg, or about 1300 mg of a mesylate salt of a compound of Formula I, or a hydrate thereof; or in certain embodiments, of a mono-mesylate or bis-mesylate salt of a compound of Formula I, a hydrate thereof; or in one embodiment, of a monohydrate, bis-mesylate salt of a compound of Formula I; or in another embodiment, polymorph Form 3, polymorph Form 7, or a combination thereof.

In one variation, the unit dosage form is a spray-dried solid dispersion tablet comprising from about 10 mg to about 1800 mg, or about 10 mg to about 1500 mg, or about 10 mg to about 1300 mg, or about 10 mg to about 1000 mg, or about 10 mg to about 800 mg, or about 10 mg to about 600 mg, or about 10 mg to about 300 mg, or about 10 mg to about 200 mg, or about 10 mg to about 100 mg, or about 100 mg to about 800 mg, or about 100 mg to about 600 mg, or about 100 mg to about 300 mg, or about 100 mg to about 200 mg, or about 200 mg to about 350 mg, or about 250 mg to about 300 mg, or about 200 mg to about 400 mg, or about 400 mg to about 600 mg, or about 400 mg to about 800 mg, or about 600 mg to about 800 mg, or about 800 mg to about 1200 mg, or about 1200 mg to about 1600 of a mesylate salt of a compound of Formula I; or in certain embodiments, of a mono-mesylate or bis-mesylate salt of a compound of Formula I. In certain embodiments, the unit dosage form is a spray-dried solid dispersion tablet comprising about 25 mg, about 50 mg, about 75 mg, about 100 mg, about 200 mg, about 250 mg, about 300 mg, about 350 mg, about 400 mg, about 450 mg, about 500 mg, about 550 mg, about 600 mg, about 700 mg, about 800 mg, about 900 mg, about 1000 mg, about 1100 mg, about 1200 mg, or about 1300 mg of a mesylate salt of a compound of Formula I; or in certain embodiments, of a mono-mesylate or bis-mesylate salt of a compound of Formula I.

In some of the foregoing embodiments, the unit dosage form further comprises at least one pharmaceutically acceptable carrier.

The dosages for oral administration described above may be administered once daily (QD) or twice daily (BID). In some embodiments, a mesylate salt of a compound of Formula I, or a hydrate thereof; or in certain embodiments, a mono-mesylate or bis-mesylate salt of a compound of Formula I, a hydrate thereof; or in one embodiment, a monohydrate, bis-mesylate salt of a compound of Formula I; or in another embodiment, polymorph Form 3, polymorph Form 7, or a combination thereof, or a pharmaceutical composition of any of the foregoing, is administered orally at a unit dosage of about 1 mg QD, about 2 mg QD, about 5 mg QD, about 10 mg QD, about 15 mg QD, about 20 mg QD, about 25 mg QD, about 30 mg QD, about 35 mg QD, about 40 mg QD, about 45 mg QD, about 50 mg QD, about 75 mg QD, about 100 mg QD, about 125 mg QD, about 150 mg QD, about 175 mg QD, about 200 mg QD, about 225 mg QD, about 250 mg QD, about 300 mg QD, about 350 mg QD, about 400 mg QD, about 450 mg QD, about 500 mg QD, about 550 mg QD, about 600 mg QD, about 650 mg QD, about 700 mg QD, about 750 mg QD, about 800 mg QD, about 850 mg QD, about 900 mg QD, about 950 mg QD, or about 1000 mg QD. In some embodiments, a mesylate salt of a compound of Formula I, or a hydrate thereof; or in certain embodiments, a mono-mesylate or bis-mesylate salt of a compound of Formula I, a hydrate thereof; or in one embodiment, a monohydrate, bis-mesylate salt of a compound of Formula I; or in another embodiment, polymorph Form 3, polymorph Form 7, or a combination thereof, or a pharmaceutical composition of any of the foregoing, is administered orally at a unit dosage of about 1 mg BID, about 2 mg BID, about 5 mg BID, about 10 mg BID, about 15 mg BID, about 20 mg BID, about 25 mg BID, about 30 mg BID, about 35 mg BID, about 40 mg BID, about 45 mg BID, about 50 mg BID, about 75 mg BID, about 100 mg BID, about 125 mg BID, about 150 mg BID, about 175 mg BID, about 200 mg BID, about 225 mg BID, about 250 mg BID, about 300 mg BID, about 350 mg BID, about 400 mg BID, about 450 mg BID, about 500 mg BID, about 550 mg BID, about 600 mg BID, about 650 mg BID, about 700 mg BID, about 750 mg BID, about 800 mg BID, about 850 mg BID, about 900 mg BID, about 950 mg BID, or about 1000 mg BID.

In some variations, the unit dosage form is prepared by formulating a compound of Formula I, or a pharmaceutically acceptable salt thereof, or a hydrate thereof, as a granulation. In certain variations, the unit dosage form is prepared by formulating a mesylate salt of a compound of Formula I, or a pharmaceutically acceptable salt thereof, or a hydrate thereof, as a granulation. In certain variations, the unit dosage form is prepared by formulating a bis-mesylate salt of compound of Formula I, or a pharmaceutically acceptable salt thereof, or a hydrate thereof, as a granulation. In one variation, the unit dosage form is prepared by formulating a hydrate, bis-mesylate salt of compound of Formula I, or a pharmaceutically acceptable salt thereof, as a granulation. In another variation, the unit dosage form is prepared by formulating a monohydrate, bis-mesylate salt of compound of Formula I, or a pharmaceutically acceptable salt thereof, as a granulation. In yet another variation, the unit dosage form is prepared by formulating polymorph Form 3, polymorph Form 7, or a combination thereof, as a granulation. In other variations, the unit dosage form is prepared by formulating a mono-mesylate salt of a compound of Formula I, or a pharmaceutically acceptable salt thereof, or a hydrate thereof, as a granulation.

For example, in some variations, provided is a tablet comprising a mesylate salt of a compound of Formula I, or a hydrate thereof; or in certain embodiments, a mono-mesylate or bis-mesylate salt of a compound of Formula I, a hydrate thereof; or in one embodiment, a monohydrate, bis-mesylate salt of a compound of Formula I; or in another embodiment, polymorph Form 3, polymorph Form 7, or a combination thereof (e.g., formulated as a granulation), wherein the tablet is administered orally to a human in need thereof at a unit dosage of about 1 mg BID, about 2 mg BID, about 5 mg BID, about 10 mg BID, about 15 mg BID, about 20 mg BID, about 25 mg BID, about 30 mg BID, about 35 mg BID, about 40 mg BID, about 45 mg BID, about 50 mg BID, about 75 mg BID, about 100 mg BID, about 125 mg BID, about 150 mg BID, about 175 mg BID, about 200 mg BID, about 225 mg BID, about 250 mg BID, about 300 mg BID, about 350 mg BID, about 400 mg BID, about 450 mg BID, about 500 mg BID, about 550 mg BID, about 600 mg BID, about 650 mg BID, about 700 mg BID, about 750 mg BID, about 800 mg BID, about 850 mg BID, about 900 mg BID, about 950 mg BID, or about 1000 mg BID. In one variation of the foregoing, the human has a condition selected from the group consisting of lymphoplasmacytic lymphoma/Waldestrom's macroglobulinemia (LPL/WM), small lymphocytic lymphoma (SLL), marginal zone lymphoma (MZL), follicular lymphoma (FL), diffuse large B-cell lymphoma (DLBCL), mantle cell lymphoma (MCL), and chronic lymphocytic leukemia (CLL), or any combination thereof.

In another example, in other variations, provided is a tablet (e.g., a spray-dried solid dispersion tablet) comprising a mesylate salt of a compound of Formula I, and optionally additional methansulfonic acid; or in certain embodiments, a mono-mesylate or bis-mesylate salt of a compound of Formula I, and optionally additional methanesulfonic acid, wherein the tablet is administered orally to a human in need thereof at a unit dosage of about 1 mg BID, about 2 mg BID, about 5 mg BID, about 10 mg BID, about 15 mg BID, about 20 mg BID, about 25 mg BID, about 30 mg BID, about 35 mg BID, about 40 mg BID, about 45 mg BID, about 50 mg BID, about 75 mg BID, about 100 mg BID, about 125 mg BID, about 150 mg BID, about 175 mg BID, about 200 mg BID, about 225 mg BID, about 250 mg BID, about 300 mg BID, about 350 mg BID, about 400 mg BID, about 450 mg BID, about 500 mg BID, about 550 mg BID, about 600 mg BID, about 650 mg BID, about 700 mg BID, about 750 mg BID, about 800 mg BID, about 850 mg BID, about 900 mg BID, about 950 mg BID, or about 1000 mg BID. In one variation of the foregoing, the human has a condition selected from the group consisting of lymphoplasmacytic lymphoma/Waldestrom's macroglobulinemia (LPL/WM), small lymphocytic lymphoma (SLL), marginal zone lymphoma (MZL), follicular lymphoma (FL), diffuse large B-cell lymphoma (DLBCL), mantle cell lymphoma (MCL), and chronic lymphocytic leukemia (CLL), or any combination thereof. In another variation of any of the foregoing, the human is (i) refractory to, and/or (ii) in relapse after treatment with at least one therapy for a non-FL indolent non-Hodgkin's lymphoma. In certain embodiments, the non-FL indolent non-Hodgkin's lymphoma is lymphoplasmacytic lymphoma/Waldestrom's macroglobulinemia (LPL/WM), small lymphocytic lymphoma (SLL), or marginal zone lymphoma (MZL)). In another variation, the human is (i) refractory to, and/or (ii) in relapse after treatment with at least one therapy for follicular lymphoma (FL). In another variation, the human is (i) refractory to, and/or (ii) in relapse after treatment with at least one therapy for diffuse large B-cell lymphoma (DLBCL). In another variation, the human is (i) refractory to, and/or (ii) in relapse after treatment with at least one therapy for mantle cell lymphoma (MCL). In yet another variation, the human is (i) refractory to, and/or (ii) in relapse after treatment with at least one therapy for chronic lymphocytic leukemia (CLL). In yet another variation, the human is (i) refractory to, and/or (ii) in relapse after treatment with a phosphatidylinositol 3-kinase (PI3K) inhibitor, a bruton tyrosine kinase (BTK) inhibitor, or a B-cell receptor (BCR) treatment for chronic lymphocytic leukemia (CLL).

In any of the foregoing variations, the unit dosage form comprises from about 250 mg to about 350 mg of a bis-mesylate salt of a compound of Formula I, or a hydrate thereof; from about 200 mg to about 250 mg mannitol; from about 50 mg to about 100 mg crospovidone; from about 10 mg to 25 mg hydroxypropylmethylcellulose; from about 1 mg to about 5 mg poloxamer; from about 0.5 mg to about 1.5 mg colloidal silicon dioxide; from about 1 mg to about 10 mg microcrystalline cellulose; and from about 1 mg to 2 mg magnesium stearate. In one variation, the bis-mesylate salt of a compound of Formula I, or a hydrate thereof, is crystalline.

In other variations, the unit dosage form comprises from about 250 mg to about 350 mg of a bis-mesylate salt of Formula IA; from about 200 mg to about 250 mg mannitol; from about 50 mg to about 100 mg crospovidone; from about 10 mg to 25 mg hydroxypropylmethylcellulose; from about 1 mg to about 5 mg poloxamer; from about 0.5 mg to about 1.5 mg colloidal silicon dioxide; from about 1 mg to about 10 mg microcrystalline cellulose; and from about 1 mg to 2 mg magnesium stearate. In one variation, the bis-mesylate salt is crystalline.

In other variations, the unit dosage form comprises from about 250 mg to about 350 mg of a monohydrate, bis-mesylate salt of a compound of Formula I; from about 200 mg to about 250 mg mannitol; from about 50 mg to about 100 mg crospovidone; from about 10 mg to 25 mg hydroxypropylmethylcellulose; from about 1 mg to about 5 mg poloxamer; from about 0.5 mg to about 1.5 mg colloidal silicon dioxide; from about 1 mg to about 10 mg microcrystalline cellulose; and from about 1 mg to 2 mg magnesium stearate. In one variation, the monohydrate, bis-mesylate salt of the compound of Formula I is crystalline.

In other variations, the unit dosage form comprises from about 250 mg to about 350 mg of a polymorph of a monohydrate, bis-mesylate salt of a compound of Formula I, or a hydrate thereof; from about 200 mg to about 250 mg mannitol; from about 50 mg to about 100 mg crospovidone; from about 10 mg to 25 mg hydroxypropylmethylcellulose; from about 1 mg to about 5 mg poloxamer; from about 0.5 mg to about 1.5 mg colloidal silicon dioxide; from about 1 mg to about 10 mg microcrystalline cellulose; and from about 1 mg to 2 mg magnesium stearate. In one variation, the bis-mesylate salt is crystalline. In certain variations of the foregoing, the polymorph is polymorph Form 3, polymorph Form 7, or a mixture thereof.

In other variations, the unit dosage form is prepared by formulating a compound of Formula I, or a pharmaceutically acceptable salt thereof, or a hydrate thereof, as a solid dispersion, and formulating the solid dispersion in the unit dosage form as a dry granulation. In certain variations, the unit dosage form is prepared by formulating a mesylate salt of a compound of Formula I, or a pharmaceutically acceptable salt thereof, or a hydrate thereof, as a solid dispersion, and formulating the solid dispersion in the unit dosage form as a dry granulation. In certain variations, the unit dosage form is prepared by formulating a bis-mesylate salt of compound of Formula I, or a pharmaceutically acceptable salt thereof, or a hydrate thereof, as a solid dispersion, and formulating the solid dispersion in the unit dosage form as a dry granulation. In one variation, the unit dosage form is prepared by formulating a hydrate, bis-mesylate salt of compound of Formula I, or a pharmaceutically acceptable salt thereof, as a solid dispersion, and formulating the solid dispersion in the unit dosage form as a dry granulation. In another variation, the unit dosage form is prepared by formulating a monohydrate, bis-mesylate salt of compound of Formula I, or a pharmaceutically acceptable salt thereof, as a solid dispersion, and formulating the solid dispersion in the unit dosage form as a dry granulation, and formulating the solid dispersion in the unit dosage form as a dry granulation. In yet another variation, the unit dosage form is prepared by formulating polymorph Form 3, polymorph Form 7, or a combination thereof, as a solid dispersion, and formulating the solid dispersion in the unit dosage form as a dry granulation. In other variations, the unit dosage form is prepared by formulating a mono-mesylate salt of a compound of Formula I, or a pharmaceutically acceptable salt thereof, or a hydrate thereof, as a solid dispersion, and formulating the solid dispersion in the unit dosage form as a dry granulation. In any of the foregoing variations, the solid dispersion is a spray-dried solid dispersion.

In some variations, where the unit dosage form incorporates a spray-dried solid dispersion, the unit dosage comprises from about 250 mg to about 350 mg of a compound of Formula I or a pharmaceutically acceptable salt thereof; from about 200 mg to about 250 mg mannitol; from about 75 mg to about 150 mg crospovidone; from about 20 mg to 40 mg hydroxypropylmethylcellulose; from about 25 mg to about 35 mg poloxamer; from about 5 mg to about 15 mg colloidal silicon dioxide; from about 25 mg to about 35 mg microcrystalline cellulose; and from about 10 mg to 15 mg magnesium stearate.

In other variations, where the unit dosage form incorporates a spray-dried solid dispersion, the unit dosage comprises from about 250 mg to about 350 mg of a mesylate salt of a compound of Formula I; from about 200 mg to about 250 mg mannitol; from about 75 mg to about 150 mg crospovidone; from about 20 mg to 40 mg hydroxypropylmethylcellulose; from about 25 mg to about 35 mg poloxamer; from about 5 mg to about 15 mg colloidal silicon dioxide; from about 25 mg to about 35 mg microcrystalline cellulose; and from about 10 mg to 15 mg magnesium stearate.

In certain variations, where the unit dosage form incorporates a spray-dried solid dispersion, the unit dosage comprises from about 250 mg to about 350 mg of a bis-mesylate salt of a compound of Formula I; from about 200 mg to about 250 mg mannitol; from about 75 mg to about 150 mg crospovidone; from about 20 mg to 40 mg hydroxypropylmethylcellulose; from about 25 mg to about 35 mg poloxamer; from about 5 mg to about 15 mg colloidal silicon dioxide; from about 25 mg to about 35 mg microcrystalline cellulose; and from about 10 mg to 15 mg magnesium stearate.

In yet another variation, where the unit dosage form incorporates a spray-dried solid dispersion, the unit dosage comprises from about 250 mg to about 350 mg of a bis-mesylate salt of Formula IA (including amorphous salt form); from about 200 mg to about 250 mg mannitol; from about 75 mg to about 150 mg crospovidone; from about 20 mg to 40 mg hydroxypropylmethylcellulose; from about 25 mg to about 35 mg poloxamer; from about 5 mg to about 15 mg colloidal silicon dioxide; from about 25 mg to about 35 mg microcrystalline cellulose; and from about 10 mg to 15 mg magnesium stearate.

In any of the foregoing variations, where the unit dosage form incorporates a spray-dried solid dispersion, the compound or salt thereof is non-crystalline.

It should be understood that unit dosage actually administered to a subject (e.g., a human) usually will be determined by a physician, in the light of the relevant circumstances, including the condition to be treated, the chosen route of administration, the actual compound administered and its relative activity, the age, weight and response of the individual subject, the severity of the subject's symptoms, and the like.

Methods of Use

Provided is also the use of the pharmaceutical compositions (including, for example, the tablets and unit dosage forms) described in the present disclosure to selectively or specifically inhibit Syk activity therapeutically or prophylactically. The method comprises administering the pharmaceutical composition to an individual in need thereof in an amount sufficient to inhibit Syk activity. The method can be employed to treat subjects (e.g., humans) suffering from, or subject to, a condition whose symptoms or pathology is mediated by Syk expression or activity.

In one aspect, provided is a method of treating a human in need thereof, comprising administering the pharmaceutical compositions (including, for example, the tablets and unit dosage forms) described herein to the human.

"Treatment" or "treating" is an approach for obtaining beneficial or desired results including clinical results. Beneficial or desired clinical results may include one or more of the following:

a) inhibiting the disease or condition (e.g., decreasing one or more symptoms resulting from the disease or condition, and/or diminishing the extent of the disease or condition);

b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" of the pharmaceutical composition means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of Syk activity. The therapeutically effective amount may vary depending on the subject, and disease or condition being treated, the weight and age of the subject, the severity of the disease or condition, and the manner of administering, which can readily be determined by one or ordinary skill in the art.

The term "inhibition" indicates a decrease in the baseline activity of a biological activity or process. "Inhibition of activity of Syk activity" refers to a decrease in activity of Syk as a direct or indirect response to the presence of the pharmaceutical composition, relative to the activity of Syk in the absence of such pharmaceutical composition. In some embodiments, the inhibition of Syk activity may be compared in the same subject prior to treatment, or other subjects not receiving the treatment.

In certain aspects, the pharmaceutical compositions (including, for example, the tablets and unit dosage forms) described herein are used for treating a subject having cancer, an allergic disorder and/or an autoimmune and/or inflammatory disease, and/or an acute inflammatory reaction.

In one aspect, the pharmaceutical compositions (including, for example, the tablets and unit dosage forms) described herein may be used in the treatment of cancer. In some embodiments, the polymorphs and compositions thereof described herein can be employed in methods of inhibiting the growth or proliferation of cancer cells of hematopoietic origin, such as cancer cells. In some embodiments, the cancer cells are of lymphoid origin, and in specific embodiments, the cancer cells are related to or derived from B lymphocytes or B lymphocyte progenitors.

Cancers amenable to treatment using the method disclosed in the present disclosure include, without limitation, lymphomas (e.g., malignant neoplasms of lymphoid and reticuloendothelial tissues, such as Burkitt's lymphoma, Hodgkins' lymphoma, non-Hodgkins' lymphomas, lymphocytic lymphomas); multiple myelomas; leukemias (e.g., lymphocytic leukemias, chronic myeloid (myelogenous) leukemias). Other cancer cells, of hematopoietic origin or otherwise, that express spleen tyrosine kinase (Syk) also can be treated by administration of the polymorphs and compositions thereof described herein.

In particular embodiments of the methods provided herein, the cancer is leukemia or lymphoma. In certain embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), indolent non-Hodgkin's lymphoma (iNHL), refractory iNHL, non-Hodgkin's lymphoma (NHL), mantle cell lymphoma (MCL), follicular lymphoma (FL), Waldestrom's macroglobulinemia (WM), T-cell lymphoma, B-cell lymphoma, diffuse large B-cell lymphoma (DLBCL), lymphoplasmacytic lymphoma (LPL), and marginal zone lymphoma (MZL). In certain variations, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), indolent non-Hodgkin's lymphoma (iNHL), refractory iNHL, non-Hodgkin's lymphoma (NHL), mantle cell lymphoma (MCL), follicular lymphoma (FL), Waldestrom's macroglobulinemia (WM), T-cell lymphoma, B-cell lymphoma, and diffuse large B-cell lymphoma (DLBCL). In one embodiment, the cancer is T-cell acute lymphoblastic leukemia (T-ALL), or B-cell acute lymphoblastic leukemia (B-ALL). The non-Hodgkin lymphoma encompasses the indolent B-cell diseases that include, for example, follicular lymphoma, lymphoplasmacytic lymphoma, Waldenstrom macroglobulinemia, and marginal zone lymphoma, as well as the aggressive lymphomas that include, for example, Burkitt lymphoma, diffuse large B-cell lymphoma (DLBCL) and mantle cell lymphoma (MCL). In one embodiment, the cancer is indolent non-Hodgkin's lymphoma (iNHL). In yet another embodiment, the cancer is non-FL iNHL.

In particular embodiments of the methods provided herein, the cancer is a hematologic malignancy. In certain embodiments, the hematologic malignancy is leukemia (e.g., chronic lymphocytic leukemia) or lymphoma (e.g., non-Hodgkin's lymphoma). In some variations, the cancer is MCL, DLBCL, iNHL, FL, MZL, LPL, SLL, or WM. In other variations, the cancer is CLL, MCL, DLBCL, iNHL (including, for example, non-FL iNHL), or FL.

In other embodiments, the cancer is a solid tumor cancer (or solid cancer tumor). In certain embodiments the cancer is a solid tumor and expresses spleen tyrosine kinase (Syk) activity. In other embodiments, the solid tumor cancer is selected from the group consisting of pancreatic cancer, lung cancer, colon cancer, colo-rectal cancer, breast cancer, esophageal cancer, adenocarcinoma, hepatocellular cancer. In one embodiment, the solid tumor cancer is selected from the group consisting of pancreatic cancer, lung cancer, colorectal cancer, ovarian cancer, and hepatocellular cancer.

Any of the methods of treatment provided herein may be used to treat cancer at an advanced stage. Any of the methods of treatment provided herein may be used to treat cancer at locally advanced stage. Any of the methods of treatment provided herein may be used to treat early stage cancer. Any of the methods of treatment provided herein may be used to treat cancer in remission. In some of the embodiments of any of the methods of treatment provided herein, the cancer has reoccurred after remission. In some embodiments of any of the methods of treatment provided herein, the cancer is progressive cancer.

In some embodiments, the conditions and diseases that can be affected using the compounds and the compositions described herein, include, but are not limited to: allergic disorders, including but not limited to eczema, allergic rhinitis or coryza, hay fever, bronchial asthma, urticaria (hives) and food allergies, and other atopic conditions; autoimmune and/or inflammatory diseases, including but not limited to psoriasis, ulcerative colitis, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic obstructive pulmonary disease (COPD), adult respiratory distress syndrome (ARDS), chronic Idiopathic thrombocytopenic purpura (ITP), Addison's disease, Parkinson's disease, Alzheimer's disease, diabetes, septic shock, and myasthenia gravis; acute inflammatory reactions, including but not limited to skin sunburn, inflammatory pelvic disease, inflammatory bowel disease, urethritis, uvitis, sinusitis, pneumonitis, encephalitis, meningitis, myocarditis, nephritis, osteomyelitis, myositis, hepatitis gastritis, enteritis, dermatitis, gingivitis, appendicitis, pancreatitis, and cholocystitis; polycystic kidney disease.

In some embodiments, provided are also the use of the compounds and compositions described herein in the treatment of an autoimmune disease. Certain embodiments of an autoimmune disease include asthma, rheumatoid arthritis, multiple sclerosis, and lupus.

In yet another aspect, provided are methods of treating an individual having a Syk-mediated disorder by administering the pharmaceutical compositions (including, for example, the tablets and unit dosage forms) described herein to the individual. Provided are also methods of modulating Syk in an individual by administering the pharmaceutical compositions (including, for example, the tablets and unit dosage forms) described herein to the individual.

In some of the foregoing methods, the pharmaceutical compositions provided in the present disclosure may be administered to the individual as unit dosage, for example in the form of a tablet.

Subjects

Any of the methods of treatment provided may be used to treat a subject who has been diagnosed with or is suspected of having a cancer, an allergic disorder and/or an autoimmune and/or inflammatory disease, and/or an acute inflammatory reaction.

In some of the embodiments of any of the methods provided herein, the subject is a human who is at risk of developing a cancer (e.g., a human who is genetically or otherwise predisposed to developing a cancer) and who has or has not been diagnosed with the cancer. As used herein, an "at risk" subject is a subject who is at risk of developing cancer (e.g., a hematologic malignancy). The subject may or may not have detectable disease, and may or may not have displayed detectable disease prior to the treatment methods described herein. An at risk subject may have one or more so-called risk factors, which are measurable parameters that correlate with development of cancer, such as described herein. A subject having one or more of these risk factors has a higher probability of developing cancer than an individual without these risk factor(s).

These risk factors may include, for example, age, sex, race, diet, history of previous disease, presence of precursor disease, genetic (e.g., hereditary) considerations, and environmental exposure. In some embodiments, a subject at risk for cancer includes, for example, a subject whose relatives have experienced this disease, and those whose risk is determined by analysis of genetic or biochemical markers. Prior history of having cancer may also be a risk factor for instances of cancer recurrence.

Provided herein are also methods for treating a subject (e.g., a human) who exhibits one or more symptoms associated with cancer (e.g., a hematologic malignancy). In some embodiments, the subject is at an early stage of cancer. In other embodiments, the subject is at an advanced stage of cancer.

In some embodiments, the subject (e.g., a human) has a cancer responsive to Syk activity. In another embodiment, the human has a solid cancer tumor which expresses Syk. In some embodiments, the human has a 17p deletion, a TP53 mutation, NOTCH1, a SF3B1 mutation, a 11q deletion, or any combination thereof. In one embodiment, the human has a 17p deletion, a TP53 mutation, or a combination thereof. In another embodiment, the human has NOTCH1, a SF3B1 mutation, a 11q deletion, or any combination thereof.

Provided herein are also methods for treating a subject (e.g., a human) who is undergoing one or more standard therapies for treating cancer (e.g., a hematologic malignancy), such as chemotherapy, radiotherapy, immunotherapy, and/or surgery. Thus, in some foregoing embodiments, the pharmaceutical compositions (including, for example, the tablets and unit dosage forms) described herein may be administered before, during, or after administration of chemotherapy, radiotherapy, immunotherapy, and/or surgery.

In another aspect, provided herein are methods for treating a subject (e.g., a human) who is "refractory" to a cancer treatment or who is in "relapse" after treatment for cancer (e.g., a hematologic malignancy). A subject "refractory" to an anti-cancer therapy means they do not respond to the particular treatment, also referred to as resistant. The cancer may be resistant to treatment from the beginning of treatment, or may become resistant during the course of treatment, for example after the treatment has shown some effect on the cancer, but not enough to be considered a remission or partial remission. A subject in "relapse" means that the cancer has returned or the signs and symptoms of cancer have returned after a period of improvement, e.g. after a treatment has shown effective reduction in the cancer, such as after a subject is in remission or partial remission.

In some embodiments, the subject may be a human who is (i) refractory to at least one anti-cancer therapy, or (ii) in relapse after treatment with at least one anti-cancer therapy, or both (i) and (ii). In some of embodiments, the subject is refractory to at least two, at least three, or at least four anti-cancer therapy (including, for example, standard or experimental chemotherapies). In other embodiments, the subject may be a human who has prior exposure to at least one anti-cancer therapy.

In certain embodiments, the subject is a human who (i) is refractory to, and/or (ii) is in relapse after treatment with, and/or (iii) has prior exposure to at least one therapy for chronic lymphocytic leukemia (CLL), mantle cell lymphoma (MCL), diffuse large B-cell lymphoma (DLBCL), follicular lymphoma (FL), or non-FL indolent non-Hodgkin's lymphoma (including, for example, lymphoplasmacytic lymphoma/Waldestrom's macroglobulinemia (LPL/WM), small lymphocytic lymphoma (SLL), and marginal zone lymphoma (MZL)).

In some variations, the subject is a human who (i) is refractory to, and/or (ii) is in relapse after treatment with, and/or (iii) has prior exposure to at least one therapy for a non-FL indolent non-Hodgkin's lymphoma. In certain embodiments, the non-FL indolent non-Hodgkin's lymphoma is lymphoplasmacytic lymphoma/Waldestrom's macroglobulinemia (LPL/WM), small lymphocytic lymphoma (SLL), or marginal zone lymphoma (MZL)). In another variation, the subject is a human who (i) is refractory to, and/or (ii) is in relapse after treatment with, and/or (iii) has prior exposure to at least one therapy for follicular lymphoma (FL). In another variation, the subject is a human who (i) is refractory to, and/or (ii) is in relapse after treatment with, and/or (iii) has prior exposure to at least one therapy for diffuse large B-cell lymphoma (DLBCL). In another variation, the subject is a human who (i) is refractory to, and/or (ii) is in relapse after treatment with, and/or (iii) has prior exposure to at least one therapy for mantle cell lymphoma (MCL). In yet another variation, the subject is a human who (i) is refractory to, and/or (ii) is in relapse after treatment with, and/or (iii) has prior exposure to at least one therapy for chronic lymphocytic leukemia (CLL). In yet another variation, the subject is a human who (i) is refractory to, and/or (ii) is in relapse after treatment with, and/or (iii) has prior exposure to a phosphatidylinositol 3-kinase (PI3K) inhibitor, a bruton tyrosine kinase (BTK) inhibitor, or a B-cell receptor (BCR) treatment for chronic lymphocytic leukemia (CLL).

In some embodiments, the subject is refractory to at least one, at least two, at least three, or at least four anti-cancer therapy (including, for example, standard or experimental chemotherapy) selected from fludarabine, rituximab, obinutuzumab, alkylating agents, alemtuzumab and other chemotherapy treatments such as CHOP (cyclophosphamide, doxorubicin, vincristine, prednisone); R-CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar®) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D.T. PACE (dexamethasone, thalidomide, cisplatin, Adriamycin®, cyclophosphamide, etoposide).

Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" The

*New England Journal of Medicine* 2008, 359(6), p. 613-626; and Wierda, W. G., "Current and Investigational Therapies for Patients with CLL" *Hematology* 2006, p. 285-294. Lymphoma incidence patterns in the United States is profiled in Morton, L. M., et al. "Lymphoma Incidence Patterns by WHO Subtype in the United States, 1992-2001" *Blood* 2006, 107 (1), p. 265-276.

For example, treatment of non-Hodgkin's lymphomas (NHL), especially of B-cell origin, include the use of monoclonal antibodies, standard chemotherapy approaches (e.g., CHOP, CVP, FCM, MCP, and the like), radioimmunotherapy, and combinations thereof, especially integration of an antibody therapy with chemotherapy. Examples of unconjugated monoclonal antibodies for Non-Hodgkin's lymphoma/B-cell cancers include rituximab, alemtuzumab, human or humanized anti-CD20 antibodies, lumiliximab, anti-TRAIL, bevacizumab, galiximab, epratuzumab, SGN-40, and anti-CD74. Examples of experimental antibody agents used in treatment of Non-Hodgkin's lymphoma/B-cell cancers include ofatumumab, ha20, PRO131921, alemtuzumab, galiximab, SGN-40, CHIR-12.12, epratuzumab, lumiliximab, apolizumab, milatuzumab, and bevacizumab. Examples of standard regimens of chemotherapy for Non-Hodgkin's lymphoma/B-cell cancers include CHOP (cyclophosphamide, doxorubicin, vincristine, prednisone), FCM (fludarabine, cyclophosphamide, mitoxantrone), CVP (cyclophosphamide, vincristine and prednisone), MCP (mitoxantrone, chlorambucil, and prednisolone), R-CHOP (rituximab plus CHOP), R-FCM (rituximab plus FCM), R-CVP (rituximab plus CVP), and R-MCP (R-MCP). Examples of radioimmunotherapy for Non-Hodgkin's lymphoma/B-cell cancers include yttrium-90-labeled ibritumomab tiuxetan, and iodine-131-labeled tositumomab.

In another example, therapeutic treatments for mantle cell lymphoma (MCL) include combination chemotherapies such as CHOP (cyclophosphamide, doxorubicin, vincristine, prednisone), hyperCVAD (hyperfractionated cyclophosphamide, vincristine, doxorubicin, dexamethasone, methotrexate, cytarabine) and FCM (fludarabine, cyclophosphamide, mitoxantrone). In addition, these regimens can be supplemented with the monoclonal antibody rituximab (Rituxan) to form combination therapies R-CHOP, hyperCVAD-R, and R-FCM. Other approaches include combining any of the abovementioned therapies with stem cell transplantation or treatment with ICE (iphosphamide, carboplatin and etoposide). Other approaches to treating mantle cell lymphoma includes immunotherapy such as using monoclonal antibodies like Rituximab (Rituxan). Rituximab can be used for treating indolent B-cell cancers, including marginal-zone lymphoma, WM, CLL and small lymphocytic lymphoma. A modified approach is radioimmunotherapy, wherein a monoclonal antibody is combined with a radioisotope particle, such as Iodine-131 tositumomab (Bexxar®) and Yttrium-90 ibritumomab tiuxetan (Zevalin®). In another example, Bexxar® is used in sequential treatment with CHOP. Another immunotherapy example includes using cancer vaccines, which is based upon the genetic makeup of an individual subject's tumor. A lymphoma vaccine example is GTOP-99 (MyVax®). Yet other approaches to treating mantle cell lymphoma includes autologous stem cell transplantation coupled with high-dose chemotherapy, or treating mantle cell lymphoma includes administering proteasome inhibitors, such as Velcade® (bortezomib or PS-341), or antiangiogenesis agents, such as thalidomide, especially in combination with Rituxan. Another treatment approach is administering drugs that lead to the degradation of Bcl-2 protein and increase cancer cell sensitivity to chemotherapy, such as oblimersen (Genasense) in combination with other chemotherapeutic agents. Another treatment approach includes administering mTOR inhibitors, which can lead to inhibition of cell growth and even cell death; a non-limiting example is Temsirolimus (CCI-779), and Temsirolimus in combination with Rituxan®, Velcade® or other chemotherapeutic agents.

Other recent therapies for MCL have been disclosed (*Nature Reviews*; Jares, P. 2007). Such examples include Flavopiridol, PD0332991, R-roscovitine (Selicilib, CYC202), Styryl sulphones, Obatoclax (GX15-070), TRAIL, Anti-TRAIL DR4 and DR5 antibodies, Temsirolimus (CC1-779), Everolimus (RAD001), BMS-345541, Curcumin, Vorinostat (SAHA), Thalidomide, lenalidomide (Revlimid®, CC-5013), and Geldanamycin (17-AAG).

Examples of other therapeutic agents used to treat Waldenstrom's Macroglobulinemia (WM) include perifosine, bortezomib (Velcade®), rituximab, sildenafil citrate (Viagra®), CC-5103, thalidomide, epratuzumab (hLL2-anti-CD22 humanized antibody), simvastatin, enzastaurin, campath-1H, dexamethasone, DT PACE, oblimersen, antineoplaston A10, antineoplaston AS2-1, alemtuzumab, beta alethine, cyclophosphamide, doxorubicin hydrochloride, prednisone, vincristine sulfate, fludarabine, filgrastim, melphalan, recombinant interferon alfa, carmustine, cisplatin, cyclophosphamide, cytarabine, etoposide, melphalan, dolastatin 10, indium In 111 monoclonal antibody MN-14, yttrium Y 90 humanized epratuzumab, anti-thymocyte globulin, busulfan, cyclosporine, methotrexate, mycophenolate mofetil, therapeutic allogeneic lymphocytes, Yttrium Y 90 ibritumomab tiuxetan, sirolimus, tacrolimus, carboplatin, thiotepa, paclitaxel, aldesleukin, recombinant interferon alfa, docetaxel, ifosfamide, mesna, recombinant interleukin-12, recombinant interleukin-11, Bcl-2 family protein inhibitor ABT-263, denileukin diftitox, tanespimycin, everolimus, pegfilgrastim, vorinostat, alvocidib, recombinant flt3 ligand, recombinant human thrombopoietin, lymphokine-activated killer cells, amifostine trihydrate, aminocamptothecin, irinotecan hydrochloride, caspofungin acetate, clofarabine, epoetin alfa, nelarabine, pentostatin, sargramostim, vinorelbine ditartrate, WT-1 analog peptide vaccine, WT1 126-134 peptide vaccine, fenretinide, ixabepilone, oxaliplatin, monoclonal antibody CD19, monoclonal antibody CD20, omega-3 fatty acids, mitoxantrone hydrochloride, octreotide acetate, tositumomab and iodine I-131 tositumomab, motexafin gadolinium, arsenic trioxide, tipifarnib, autologous human tumor-derived HSPPC-96, veltuzumab, bryostatin 1, and PEGylated liposomal doxorubicin hydrochloride, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

Examples of other therapeutic agents used to treat diffuse large B-cell lymphoma (DLBCL) drug therapies (*Blood* 2005 Abramson, J.) include cyclophosphamide, doxorubicin, vincristine, prednisone, anti-CD20 monoclonal antibodies, etoposide, bleomycin, many of the agents listed for Waldenstrom's, and any combination thereof, such as ICE and R-ICE.

Examples of other therapeutic agents used to treat chronic lymphocytic leukemia (CLL) (Spectrum, 2006, Fernandes, D.) include Chlorambucil (Leukeran), Cyclophosphamide (Cyloxan, Endoxan, Endoxana, Cyclostin), Fludarabine (Fludara), Pentstatin (Nipent), Cladribine (Leustarin), Doxorubicin (Adriamycin®, Adriblastine), Vincristine (Oncovin), Prednisone, Prednisolone, Alemtuzumab (Campath, MabCampath), many of the agents listed for Waldenstrom's, and combination chemotherapy and chemoimmunotherapy, including the common combination regimen: CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); and FR (fludarabine, rituximab).

In another aspect, provided is a method of sensitizing a subject (e.g., a human) who is (i) refractory to at least one chemotherapy treatment, or (ii) in relapse after treatment with chemotherapy, or both (i) and (ii), wherein the method comprises administering the pharmaceutical compositions (including, for example, the tablets and unit dosage forms) described herein to the subject. A subject who is sensitized is a subject who is responsive to the treatment involving administration of the pharmaceutical compositions (including, for example, the tablets and unit dosage forms) described herein, or who has not developed resistance to such treatment.

In another aspect, provided herein are methods for treating a subject (e.g., a human) for a cancer, with comorbidity, wherein the treatment is also effective in treating the comorbidity. A "comorbidity" to cancer is a disease that occurs at the same time as the cancer.

In some embodiments, provided herein are methods for treating a subject (e.g., a human) for chronic lymphocytic leukemia (CLL), with comorbidity, wherein the treatment is also effective in treating the comorbidity. Many subjects with CLL will have one or more other diseases, for example diseases affecting the blood pressure system, vascular and heart systems, endocrine and metabolic systems, genitourinary system, musculoskeletal system, respiratory system, neurological system, upper and lower gastrointestinal systems, psychiatric system, ear, nose and throat systems, renal system, or liver system. Specific morbidities of CLL include, but are not limited to, one or more other cancers (e.g. breast, head and neck, lung, melanoma, non-Hodgkin's T-cell lymphoma, prostate, colon, small intestine, gynecologic and urinary tract), hypertension, hyperlipidemia, coronary artery disease, peripheral vascular diseases, cardiomyopathy, vulvular heart disease, atrial fibrillation, cerebrovascular disease (e.g. transient ischemic attack, stroke), chronic obstructive pulmonary disease, joint disease, peptic ulcer, inflammatory bowel disease, psychiatric illness, thyroid disease, benign prostate hyperplasia, diabetes mellitus, and osteoarthritis (Satram-Hoang et al., *Journal of Cancer Therapy,* 2013; 4:1321-1329; Thurmes et al., *Leukemia & Lymphoma,* 2008; 49(1):49-56).

In some embodiments, a method of treating a comorbidity of CLL in a subject (e.g., a human), wherein the method comprises administering the pharmaceutical compositions (including, for example, the tablets and unit dosage forms) described herein to the subject. In some embodiments, the comorbidity is selected from the group consisting of one or more other cancers (e.g. breast, head and neck, lung, melanoma, non-Hodgkin's T-cell lymphoma, prostate, colon, small intestine, gynecologic and urinary tract), hypertension, hyperlipidemia, coronary artery disease, peripheral vascular diseases, cardiomyopathy, vulvular heart disease, atrial fibrillation, cerebrovascular disease (e.g. transient ischemic attack, stroke), chronic obstructive pulmonary disease, joint disease, peptic ulcer, inflammatory bowel disease, psychiatric illness, thyroid disease, benign prostate hyperplasia, diabetes mellitus, and osteoarthritis.

Monotherapy and Combination Therapies

Provided are methods of treatment in which the pharmaceutical compositions (including, for example, the tablets and unit dosage forms) described herein are administered to a subject (e.g., a human), such that the mesylate salt (including, for example, a bis-mesylate salt) of a compound of Formula I, or a hydrate thereof, is the only therapeutic agent administered to the subject. Provided are also methods of treatment in which the pharmaceutical compositions (including, for example, the tablets and unit dosage forms) described herein administered to a subject (e.g., a human) are given to a subject (e.g., a human) in combination with one or more additional therapeutic agents or other therapies. Both monotherapy and combination therapies are intended and described for use in the methods detailed herein, such as in a method of treating any of the diseases or conditions detailed herein and for use with any subject detailed herein.

Monotherapy

In some embodiments, a method of treating cancer, an allergic disorder and/or an autoimmune and/or inflammatory disease, and/or an acute inflammatory reaction comprises administering to a subject in need thereof the pharmaceutical compositions (including, for example, the tablets and unit dosage forms) described herein, wherein the subject is not undergoing therapy for the same disease or condition with another agent or procedure.

In some embodiments where the pharmaceutical compositions (including, for example, the tablets and unit dosage forms) described herein are administered as a monotherapy to the subject who has been diagnosed with or is suspected of having a cancer, the subject may be a human who is (i) refractory to at least one anti-cancer therapy, or (ii) in relapse after treatment with at least one anti-cancer therapy, or both (i) and (ii). In some of embodiments, the subject is refractory to at least two, at least three, or at least four anti-cancer therapy (including, for example, standard or experimental chemotherapies). For example, in some embodiments, the subject may be a human who is (i) refractory to a therapy using an anti-CD20 antibody, an alkylating agent (e.g., bendamustine), a purine analog (e.g., fludarabine), an anthracycline, or any combination thereof; (ii) in relapse after treatment with an anti-CD20 antibody, an alkylating agent (e.g., bendamustine), a purine analog (e.g., fludarabine), an anthracycline, or any combination thereof, or both (i) and (ii).

A human subject who is refractory to at least one anti-cancer therapy and/or is in relapse after treatment with at least one anti-cancer therapy, as described above, may have undergone one or more prior therapies. In some embodiments, such subjects have undergone one, two, three, or four, or at least one, at least two, at least three, at least four, or at least five, or between one and ten, between one and nine, between one and eight, between one and seven, between one and six, between one and five, or between one and four, anti-cancer therapies prior to treatment using the methods described herein (e.g., prior to the administration of the pharmaceutical compositions (including, for example, the tablets and unit dosage forms) described herein as a monotherapy).

It should be understood that when a subject (e.g. a human) is treated with the compound of Formula I, or a pharmaceutically acceptable salt thereof, as a monotherapy, the subject may also undergo one or more other therapies that are not anti-cancer therapies.

In some embodiments, a method of treating a comorbidity of a cancer, including but not limited to CLL, in a subject (e.g., a human) who has been diagnosed with cancer, e.g.

CLL, wherein the method comprises administering a therapy to treat the comorbidity in combination with of the pharmaceutical compositions (including, for example, the tablets and unit dosage forms) described herein to the subject. In some embodiments, the comorbidity is selected from the group consisting of one or more other cancers (e.g. breast, head and neck, lung, melanoma, non-Hodgkin's T-cell lymphoma, prostate, colon, small intestine, gynecologic and urinary tract), hypertension, hyperlipidemia, coronary artery disease, peripheral vascular diseases, cardiomyopathy, vulvular heart disease, atrial fibrillation, cerebrovascular disease (e.g. transient ischemic attack, stroke), chronic obstructive pulmonary disease, joint disease, peptic ulcer, inflammatory bowel disease, psychiatric illness, thyroid disease, benign prostate hyperplasia, diabetes mellitus, and osteoarthritis.

Combination Therapies

In some embodiments, a method of treating cancer, an allergic disorder and/or an autoimmune and/or inflammatory disease, and/or an acute inflammatory reaction comprises administering to a subject (e.g., a human) in need thereof the pharmaceutical compositions (including, for example, the tablets and unit dosage forms) described herein, together with one or more additional therapies (e.g., one or more additional therapeutic agents), which can be useful for treating a cancer, an allergic disorder and/or an autoimmune and/or inflammatory disease, and/or an acute inflammatory reaction.

In some embodiments, a method of treating cancer, an allergic disorder and/or an autoimmune and/or inflammatory disease, and/or an acute inflammatory reaction comprises administering to a subject in need thereof the pharmaceutical compositions (including, for example, the tablets and unit dosage forms) described herein, together with a second active agent, which can be useful for treating a cancer, an allergic disorder and/or an autoimmune and/or inflammatory disease, and/or an acute inflammatory reaction. For example the second agent may be an anti-inflammatory agent. Treatment with the second active agent may be prior to, concomitant with, or following treatment with the pharmaceutical compositions (including, for example, the tablets and unit dosage forms) described herein. In some embodiments, the pharmaceutical compositions (including, for example, the tablets and unit dosage forms) described herein, is combined with another active agent in a single dosage form.

Provided herein are also methods of treatment in which the pharmaceutical compositions (including, for example, the tablets and unit dosage forms) described herein are administered to a subject (e.g., a human) who has been diagnosed with or is suspected of having a cancer is given to the subject in combination with one or more additional therapies, including one or more of the anti-cancer therapies described above. Thus, in some embodiments, the method for treating cancer in a subject (e.g., a human) in need thereof, comprises administering to the subject the pharmaceutical compositions (including, for example, the tablets and unit dosage forms) described herein, together with one or more additional therapies, which can be useful for treating the cancer. The one or more additional therapies may involve the administration of one or more therapeutic agents.

In one aspect, provided is a method of treating cancer in a human in need thereof, comprising administering the pharmaceutical compositions (including, for example, the tablets and unit dosage forms) described herein, and an additional therapeutic agent to the human. In any of the foregoing embodiments, the treatment of cancer may include, for example, leukemia, lymphoma and solid-cell tumors.

The additional therapeutic agent may be one or more agents. In some embodiments, the one or more additional therapeutic agent may be a phosphatidylinositol 3-kinase (PI3K) inhibitor, including for example, Compounds A, B, C and D, whose structures are provided below.

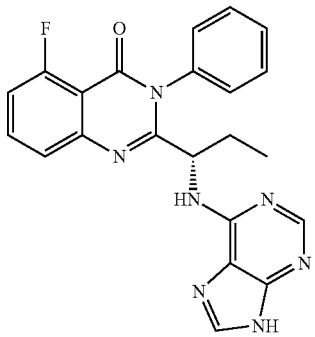

Compound A

Compound B

Compound C

Compound D

In other embodiments, the one or more additional therapeutic agent may be an inhibitors of lysyl oxidase-like 2 (LOXL2) or a substance that binds to LOXL2, including for example, a humanized monoclonal antibody (mAb) with an immunoglobulin IgG4 isotype directed against human LOXL2. In yet other embodiments, the one or more additional therapeutic agent may be an inhibitor of apoptosis signal-regulating kinase (ASK-1) or a substance that binds to ASK-1. In yet other embodiments, the one or more additional therapeutic agent may be an inhibitor of a Janus kinase, such as JAK1 or JAK2, or a substance that binds to a Janus kinase, such as JAK1 or JAK2. In one embodiment, the one or more additional therapeutic agent is momelotinib. In other embodiments, the one or more additional therapeutic agent may be a Bruton's tyrosine kinase (BTK) inhibitor. In yet other embodiments, the one or more additional therapeutic agent may be a B-cell lymphoma (BCL) inhibitor. In some variations, the BCL inhibitor is a BCL-2 inhibitor. In one variation, the BCL inhibitor is ABT-199.

In yet other embodiments, the one or more additional therapeutic agent may be fludarabine, rituximab, obinutuzumab, alkylating agents, alemtuzumab and other chemotherapy treatments such as CHOP (cyclophosphamide, doxorubicin, vincristine, prednisone); R-CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar®) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D.T. PACE (dexamethasone, thalidomide, cisplatin, Adriamycin®, cyclophosphamide, etoposide).

In other embodiments, the one or more additional therapeutic agent may be a vinca-alkaloid. In one variation, the vinca-alkaloid is selected from the group consisting of vincristine, vinblastine, vindesine, vinorelbine, desoxyvincaminol, vincaminol, vinburnine, vincamajine, and vineridine, and pharmaceutically acceptable salts thereof. In certain variations, at least one vinca-alkaloid is selected from the group consisting of vincristine, vinblastine, vindesine, vinorelbine, desoxyvincaminol, vincaminol, vinburnine, vincamajine, and vineridine and pharmaceutically acceptable salts thereof. In some variations, the vinca-alkaloid is selected from the group consisting of vincristine, vinblastine, vindesine, and vinorelbine, and pharmaceutically acceptable salts thereof. In other variations, the vinca-alkaloid is selected from the group consisting of vincristine and vinblastine, and pharmaceutically acceptable salts thereof. In one variation, the vinca-alkaloid is vincristine and pharmaceutically acceptable salts thereof. In another variation, the vinca-alkaloid is vinblastine and pharmaceutically acceptable salts thereof. Thus, in one aspect, provided is a method for treating cancer in a human in need thereof, comprising administering to the human the pharmaceutical compositions (including, for example, the tablets and unit dosage forms) described herein; and a vinca-alkaloid, or a pharmaceutically acceptable salt thereof.

In other embodiments, the one or more additional therapies may be any monotherapy or combination therapy suitable for treating leukemia, including, for example, chronic lymphocytic leukemia (CLL), acute lymphocytic leukemia (ALL), and/or acute myeloid leukemia (AML).

In other embodiments, the one or more additional therapeutic agent may be an anti-inflammatory agent. Treatment with the one or more additional therapeutic agent may be prior to, concomitant with, or following treatment with the pharmaceutical composition described herein. In some embodiments, the pharmaceutical composition described herein is combined with another therapeutic agent in a single dosage form. Suitable antitumor therapeutics that may be used in combination with at least one chemical entity described herein include, but are not limited to, chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

The pharmaceutical composition described herein can be useful as chemosensitizing agents, and, thus, can be useful in combination with other chemotherapeutic drugs, in particular, drugs that induce apoptosis.

A method for increasing sensitivity of cancer cells to chemotherapy, comprising administering to a subject (e.g., human) undergoing chemotherapy a chemotherapeutic agent together with the pharmaceutical composition described herein in an amount sufficient to increase the sensitivity of cancer cells to the chemotherapeutic agent is also provided herein. Examples of other chemotherapeutic drugs that can be used in combination with chemical entities described herein include topoisomerase I inhibitors (camptothesin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

In some embodiments, the pharmaceutical composition described herein are used in combination with Rituxan® (Rituximab) or other agents that work by selectively depleting CD20+ B-cells.

Included herein are methods of treatment in which the pharmaceutical composition described herein is administered in combination with an anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate. Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an IC50 that is at least 50-fold lower than the IC50 for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates. The anti-inflammatory agent may also be a corticosteroid. For example, the corticosteroid may be chosen from cortisone, dexamethasone, methylprednisolone, prednisolone, prednisolone sodium phosphate, and prednisone. In some embodiments, the anti-inflammatory therapeutic agent is a gold compound such as gold sodium thiomalate or auranofin. In some embodiments, the anti-inflammatory agent is a metabolic inhibitor such as a dihydrofolate reductase inhibitor, such as methotrexate or a dihydroorotate dehydrogenase inhibitor, such as leflunomide.

In some embodiments, combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody are used.

In some embodiments, combinations in which at least one therapeutic agent is an immunosuppressant compound such as methotrexate, leflunomide, cyclosporine, tacrolimus, azathioprine, or mycophenolate mofetil are used.

It should be understood that any combinations of the additional therapeutic agents described above may be used, as if each and every combination was individually listed. For example, in certain embodiments, the additional therapeutic agents include a PI3K inhibitor and a LOXL2 inhibitor.

Kits

Kits comprising the pharmaceutical compositions (including, for example, the tablets and unit dosage forms) described herein are also provided.

In one aspect, provided is a kit comprising a pharmaceutical composition, comprising: a bis-mesylate salt of a compound of Formula I, or a hydrate thereof; and a pharmaceutical carrier. In certain aspects, provided is a kit comprising a pharmaceutical composition, comprising: a hydrate, bis-mesylate salt of a compound of Formula I, and a pharmaceutical carrier. In one aspect, provided is a kit comprising a pharmaceutical composition, comprising: a monohydrate, bis-mesylate salt of a compound of Formula I, and a pharmaceutical carrier. In certain aspects, provided is a kit comprising a pharmaceutical composition, comprising: a mesylate salt of Formula IA or IB, or a hydrate thereof; and a pharmaceutical carrier. In other aspects, provided is a kit comprising a pharmaceutical composition, comprising: a hydrate, mesylate salt of Formula IA or IB; and a pharmaceutical carrier. In one aspect, provided is a kit comprising a pharmaceutical composition, comprising: polymorph Form 3; and a pharmaceutical carrier. In another aspect, provided is a kit comprising a pharmaceutical composition, comprising: polymorph Form 7; and a pharmaceutical carrier.

In one variation, the mesylate salt is bis-mesylate salt of Formula IA. In a particular variation, the mesylate salt is Form 3 of bis-mesylate salt of Formula IA, Form 7 of bis-mesylate salt of Formula IA, or a mixture thereof. As described herein, Form 3 and Form 7 are polymorphic forms of a bis-mesylate salt of a compound of Formula I. For example, Form 3 is a polymorph of a monohydrate, bis-mesylate salt of a compound of Formula I.

In one aspect, the kit comprises instructions for use in the treatment of cancer or inflammatory conditions. In a particular variation, the instructions are directed to use of the pharmaceutical composition for the treatment of cancer, including for example, leukemia or lymphoma. In certain embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), indolent non-Hodgkin's lymphoma (iNHL), refractory iNHL, non-Hodgkin's lymphoma (NHL), mantle cell lymphoma (MCL), follicular lymphoma (FL), Waldestrom's macroglobulinemia (WM), T-cell lymphoma, B-cell lymphoma, diffuse large B-cell lymphoma (DLBCL), lymphoplasmacytic lymphoma (LPL), and marginal zone lymphoma (MZL). In certain embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), indolent non-Hodgkin's lymphoma (iNHL), refractory iNHL, non-Hodgkin's lymphoma (NHL), mantle cell lymphoma (MCL), follicular lymphoma (FL), Waldestrom's macroglobulinemia (WM), T-cell lymphoma, B-cell lymphoma, and diffuse large B-cell lymphoma (DLBCL). In one embodiment, the cancer is T-cell acute lymphoblastic leukemia (T-ALL), or B-cell acute lymphoblastic leukemia (B-ALL). In some embodiments, the cancer is MCL, DLBCL, iNHL, FL, MZL, LPL, SLL, or WM. In other embodiments, the cancer is CLL, MCL, DLBCL, iNHL (including, for example, non-FL iNHL), or FL.

The non-Hodgkin lymphoma encompasses the indolent B-cell diseases that include, for example, follicular lymphoma, lymphoplasmacytic lymphoma, Waldenstrom macroglobulinemia, and marginal zone lymphoma, as well as the aggressive lymphomas that include, for example, Burkitt lymphoma, diffuse large B-cell lymphoma (DLBCL) and mantle cell lymphoma (MCL). In one embodiment, the cancer is indolent non-Hodgkin's lymphoma (iNHL). In another embodiment, the cancer is non-FL iNHL.

In a particular variation, the instructions are directed to use of the pharmaceutical composition for the treatment of an autoimmune disease. Certain embodiments of an autoimmune disease include asthma, rheumatoid arthritis, multiple sclerosis, and lupus.

Any pharmaceutical composition provided in the present disclosure may be used in the kits, the same as if each and every composition were specifically and individually listed for use a kit. For example, in one embodiment a kit may comprise: a) about 34% w/w of a mesylate salt (including, for example, a mono-mesylate or bis-mesylate salt) of a compound of Formula I; b) about 15% w/w HPMC; c) about 22% w/w mannitol; d) about 10% w/w crospovidone; and e) about 1% w/w to about 3% w/w poloxamer. In another embodiment, a kit may comprise: a) about 34% w/w of a bis-mesylate salt of a compound of Formula I, or a hydrate thereof; b) about 15% w/w HPMC; c) about 22% w/w mannitol; d) about 10% w/w crospovidone; and e) about 1% w/w to about 3% w/w poloxamer. In yet another embodiment, a kit may comprise: a) about 34% w/w of a monohydrate, bis-mesylate salt of a compound of Formula I; b) about 15% w/w HPMC; c) about 22% w/w mannitol; d) about 10% w/w crospovidone; and e) about 1% w/w to about 3% w/w poloxamer. In yet another embodiment, a kit may comprise: a) about 34% w/w of polymorph Form 3, polymorph Form 7, or a combination thereof; b) about 15% w/w HPMC; c) about 22% w/w mannitol; d) about 10% w/w crospovidone; and e) about 1% w/w to about 3% w/w poloxamer.

Articles of Manufacture

Articles of manufacture comprising a container in which a pharmaceutical composition comprising a mesylate salt (including, for example, a mono-mesylate salt, a bis-mesylate salt, or a combination thereof) of a compound of Formula I and at least one pharmaceutically acceptable polymer are contained are provided. The article of manufacture may be a bottle, vial, ampoule, single-use disposable applicator, or the like, containing the pharmaceutical composition provided in the present disclosure. The container may be formed from a variety of materials, such as glass or plastic and in one aspect also contains a label on, or associated with, the container which indicates directions for use in the treatment of cancer or inflammatory conditions.

In one aspect, provided is an article of manufacture comprising a bis-mesylate salt of a compound of Formula I, or a hydrate thereof. In certain aspects, provided is an article of manufacture comprising a hydrate, bis-mesylate salt of a compound of Formula I. In one aspect, provided is an article of manufacture comprising a monohydrate, bis-mesylate salt of a compound of Formula I. In certain aspects, provided is an article of manufacture comprising a mesylate salt of Formula IA or IB, or a hydrate thereof. In other aspects, provided is an article of manufacture comprising a hydrate, mesylate salt of Formula IA or IB. In one aspect, provided is an article of manufacture comprising polymorph Form 3. In one aspect, provided is an article of manufacture comprising polymorph Form 7. In any of the foregoing embodiments, the article of manufacture may further comprise a label containing instructions for use of the mesylate salt.

Unit dosage forms of the pharmaceutical composition comprising a mesylate salt (including, for example, a mono-mesylate or bis-mesylate salt) of a compound of Formula I and at least one pharmaceutically acceptable polymer are also provided. In one aspect, provided is a unit dosage comprising a bis-mesylate salt of a compound of Formula I, or a hydrate thereof. In certain aspects, provided is a unit dosage comprising a hydrate, bis-mesylate salt of a compound of Formula I. In one aspect, provided is a unit dosage comprising a mono-hydrate, bis-mesylate salt of a compound of Formula I. In certain aspects, provided is a unit dosage comprising a mesylate salt of Formula IA or IB, or a hydrate thereof. In other aspects, provided is a unit dosage comprising a hydrate, mesylate salt of Formula IA or IB. In one aspect, provided is a unit dosage comprising polymorph Form 3. In one aspect, provided is a unit dosage comprising polymorph Form 7. In any of the foregoing embodiments, the unit dosage is a tablet.

Any pharmaceutical composition provided in the present disclosure may be used in the articles of manufacture, the same as if each and every composition were specifically and individually listed for use an article of manufacture. For example, in one embodiment, an article of manufacture may comprise: a) about 34% w/w of a mesylate salt (including, for example, a mono-mesylate or bis-mesylate salt) of a compound of Formula I; b) about 15% w/w HPMC; c) about 22% w/w mannitol; d) about 10% w/w crospovidone; and e) about 1% w/w to about 3% w/w poloxamer. In another embodiment, an article of manufacture may comprise: a) about 34% w/w of a bis-mesylate salt of a compound of Formula I, or a hydrate thereof; b) about 15% w/w HPMC; c) about 22% w/w mannitol; d) about 10% w/w crospovidone; and e) about 1% w/w to about 3% w/w poloxamer. In yet another embodiment, an article of manufacture may comprise: a) about 34% w/w of a monohydrate, bis-mesylate salt of a compound of Formula I; b) about 15% w/w HPMC; c) about 22% w/w mannitol; d) about 10% w/w crospovidone; and e) about 1% w/w to about 3% w/w poloxamer. In yet another embodiment, an article of manufacture may comprise: a) about 34% w/w of polymorph Form 3, polymorph Form 7, or a combination thereof; b) about 15% w/w HPMC; c) about 22% w/w mannitol; d) about 10% w/w crospovidone; and e) about 1% w/w to about 3% w/w poloxamer.

Enumerated Embodiments

The following enumerated embodiments are representative of some aspects of the invention.

1. A pharmaceutical composition comprising a bis-mesylate salt of Formula IA

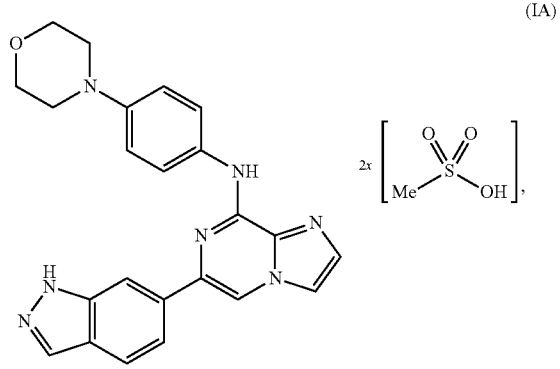

and at least one pharmaceutically acceptable polymer.

2. The pharmaceutical composition of embodiment 1, wherein the bis-mesylate salt of Formula IA is formulated as a tablet.
3. The pharmaceutical composition of embodiment 2, wherein the bis-mesylate salt of Formula IA is formulated as a solid dispersion tablet.
4. The pharmaceutical composition of embodiment 3, wherein the solid dispersion tablet is a spray-dry solid dispersion tablet.
5. The pharmaceutical composition of embodiment 3 or 4, wherein the at least one pharmaceutically acceptable polymer forms a polymer matrix.
6. The pharmaceutical composition of embodiment 5, wherein the bis-mesylate salt of Formula IA is dispersed within the polymer matrix.
7. The pharmaceutical composition of embodiment 2, wherein the tablet is a dry granulation tablet.
8. The pharmaceutical composition of embodiment 7, wherein the bis-mesylate salt of Formula IA is a Form 3 polymorph having an X-ray diffraction pattern comprising 2θ-reflections (±0.2°) at 13.8, 16.9, 22.9, and 26.1.
9. The pharmaceutical composition of any one of embodiments 1 to 8, wherein one of the at least one pharmaceutically acceptable polymer is a precipitation inhibitor.
10. The pharmaceutical composition of any one of embodiments 1 to 8, wherein one of the at least one pharmaceutically acceptable polymer is hydroxypropylmethylcellulose.
11. The pharmaceutical composition of any one of embodiments 1 to 10, further comprising at least one diluent.
12. The pharmaceutical composition of embodiment 11, wherein one of the at least one diluent is mannitol.
13. The pharmaceutical composition of any one of embodiments 1 to 12, further comprising any one or more of crospovidone, poloxamer, colloidal silicon dioxide, magnesium stearate, and microcrystalline cellulose.
14. A unit dosage form comprising a pharmaceutical composition of any one of embodiments 1 to 13.
15. The unit dosage form of embodiment 14, wherein the unit dosage form is a tablet.
16. An article of manufacture comprising a pharmaceutical composition of any one of embodiments 1 to 13, or a unit dosage form of embodiment 14 or 15.
17. A method of treating a condition in a subject in need thereof, comprising administering to the subject a therapeutically effective amount of a pharmaceutical composition of any one of embodiments 1 to 13 or therapeutically effective amount of a unit dosage form of embodiment 14 or 15, wherein the condition is selected from the group consisting of cancer and autoimmune disease.
18. The method of embodiment 17, wherein the subject is human.
19. The method of embodiment 17 or 18, wherein the condition is selected from the group consisting of acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), indolent non-Hodgkin's lymphoma (iNHL), refractory iNHL, non-Hodgkin's lymphoma (NHL), mantle cell lymphoma (MCL), follicular lymphoma, Waldestrom's macroglobulinemia (WM), T-cell lymphoma, B-cell lymphoma, and diffuse large B-cell lymphoma (DLBCL).
20. The method of embodiment 17 or 18, wherein the condition is selected from the group consisting of asthma, rheumatoid arthritis, multiple sclerosis, and lupus.

21. A composition comprising:
(i) a bis-mesylate salt of a compound of Formula I:

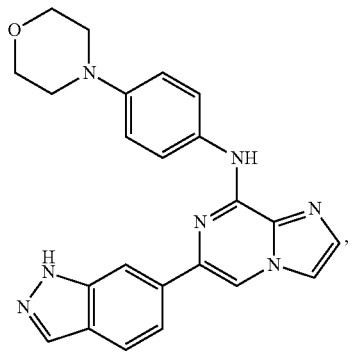

or a hydrate thereof, and
(ii) at least one pharmaceutically acceptable carrier.

22. The composition of embodiment 21, wherein the bis-mesylate salt is a monohydrate, bis-mesylate salt of the compound of Formula I.

23. The composition of embodiment 21 or 22, wherein the bis-mesylate salt is a polymorph having an X-ray diffraction pattern comprising 2θ-reflections, plus or minus 0.2 degrees 2θ, at 7.7, 12.9, 17.7, and 18.1.

24. The composition of embodiment 23, wherein the bis-mesylate salt is a polymorph having an X-ray diffraction pattern further comprising 2θ-reflections, plus or minus 0.2 degrees 2θ, at 13.8, 16.9, 22.9 and 26.1.

25. The composition of embodiment 21, wherein the bis-mesylate salt is a polymorph characterized by a unit cell as determined by crystal X-ray crystallography of the following dimensions: a=8.7831(6) Å; b=11.8484(8) Å; c=14.2485(10) Å; α=98.108(6)°; β=100.955(6)°; and γ=98.861(6)°.

26. The composition of any one of embodiments 21 to 25, further comprising methanesulfonic acid.

27. A composition comprising:
(i) a compound of Formula I:

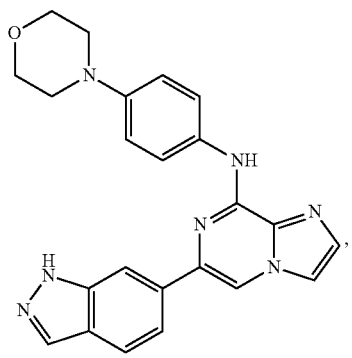

or a cation thereof;
(ii) methanesulfonic acid, or an anion thereof; and
(iii) at least one pharmaceutically acceptable carrier.

28. The composition of embodiment 27, wherein the methanesulfonic acid, or an anion thereof, and the compound of Formula I, or a cation thereof, are present in the composition in a molar ratio of the methanesulfonic acid, or an anion thereof, to the compound of Formula I, or a cation thereof, of between 2:1 and 3:1, between 2:1 and 2.7:1, or between 2.1:1 and 2.5:1, or between 2.2:1 and 2.4:1, or about 2.3:1, or about 2.4:1.

29. The composition of any one of embodiments 21 to 28, wherein the at least one pharmaceutically acceptable carrier is at least one pharmaceutically acceptable polymer.

30. The composition of embodiment 29, wherein the at least one pharmaceutically acceptable polymer is a precipitation inhibitor.

31. The composition of embodiment 29, wherein the at least one pharmaceutically acceptable polymer is non-ionic.

32. The composition of embodiment 29, wherein the at least one pharmaceutically acceptable polymer is selected from the group consisting of hydroxypropylmethylcellulose, copovidone, povidone, methyl cellulose, hydroxyethylcellulose, hydroxypropylcellulose, ethylcellulose, pyroxylin, polyethylene oxide, polyvinyl alcohol, polyethylene glycol, and polyvinyl caprolactam-polyvinyl acetate-polyethylene glycol.

33. The composition of embodiment 32, wherein the at least one pharmaceutically acceptable polymer is hydroxypropylmethylcellulose.

34. The composition of any one of embodiments 29 to 33, wherein the composition comprises a polymer matrix obtainable from the at least one pharmaceutically acceptable polymer.

35. The composition of embodiment 34, wherein the compound of Formula I, or a cation thereof, and the methanesulfonic acid, or an anion thereof, are dispersed within the polymer matrix.

36. The composition of any one of embodiments 21 to 35, further comprising water.

37. The composition of any one of embodiments 21, 22 and 26 to 36, wherein the composition is a feed solution for spray drying.

38. The composition of any one of embodiments 21, 22 and 26 to 35, wherein the composition is a spray-dried powder.

39. The composition of embodiment 38, wherein the powder is non-crystalline.

40. The composition of embodiment 38 or 39, wherein the particle is characterized by an X-ray diffraction pattern comprising 2θ-reflections, plus or minus 0.2 degrees 2θ, at 6.3 and between 26.1 to 26.6.

41. The composition of any one of embodiments 21 to 25 and 38 to 40, wherein the composition is a tablet.

42. The composition of embodiment 41, further comprising at least one diluent, binder, disintegrant, surfactant, glidant, or lubricant, or any combinations thereof.

43. The composition of embodiment 42, wherein one of the at least one diluent is mannitol.

44. The composition of any one of embodiments 41 to 43, further comprising any one or more of crospovidone, poloxamer, colloidal silicon dioxide, magnesium stearate, and microcrystalline cellulose.

45. A method of manufacturing a tablet, comprising:
   a) forming spray-dried powder from a feed solution, wherein the feed solution comprises:
      (i) a compound of Formula I:

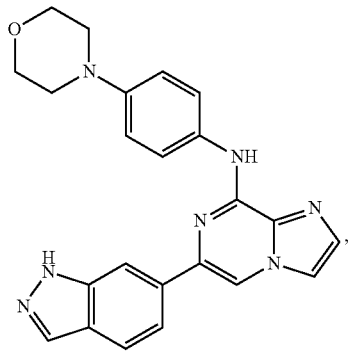

(I)

or a cation thereof;
      (ii) methanesulfonic acid, or an anion thereof;
      (iii) at least one pharmaceutically acceptable carrier; and
      (iv) water; and
   b) dry granulating the spray-dried powder and at least one additional pharmaceutically acceptable carrier to form a granulation; and
   c) compressing the granulation to form the tablet.

46. The method of embodiment 45, wherein the methanesulfonic acid or an anion thereof, and the compound of Formula I or a cation thereof, are present in the feed solution in a molar ratio of the methanesulfonic acid or an anion thereof, to the compound of Formula I or a cation thereof, of between 2:1 and 3:1, between 2:1 and 2.7:1, or between 2.1:1 and 2.5:1, or between 2.2:1 and 2.4:1, or about 2.3:1, or about 2.4:1.

47. A method of manufacturing a tablet, comprising:
   a) dry granulating:
      (i) a bis-mesylate salt of a compound of Formula I:

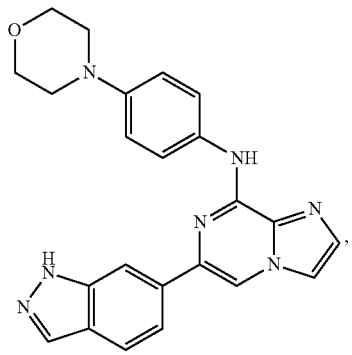

(I)

or a hydrate thereof, and
      (ii) at least one pharmaceutically acceptable carrier to form a granulation; and
   b) compressing the granulation to form the tablet.

48. A tablet produced according to the method of any one of embodiments 44 to 47.

49. A unit dosage form comprising the composition of any one of embodiments 21 to 35 and 38 to 44, or the tablet of embodiment 48.

50. An article of manufacture comprising the composition of any one of embodiments 21 to 35 and 38 to 44, or the tablet of embodiment 48, or a unit dosage form of embodiment 49.

51. A method of treating a condition in a human in need thereof, comprising administering to the human a therapeutically effective amount of a composition of embodiments 21 to 35 and 38 to 44, or therapeutically effective amount of a tablet of embodiment 48, or therapeutically effective amount of a unit dosage form of embodiment 49, wherein the condition is selected from the group consisting of cancer and autoimmune disease.

52. The method of embodiment 51, wherein the condition is selected from the group consisting of acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), mantle cell lymphoma (MCL), follicular lymphoma, Waldestrom's macroglobulinemia (WM), T-cell lymphoma, B-cell lymphoma, and diffuse large B-cell lymphoma (DLBCL).

53. The method of embodiment 52, wherein the condition is non-Hodgkin's lymphoma (NHL).

54. The method of embodiment 53, wherein the NHL is indolent non-Hodgkin's lymphoma (iNHL).

55. The method of embodiment 54, wherein the iNHL is refractory iNHL or non-FL iNHL.

56. The method of embodiment 51, wherein the condition is selected from the group consisting of asthma, rheumatoid arthritis, multiple sclerosis, and lupus.

57. A method of preparing feed solution for spray drying, comprising combining:
   (i) either:
      (A) a compound of Formula I:

(I)

and methanesulfonic acid; or
  (B) a mesylate salt of a compound of Formula I:

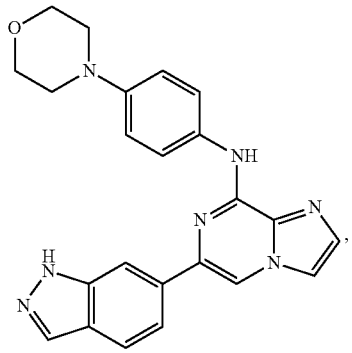

or a hydrate thereof;
  (ii) at least one pharmaceutically acceptable carrier; and
  (iii) water
to form a feed solution.
58. The method of embodiment 57, wherein the mesylate salt, or a hydrate thereof, is combined with the at least one pharmaceutically acceptable carrier and water to form the feed solution, and wherein the method further comprises combining methanesulfonic acid with the feed solution.
59. The method of embodiment 57 or 58, wherein the mesylate salt of the compound of Formula I, or a hydrate thereof, is a bis-mesylate salt of the compound of Formula I, or a hydrate thereof.
60. The method of embodiment 59, wherein the bis-mesylate salt of the compound of Formula I, or a hydrate thereof, is a hydrate, bis-mesylate salt of the compound of Formula I.
61. The method of embodiment 60, wherein the hydrate, bis-mesylate salt of the compound of Formula I is a monohydrate, bis-mesylate salt of a compound of Formula I.
62. A feed solution for spray drying prepared according to the method of any one of embodiments 58 to 61.
63. A feed solution, comprising:
  (i) a bis-mesylate salt of a compound of Formula I:

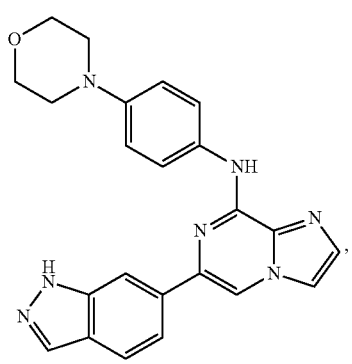

and
  (ii) a carrier.
64. The feed solution of embodiment 63, further comprising methanesulfonic acid.
65. A feed solution, comprising:
  (i) a compound of Formula I:

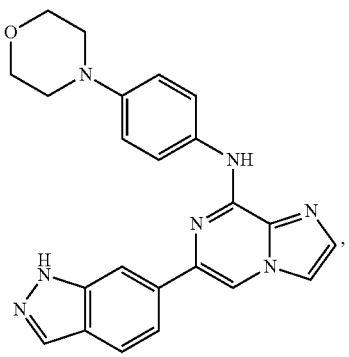

or a cation thereof;
  (ii) methanesulfonic acid, or an anion thereof; and
  (iii) a carrier.
66. The feed solution of embodiment 65, wherein the methanesulfonic acid, or an anion thereof, and the compound of Formula I, or a cation thereof, are present in the composition in a molar ratio of the methanesulfonic acid, or an anion thereof, to the compound of Formula I, or a cation thereof, of between 2:1 and 3:1, between 2:1 and 2.7:1, or between 2.1:1 and 2.5:1, or between 2.2:1 and 2.4:1, or about 2.3:1, or about 2.4:1.
67. The feed solution of any one of embodiments 63 to 66, wherein the carrier is a pharmaceutically acceptable carrier.
68. The feed solution of embodiment 67, wherein the pharmaceutically acceptable carrier is a pharmaceutically acceptable polymer.
69. The feed solution of embodiment 68, wherein the pharmaceutically acceptable polymer is a precipitation inhibitor.
70. The feed solution of embodiment 68, wherein the pharmaceutically acceptable polymer is non-ionic.
71. The feed solution of embodiment 68, wherein the pharmaceutically acceptable polymer is selected from the group consisting of hydroxypropylmethylcellulose, copovidone, povidone, methyl cellulose, hydroxyethylcellulose, hydroxypropylcellulose, ethylcellulose, pyroxylin, polyethylene oxide, polyvinyl alcohol, polyethylene glycol, and polyvinyl caprolactam-polyvinyl acetate-polyethylene glycol.
72. The feed solution of embodiment 71, wherein the at least one pharmaceutically acceptable polymer is hydroxypropylmethylcellulose.
73. The feed solution of any one of embodiments 68 to 72, wherein the composition comprises a polymer matrix obtainable from the pharmaceutically acceptable polymer.
74. The feed solution of embodiment 73, wherein the compound of Formula I, or a cation thereof, and the methanesulfonic acid, or an anion thereof, are dispersed within the polymer matrix.
75. The feed solution of any one of embodiments 63 to 74, further comprising water.

76. A spray-dried powder, comprising:
(i) a bis-mesylate salt of a compound of Formula I:

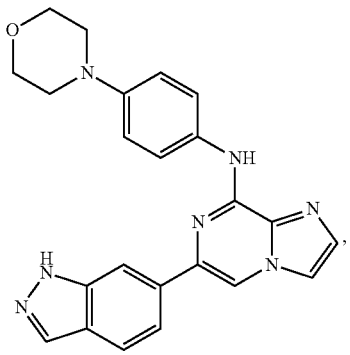

(I)

and
(ii) a carrier.
77. The spray-dried powder of embodiment 76, further comprising methanesulfonic acid.
78. A spray-dried powder, comprising:
(i) a compound of Formula I:

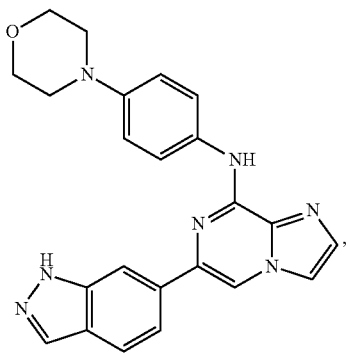

(I)

or a cation thereof;
(ii) methanesulfonic acid, or an anion thereof; and
(iii) a carrier.
79. The spray-dried powder of embodiment 78, wherein the methanesulfonic acid, or an anion thereof, and the compound of Formula I, or a cation thereof, are present in the composition in a molar ratio of the methanesulfonic acid, or an anion thereof, to the compound of Formula I, or a cation thereof, of between 2:1 and 3:1, between 2:1 and 2.7:1, or between 2.1:1 and 2.5:1, or between 2.2:1 and 2.4:1, or about 2.3:1, or about 2.4:1.
80. The spray-dried powder of any one of embodiments 76 to 79, wherein the carrier is a pharmaceutically acceptable carrier.
81. The spray-dried powder of embodiment 80, wherein the pharmaceutically acceptable carrier is a pharmaceutically acceptable polymer.
82. The spray-dried powder of embodiment 80, wherein the pharmaceutically acceptable polymer is a precipitation inhibitor.
83. The spray-dried powder of embodiment 80, wherein the pharmaceutically acceptable polymer is non-ionic.
84. The spray-dried powder of embodiment 80, wherein the pharmaceutically acceptable polymer is selected from the group consisting of hydroxypropylmethylcellulose, copovidone, povidone, methyl cellulose, hydroxyethylcellulose, hydroxypropylcellulose, ethylcellulose, pyroxylin, polyethylene oxide, polyvinyl alcohol, polyethylene glycol, and polyvinyl caprolactam-polyvinyl acetate-polyethylene glycol.
85. The spray-dried powder of embodiment 84, wherein the at least one pharmaceutically acceptable polymer is hydroxypropylmethylcellulose.
86. The spray-dried powder of any one of embodiments 81 to 85, wherein the composition comprises a polymer matrix obtainable from the pharmaceutically acceptable polymer.
87. The spray-dried powder of embodiment 86, wherein the compound of Formula I, or a cation thereof, and the methanesulfonic acid, or an anion thereof, are dispersed within the polymer matrix.
88. The spray-dried powder of any one of embodiments 76 to 87, wherein the spray-dried powder is non-crystalline.
89. The spray-dried powder of any one of embodiments 76 to 88, wherein the particle is characterized by an X-ray diffraction pattern comprising 2θ-reflections, plus or minus 0.2 degrees 2θ, at 6.3 and between 26.1 to 26.6.
90. A tablet comprising a spray-dried powder according to any one of embodiments 76 to 89.
91. A kit comprising a composition of any one of embodiments 1 to 13, 21 to 35, and 38 to 44; a tablet of embodiment 48 or 90; a unit dosage of any one of embodiments 14, 15, and 49; or a spray-dried powder of any one of embodiments 76 to 89.
92. The kit of embodiment 91, further comprising instructions for use in the treatment of a condition, wherein the condition is cancer or an autoimmune disease.
93. The kit of embodiment 92, wherein the condition is selected from the group consisting of acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), mantle cell lymphoma (MCL), follicular lymphoma, Waldestrom's macroglobulinemia (WM), T-cell lymphoma, B-cell lymphoma, and diffuse large B-cell lymphoma (DLBCL).
94. The kit of embodiment 92, wherein the condition is non-Hodgkin's lymphoma (NHL).
95. The kit of embodiment 94, wherein the NHL is indolent non-Hodgkin's lymphoma (iNHL).
96. The kit of embodiment 95, wherein the iNHL is refractory iNHL or non-FL iNHL.
97. The kit of embodiment 92, wherein the condition is selected from the group consisting of asthma, rheumatoid arthritis, multiple sclerosis, and lupus.
98. An article of manufacture, comprising a container, wherein the container comprises a composition of any one of embodiments 1 to 13, 21 to 35, and 38 to 44; a tablet of embodiment 48 or 90; a unit dosage of any one of embodiments 14, 15, and 49; or a spray-dried powder of any one of embodiments 76 to 89.
99. The article of manufacture of embodiment 98, wherein the container is a bottle, a vial, an ampoule, or an applicator.

EXAMPLES

The following examples are included to illustrate embodiments of the disclosure, and are not intended to limit the scope of the disclosure. It should be appreciated by those of skill in the art that the techniques disclosed herein represent techniques that apply in the practice of the disclosure. Those of skill in the art would appreciate that, in light of the present disclosure, changes can be made in the examples herein without departing from the spirit and scope of the disclosure.

A. General Synthesis

The polymorphs described herein (e.g., Form 3 and Form 7) may be characterized by various methods known in the art, such as X-ray powder diffraction pattern (XRPD). With respect to polymorph Form 3, exemplary XRPD patterns are provided in FIGS. 1A and 1B. With respect to polymorph Form 7, representative XRPD patterns are provided in FIGS. 1C and 1D.

In the following Examples, the term "X" refers to weight equivalents, and "V" refers to volume equivalents. "RH" refers to relative humidity.

Example A1

Synthesis of Polymorph Form 3

Methods for generally making various forms of the compound of Formula I may be found in U.S. Pat. Nos. 8,450,321 and 8,455,493. The following is a method for producing polymorph Form 3, which is a polymorph of a monohydrate, bis-mesylate salt of a compound of Formula I (and may also be described as a polymorph of a monohydrate of the compound of Formula IA shown in the reaction scheme below).

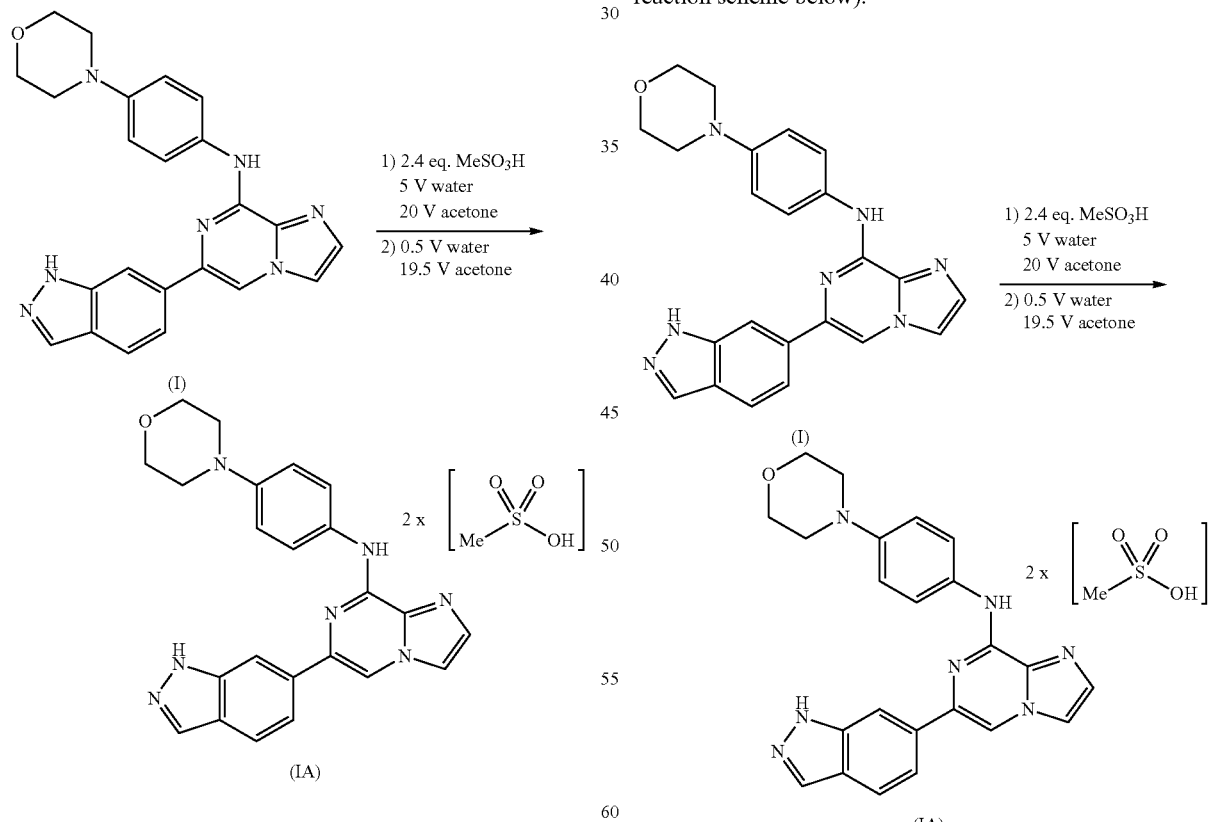

A compound of Formula I (1.0 X) was added to Reactor A. Methanesulfonic acid (0.56 X, 2.40 eq), water (4 X, 4 V) and acetone (3.2 X, 4 V) were added to Reactor B. The contents of Reactor B were added to Reactor A while maintaining the temperature in Reactor A below 35° C. After the solids dissolved, the contents of Reactor A were transferred to Reactor B. Reactor A was rinsed with water (1 X, 1 V) and acetone (0.8 X, 1 V), and transferred to Reactor B. The temperature of Reactor B was adjusted to 19-25° C. Under high agitation, acetone (11.9 X, 15 V) was added to Reactor B. The temperature of Reactor B was adjusted to 0-6° C. and the contents of Reactor B were mixed for 5 h, then filtered, and rinsed with acetone (4.0 X, 5 V) to provide polymorph Form 7. Form 7 was dried under vacuum at 60° C. until constant weight was achieved. Representative patterns of an XRPD of polymorph Form 7 are shown in FIGS. 1C and 1D.

The isolated polymorph Form 7 was added to polymorph Form 3 seeds of a compound of Formula IA (0.01 X, 1 mol %) in Reactor B. Acetone (15.4 X, 19.5 V), and water (0.5 X, 0.5 V) were added to Reactor B and mixed at 19-25° C. until polymorph Form 7 was converted to Form 3. The conversion was monitored by XRPD or DSC. The contents of Reactor B was filtered, rinsed with acetone (2.4 X, 3 V) and dried under vacuum at 60° C. until constant weight was achieved. Representative patterns of an XRPD of polymorph Form 3 are shown in FIGS. 1A and 1B.

Example A2

Alternative Synthesis of Polymorph Form 3

The following is a method for producing polymorph Form 3, a monohydrate, bis-mesylate salt of a compound of Formula I (which may also be described as a polymorph of a monohydrate of the compound of Formula IA shown in the reaction scheme below).

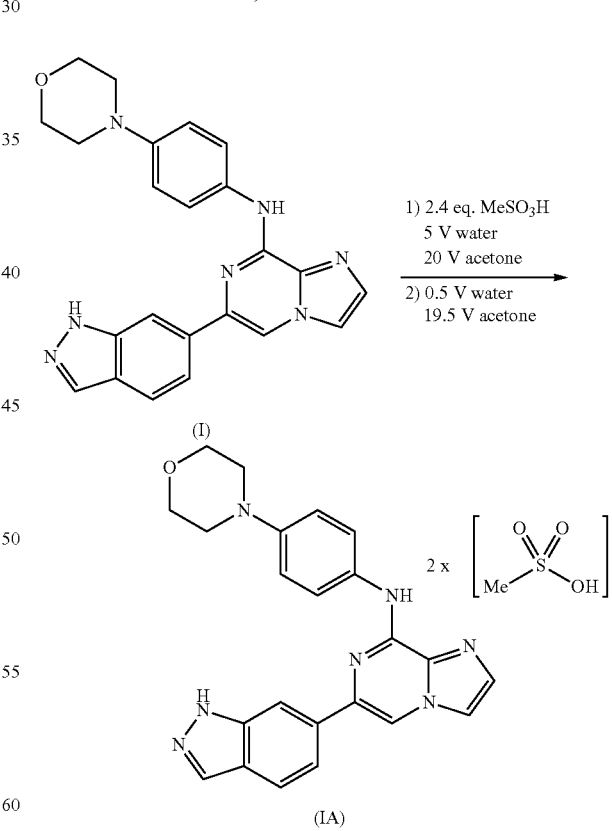

Polymorph Form 7 was obtained as described in Example A1.

The isolated polymorph Form 7 was added to polymorph Form 3 seeds of a compound of Formula IA (0.01 X, 1 mol %) in Reactor B. Acetone (15.0 X, 19.0 V), and water (1.0 X, 1.0

V) were added to Reactor B. The contents of the Reactor B were heated to reflux (about 55° C.) until polymorph Form 7 was converted to Form 3. The conversion was monitored by XRPD or DSC. The contents of Reactor B was a slurry and was cooled to 19-25° C., then filtered, rinsed with acetone (2.4 X, 3 V) and dried under vacuum at 60° C. until constant weight is achieved to provide the polymorph Form 3. Representative patterns of an XRPD of polymorph Form 3 are shown in FIGS. 1A and 1B.

Example A3

One-Pot Synthesis of Polymorph Form 3

The following is a method for producing polymorph Form 3, a monohydrate, bis-mesylate salt of a compound of Formula I (which may also be described as a polymorph of a monohydrate of the compound of Formula IA shown in the reaction scheme below) from a compound of Formula I (as a the free base). The described method uses a single reactor in the conversion of a compound of Formula I to polymorph Form 3, and does not require isolation of a compound intermediate.

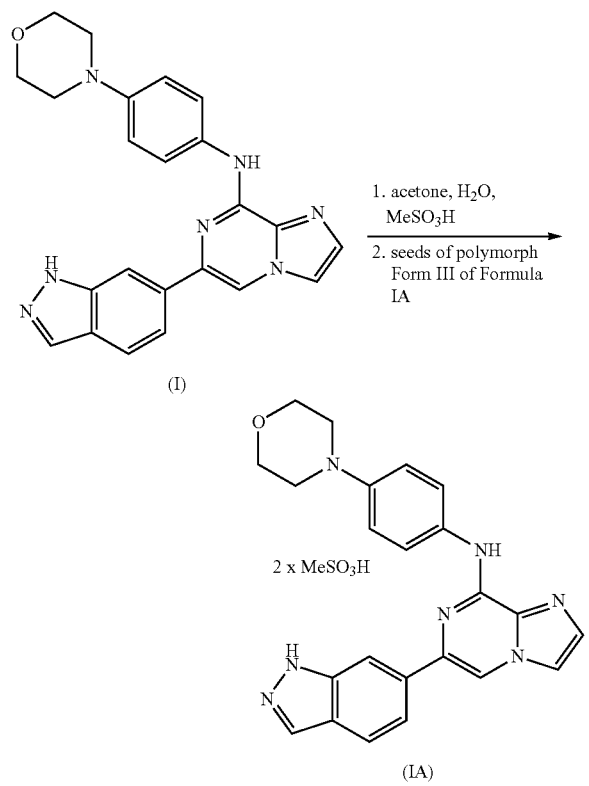

A compound of Formula I (1.0X) was added to acetone (14.2X, 18V) in Reactor A and mixed. Water (0.8X, 0.8V) was added to Reactor A, followed by methanesulfonic acid, (0.48 X, 2.05 eq). Acetone (0.9 X, 1.2 V) was pumped through to rinse the lines forward to Reactor A with acetone. The contents of Reactor A were heated to reflux (about 55° C.) for about 2 hours. Polymorph Form 3 seeds (0.015 X, 1 mol %) were added to Reactor A and the contents mixed at reflux to convert a compound of Formula IA to polymorph Form 3. The conversion was monitored by XRPD. The contents of the reactor were cooled to 19-25° C., filtered, rinsed with acetone (4.0 X, 5 V), and dried under vacuum at 60° C. Representative patterns of an XRPD of polymorph Form 3 are shown in FIGS. 1A and 1B.

Example A4

Alternative Synthetic Route for Polymorph Form 3 Via Mono-MSA Intermediate

This example provides a description of the synthesis of polymorph Form 3 (which is a polymorph of a monohydrate, bis-MSA salt of a compound of Formula I) from a mono-MSA salt of a compound of Formula I.

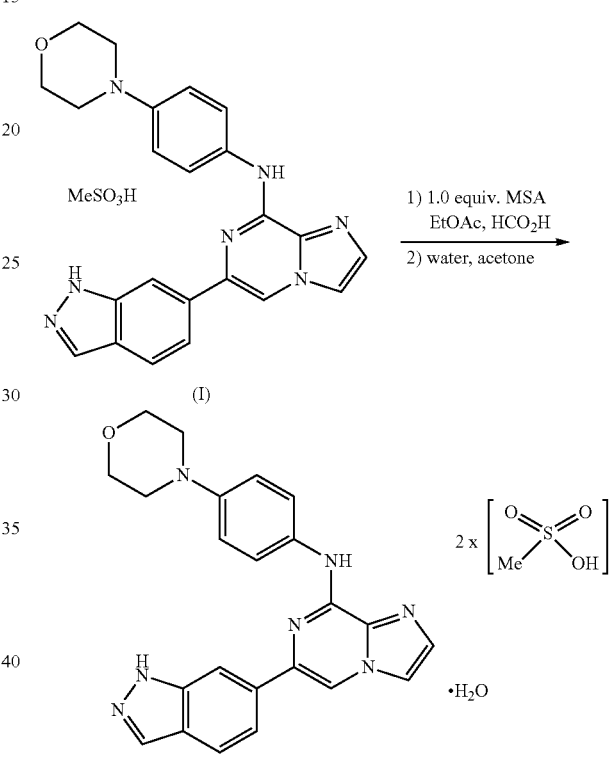

Formic acid (3.7 X) is charged to a reaction vessel and combined with ethyl acetate (9.7 X). The contents are agitated and adjusted to about 19 to 25° C. The mono-MSA compound of Formula I (1.0 X) is charged portion-wise while maintaining the content temperature at about 19 to 25° C. The contents are agitated at about 19 to 25° C. until all solids dissolve.

To the above contents is added a solution of ethyl acetate (0.6 X) and methanesulfonic acid (0.169 X, corrected for MSA content and water present in the mono-MSA compound) prepared in a separate reaction vessel. The resulting mixture is agitated at about 19 to 25° C. for about 24 h. The reaction mixture is sampled and tested for MSA content by ion chromatography. Agitation is continued until the desired range of MSA content is achieved. Upon reaction completion, the contents of the reaction vessel are filtered, rinsed with ethyl acetate (3.6 X) and the wet filter cake is dried under vacuum at about 60° C. The dried solids are transferred back to the reaction vessel.

To the dried solids was added acetone (15.0 X) and the resulting mixture is put under maximum agitation. Water (0.50 X) is added followed by acetone (0.70 X). The mixture is agitated at about 19 to 25° C. until the form conversion to polymorph Form 3 is complete as confirmed by XRPD analysis. The solids are filtered, rinsed with acetone (2.4 X), and the wet cake is dried under vacuum at about 60° C.

Throughout this specification, various patents, patent applications and other types of publications (e.g., journal articles) are referenced. The disclosure of all patents, patent applications, and publications cited herein are hereby incorporated by reference in their entirety for all purposes.

Example A5

Polymorph Form 3 and Polymorph Form 7 XRPD Measurements

This example describes the experimental conditions and data for XRPD measurements of polymorph Form 3 and polymorph Form 7.

Polymorph Form 3

XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640d) was analyzed to verify the observed position of the Si 111 peak is consistent with the NIST-certified position. A specimen of the sample was sandwiched between 3-µm-thick films and analyzed in transmission geometry. A beam-stop, short antiscatter extension, and an antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The data acquisition parameters for each pattern are displayed above the image in the Data section of this report including the divergence slit (DS) before the mirror. Prominent peaks are selected from observed peaks by identifying preferably non-overlapping, low-angle peaks, with strong intensity.

An exemplary XRPD pattern of polymorph Form 3 is shown in FIG. 1A. With reference to FIG. 1A, characteristic XRPD 2θ-reflections (±0.2 degrees) for Form 3 are 13.75, 16.90, 22.88, and 26.06.

Polymorph Form 7

XRPD patterns were collected using a PANalytical X'Pert MPD Pro Powder X-Ray Diffractometer configured with reflectance stage with spinning, data acquisition range: 2-40 degrees 2θ, Copper (Cu) anode; Kα1/Kα2 radiation; tube current 40 mA; tube tension 45 kV; automatic divergence and anti-scatter slits. Samples were prepared for analysis by distributing solid material as a thin layer on a silicon holder. Each holder was mounted on a reflectance/transmittance stage and rotated during data acquisition.

An exemplary XRPD pattern of polymorph Form 7 is shown in FIG. 1C. With reference to FIG. 1C, characteristic XRPD 2θ-reflections (±0.2 degrees) for Form 7 are 4.94, 9.82, and 26.68.

Example A6

Polymorph Form 3 and Polymorph Form 7 XRPD Measurements

This example describes experimental conditions and data for XRPD measurements of polymorph Form 3 and polymorph Form 7.

X-Ray Powder Diffraction (XRPD) patterns were collected on a Bruker AXS C2 GADDS diffractometer using Cu K α radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. A weekly performance check is carried out using a certified standard NIST 1976 Corundum (flat plate).

The beam divergence, i.e. the effective size of the X-ray beam on the sample, was approximately 4 mm. A θ-θ continuous scan mode was employed with a sample—detector distance of 20 cm which gives an effective 2θ range of 3.2°-29.7°. Typically the sample would be exposed to the X-ray beam for 120 seconds. The software used for data collection was GADDS for XP/2000 4.1.43 and the data were analysed and presented using Diffrac Plus EVA v15.0.0.0.

Ambient conditions: Samples run under ambient conditions were prepared as flat plate specimens using powder as received without grinding. Approximately 1-2 mg of the sample was lightly pressed on a glass slide to obtain a flat surface.

Non-ambient conditions: Samples run under non-ambient conditions were mounted on a silicon wafer with heat-conducting compound. The sample was then heated to the appropriate temperature at 20° C./min and subsequently held isothermally for 1 minute before data collection was initiated.

Example A7

Polymorph Form 3 and Polymorph Form 7 XRPD Measurements

This example describes experimental conditions and data for XRPD measurements of polymorph Form 3 and polymorph Form 7.

X-Ray Powder Diffraction (XRPD) patterns were collected on a Bruker D8 diffractometer using Cu K α radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.6.1 and the data were analysed and presented using Diffrac Plus EVA v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection are:
Angular range: 2 to 42° 2θ
Step size: 0.05° 2θ
Collection time: 0.5 s/step Samples run under non-ambient conditions: Approximately 40 mg of the sample was placed in a Ni-coated sample holder under ambient conditions. The sample was loaded at 25° C. The sample was then heated to the appropriate temperature. The details of the data collection are:
Angular range: 3 to 30°2θ
Step size: 0.05° 2θ
Collection time: 0.5 s/step Example A8

Single Crystal X-Ray Structure of Polymorph Form 3

This example describes the single crystal X-ray structure of polymorph Form 3 of a monohydrate, bis-mesylate salt of a compound of Formula I.

Figure 9:
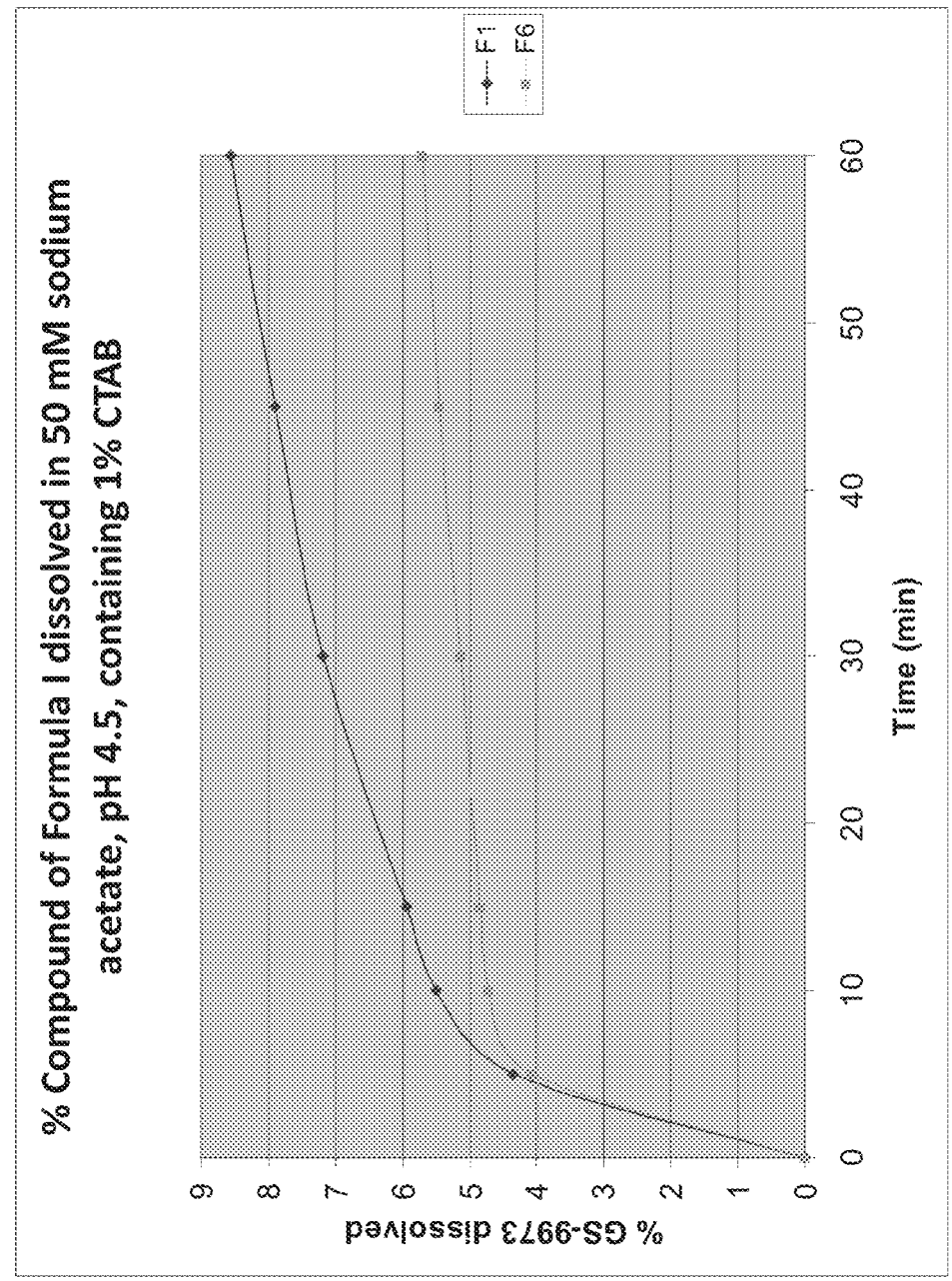
FIG. 9 is a graph comparing dissolution profiles of solid dispersion Formulations F1 and F6 in pH 4.5, 50 mM acetate buffer containing 1% CTAB.

The single crystal X-ray structure of polymorph Form 3 was determined at RT in the triclinic system, space group P-1. There was one cation of the compound of Formula I, two mesylate anions and one water molecule in the asymmetric unit and the final R1 [I>2σ(I)]=4.53%. An XRPD pattern was calculated from the crystal structure to serve as a reference for this form (FIG. 9).

Structural Features

A crystal of sufficient size and quality for analysis by single crystal X-ray diffraction was obtained by maturation between 50° C. and RT on an eight hour cycle in isopropyl acetate. The crystal was of block morphology with approximate dimensions 0.50×0.22×0.15 mm.

The structure of polymorph Form 3 was been determined as depicted in FIGS. 14A-14D. Table A1 below summarizes the sample and crystal data for polymorph Form 3.

TABLE A1

| | |
|---|---|
| Crystallization method | Maturation between RT and 50° C. |
| Empirical formula | $C_{25}H_{31}N_7OS_2$ |
| Formula weight | 621.69 |
| Temperature | 298(2) K |
| Wavelength | 1.54178 Å |
| Crystal size | 0.500 × 0.220 × 0.150 mm |
| Crystal habit | Colourless Column |
| Crystal system | Triclinic |
| Space group | P-1 |
| Unit cell dimensions | a = 8.7831(6) Å    α = 98.108(6)° |
| | b = 11.8484(8) Å   β = 100.955(6)° |
| | c = 14.2485(10) Å  γ = 98.861(6)° |
| Volume | 1416.05(17) Å³ |
| Z | 2 |
| Density (calculated) | 1.458 Mg/m³ |
| Absorption coefficient | 2.239 mm⁻¹ |
| F(000)2 | 652 |

B. Dry Granulation Formulation of a bis-mesylate Salt of Formula IA ("Formulation I")

The following Examples are directed to the dry granulation tablet of Form 3, the monohydrate, bis-mesylate salt of Formula IA prepared according to Example A above. It should be understood that the dry granulation tablet of the monohydrate, bis-mesylate salt of Formula IA may also be generally referred herein as "Formulation 1".

Example B1

Manufacturing Process

This example demonstrates the preparation of the monohydrate, bis-mesylate salt of Formula IA as a tablet using a dry granulation process.

Methods

Figure 2A:
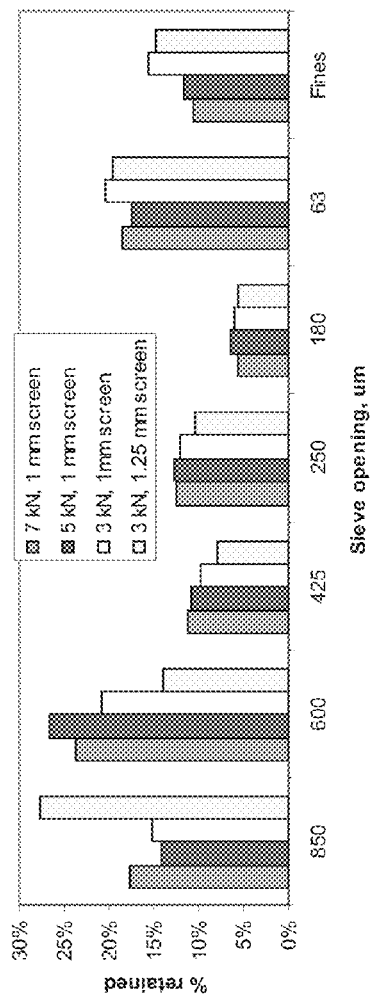
FIG. 2A is a graph comparing the particle size distributions obtained by sieve analysis of the final blends of Formulation 1 (the dry granulation tablet of a monohydrate, bis-mesylate salt of Formula IA) prepared with various processing parameters.

An intragranular powder blend made up of monohydrate, bis-mesylate salt of Formula IA, mannitol, HPMC, crospovidone, poloxamer 188, and colloidal silicon dioxide was prepared and then divided into four sublots for roller compaction using different compaction forces or mill screen sizes on a Gertise minipactor. The following parameters were used: smooth roller on the left and knurled roller on the right; gap at 2 mm; roller speed at 3 rpm; and the granulator at 60 rpm. Each sub-lot was mixed with extra-granular excipients (including magnesium stearate, microcrystalline cellulose and crospovidone), and the final blend was characterized for particle size, flowability by Flodex, bulk density, tap density, and compression profile. The results are summarized in Table 1 below, and FIG. 2A.

TABLE 1

Processing parameters and characterization of the final blends of Formulation 1

| Compact Force (kN/cm) | Screen (mm) | Mean particle size (μm) | Flodex (mm) | Bulk Density (g/mL) | Tap Density (g/mL) |
|---|---|---|---|---|---|
| 7 | 1.0 | 326 | 12 | 0.55 | 0.75 |
| 5 | | 313 | 12 | 0.55 | 0.71 |
| 3 | | 267 | 12 | 0.52 | 0.67 |
| 3 | 1.25 | 299 | 14 | 0.55 | 0.68 |

Figure 2B:
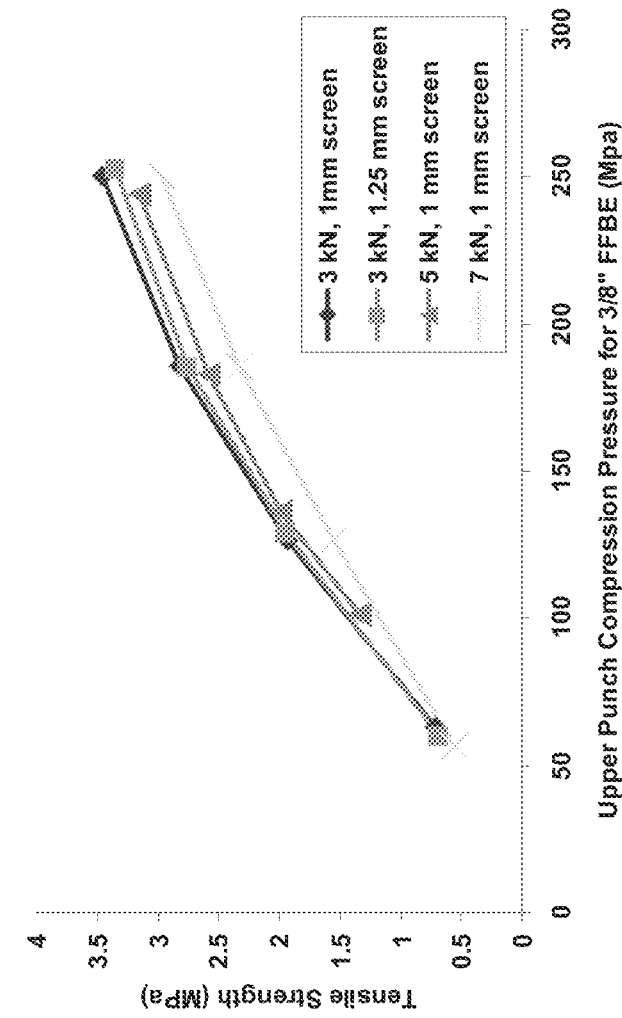
FIG. 2B is a graph depicting compression profiles of various blends of Formulation 1 prepared with various processing parameters.

At the same mill screen size, 1 mm, the particle size was observed to be dependent on the compaction force. Higher compaction force was observed to lead to bigger mean particle size as well as higher bulk density and tap density. However, the Flodex stayed the same at 12 mm for all three compaction forces tested. When mill screen size was changed to 1.25 mm while the compaction force was maintained at 3 KN, Flodex increased to 14 mm and mean particle size, bulk density and tap density all increased slightly. As shown in FIG. 2B, all blends were observed to have good compressibility although the sub-lot with higher compaction force showed slightly lower compressibility. In summary, the manufacturing process for Fm appeared robust within the ranges of the processing parameters tested. The composition of this final formulation is listed in Table 2 below.

TABLE 2

Representative composition of monohydrate, bis-mesylate salt of Formula IA (Form 3), 200 mg (Formulation 1)

| Components | Composition % w/w | Composition mg/unit | Compendial Reference | Function |
|---|---|---|---|---|
| hydroxypropyl-methylcellulose | 36.68 | 293.4ᵃ | HSE | Active |
| Mannitol | 27.82 | 222.6 | USP/Ph. Eur. | Diluent |
| Crospovidone | 10.00 | 80.0 | NF/Ph. Eur. | Disintegrant |
| Hypromellose | 15.00 | 120.0 | USP | Precipitation inhibitor |
| Poloxamer 188 | 3.00 | 24.0 | NF/Ph. Eur. | Surfactant |
| Colloidal Silicon Dioxide | 1.00 | 8.0 | HSE | Glidant |
| Microcrystalline Cellulose | 5.00 | 40.0 | NF/Ph. Eur. | Diluent |
| Magnesium Stearate | 1.50 | 12.0 | NF/Ph. Eur. | Lubricant |
| Tablet Core Weight | 100.00 | 800.0 | | |
| Opadry II, 85F90616, Blue | 3.00 | 24.0ᶜ | HSE | Film coat |
| Purified Waterᵇ, | — | — | USP/Ph. Eur. | Solvent |
| Total Tablet Weight | | 824.0 | | |

ᵃEquivalent to 200 mg/tablet of the compound of Formula I as a free base
ᵇPurified water is used for coating and is removed during the process
ᶜRepresents a theoretical weight gain of 3.0% onto the tablet core weight Example B2

Disintegration Study

This Example demonstrates the effect of various disintegrants and diluents used in the dry granulation tablet prepared according to Example B1 above. The disintegrants screened in this Example include: crospovidone (Polyplasdone XL), croscarmellose sodium (Ac-Di-Sol), sodium starch glycolate (Explotab), Pharmaburst, F-melt, and Amberlite. The formulations used for the screening of disintegration (namely, Formulations Fa, Fb, Fc, Fd, Fe, and Ff) are summarized in Table 3 below.

TABLE 3

Composition of formulations used for disintegrant screening and the disintegration study results

| | | Composition (%) | | | | | |
|---|---|---|---|---|---|---|---|
| | Component | Fa | Fb | Fc | Fd | Fe | Ff |
| Intra-granular | Monohydrate, bis-mesylate salt of Formula IA (Form 3) | 36.68[1] | 36.68[1] | 36.68[1] | 36.68[1] | 36.68[1] | 36.68[1] |
| | Lactose monohydrate (SuperTab 11 SD) | 24.32 | 24.32 | 24.32 | 24.32 | 24.32 | 24.32 |
| | Microcrystalline Cellulose (Avecel PH 102) | 15.00 | 15.00 | 15.00 | 15.00 | 15.00 | 15.00 |
| | crospovidone (Polyplasdone XL) | 10.00 | — | — | — | — | — |
| | croscarmellose sodium (Ac-Di-Sol) | — | 10.00 | — | — | — | — |
| | sodium starch glycolate (Explotab) | — | — | 10.00 | — | — | — |
| | Pharmaburst | — | — | — | 10.00 | — | — |
| | F-melt | — | — | — | — | 10.00 | — |
| | Amberlite | — | — | — | — | — | 10.00 |
| | Mg Stearate (Hyqual Code 5712) | 1.25 | 1.25 | 1.25 | 1.25 | 1.25 | 1.25 |
| Extra-granular | Disintegrant | 2.00 | 2.00 | 2.00 | 2.00 | 2.00 | 2.00 |
| | Microcrystalline Cellulose (Avicel PH 102) | 10.00 | 10.00 | 10.00 | 10.00 | 10.00 | 10.00 |
| | Mg Stearate (Hyqual Code 5712) | 0.75 | 0.75 | 0.75 | 0.75 | 0.75 | 0.75 |
| Total | | 100 | 100 | 100 | 100 | 100 | 100 |
| % Remaining after 10 min in Disintegration test[2] | | 40 | 50 | 45 | 40 | 45 | 100 |

[1]Equivalent to 25% the compound of Formula I as a free base. Actual monohydrate, bis-mesylate salt of Formula IA (Form 3) amount was adjusted based on the drug content factor (DCF) with a concomitant adjustment to the amount of lactose monohydrate.
[2]Disintegration test was performed in 0.01N HCL at 37° C. using the USP disintegration apparatus.

The disintegrants were screened using standard USP disintegration apparatus in 0.01 N HCl at 37° C. The percentage of the tablet remaining after 10 minutes was visually estimated. Only the intragranular excipients of the formulation were mixed and 350 mg of the mixture was compressed into a tablet with a hardness of 8-10 Kp for this disintegration study.

The results of this disintegrant screen are summarized in Table 3 above. Crospovidone and Pharmburst formulations (i.e., Fa and Fd, respectively) was observed to have the fastest erosion.

In subsequent studies, while keeping crospovidone as the disintegrant, the following diluents were compared to the diluents used in Fa: mannitol, pregelatinized starch, calcium phosphate, and succinic acid. The formulation composition and the results of the disintegration test are summarized in Table 4 below. As seen in the table below, the mannitol formulation (Fg) showed the fastest erosion.

TABLE 4

Composition of formulations used for diluent screening and the disintegration study results

| | | Composition (%) | | | | |
|---|---|---|---|---|---|---|
| | Component | Fa | Fg | Fh | Fi | Fj |
| Intra-granular | Monohydrate, bis-mesylate salt of Formula IA (Form 3) | 36.68[1] | 36.68[1] | 36.68[1] | 36.68[1] | 36.68[1] |
| | Lactose monohydrate (SuperTab 11 SD) | 24.32 | — | — | — | — |
| | Crospovidone (Polyplasdone XL) | 10.00 | 10.00 | 10.00 | 10.00 | 10.00 |
| | Microcrystalline Cellulose (Avecel PH 102) | 15.00 | — | — | — | — |
| | Mannitol | — | 39.32 | — | — | — |
| | Pregelatinized Starch | — | — | 39.32 | — | — |
| | Calcium Phosphate | — | — | — | 39.32 | — |
| | Succinic Acid | — | — | — | — | 39.32 |
| | Mg Stearate (Hyqual Code 5712) | 1.25 | 1.25 | 1.25 | 1.25 | 1.25 |

TABLE 4-continued

Composition of formulations used for diluent screening and the disintegration study results

|  | Component | Composition (%) | | | | |
|---|---|---|---|---|---|---|
|  |  | Fa | Fg | Fh | Fi | Fj |
| Extra-granular | Disintegrant | 2.00 | 2.00 | 2.00 | 2.00 | 2.00 |
|  | Microcrystalline Cellulose (Avicel PH 102) | 10.00 | 10.00 | 10.00 | 10.00 | 10.00 |
|  | Mg Stearate (Hyqual Code 5712) | 0.75 | 0.75 | 0.75 | 0.75 | 0.75 |
| Total |  | 100 | 100 | 100 | 100 | 100 |
| % Remaining after 10 min in Disintegration test[2] |  | 40 | 20 | 40 | 90 | 40 |

[1]Equivalent to 25% the compound of Formula I as a free base. Actual monohydrate, bis-mesylate salt of Formula IA (Form 3) amount was adjusted based on the drug content factor (DCF) with a concomitant adjustment to the amount of lactose monohydrate for Fa, mannitol for Fg, pregelatinized starch for Fh, calcium phosphate for Fh, and succinic acid for Fj.
[2]Disintegration test was performed in 0.01N HCL at 37° C. using the USP disintegration apparatus.

Example B3

Dissolution Study

This Example demonstrates the effect of various precipitation inhibitors and surfactants used in the dry granulation formulation prepared according to Example B1 above. Formulations Fk, Fl, and Fm were tested and their compositions are shown in Table 5 below.

TABLE 5

Composition of formulations Fk, Fl, and Fm

|  | Component | Composition (%) | | |
|---|---|---|---|---|
|  |  | Fk | Fl | Fm |
| Intragranular | Monohydrate, bis-mesylate salt of Formula IA (Form 3) | 36.71[1] | 36.71[1] | 36.71[1] |
|  | Mannitol (Pearlitol SD 100) | 42.79 | 27.79 | 27.79 |
|  | Hypromellose (Methocel LV E3) | — | 15.00 | 15.00 |
|  | Crospovidone (polyplasdone XL) | 5.00 | 5.00 | 5.00 |
|  | Poloxamer 407 (Lutrol micro 127) | 3.00 | 3.00 | — |
|  | Poloxamer 188 (Lutrol micro 68) | — | — | 3.00 |
|  | Colloidal Silicon Dioxide (Aerosil 200) | 1.00 | 1.00 | 1.00 |
|  | Magnesium Stearate (Hyqual Code 5712) | 0.75 | 0.75 | 0.75 |
| Extragranular | Crospovidone (polyplasdone XL) | 5.00 | 5.00 | 5.00 |
|  | Microcrystalline Cellulose (Avicel PH 102) | 5.00 | 5.00 | 5.00 |
|  | Magnesium Stearate (Hyqual Code 5712) | 0.75 | 0.75 | 0.75 |
| Total |  | 100.00 | 100.00 | 100.00 |

[1]Equivalent to 25% the compound of Formula I free base. Actual monohydrate, bis-mesylate salt of Formula IA (Form 3) amount was adjusted based on DCF with a concomitant adjustment to the amount of mannitol.

The three formulations were tested using a USP paddle apparatus at 75 rpm with 900 mL of pH 4.5, 50 mM sodium acetate buffer with 1% cetyltrimethylammonium bromide (CTAB) as the medium, maintained at 37° C. The extent of the compound of Formula I released over time was monitored by a HPLC method.

The dissolution of the Formulation Fx 200 mg tablet (whose composition is shown in Table 6 below) was also tested using the same method.

TABLE 6

Representative composition of mono-mesylate salt of Formula IIA as tablets (200 mg) ("Formulation Fx")

| Components | Composition | | Compendial Reference | Function |
|---|---|---|---|---|
|  | % w/w | mg/unit |  |  |
| Mono-Mesylate salt of the compound of Formula I | 37.01 | 246.86[a] | HSE | Active |
| Lactose Monohydrate | 21.99 | 146.67 | NF/Ph. Eur. | Diluent |
| Microcrystalline Cellulose | 25.00 | 166.75 | NF/Ph. Eur. | Diluent |
| Crospovidone |  | 33.35 | NF/Ph. Eur. | Disintegrant |
| Povidone | 2.00 | 13.34 | USP/Ph. Eur. | Binder |
| Sodium Lauryl Sulfate | 3.00 | 20.01 | NF/Ph. Eur. | Surfactant |
| Colloidal Silicon Dioxide | 5.00 | 33.35 | HSE | Antiadherent |
| Magnesium Stearate | 1.00 | 6.67 | NF/Ph. Eur. | Lubricant |
| Purified Water[b] | — | — | USP/Ph. Eur. | Granulation fluid |
| Tablet Core Weight | 100 | 667 |  |  |
| Opadry II, 85F90616, Blue | 3.00 | 20.00[c] | HSE | Film coat |
| Purified Water[b], | — | — | USP/Ph. Eur. | Solvent |
| Total Tablet Weight |  | 687 |  |  |

Figure 3:
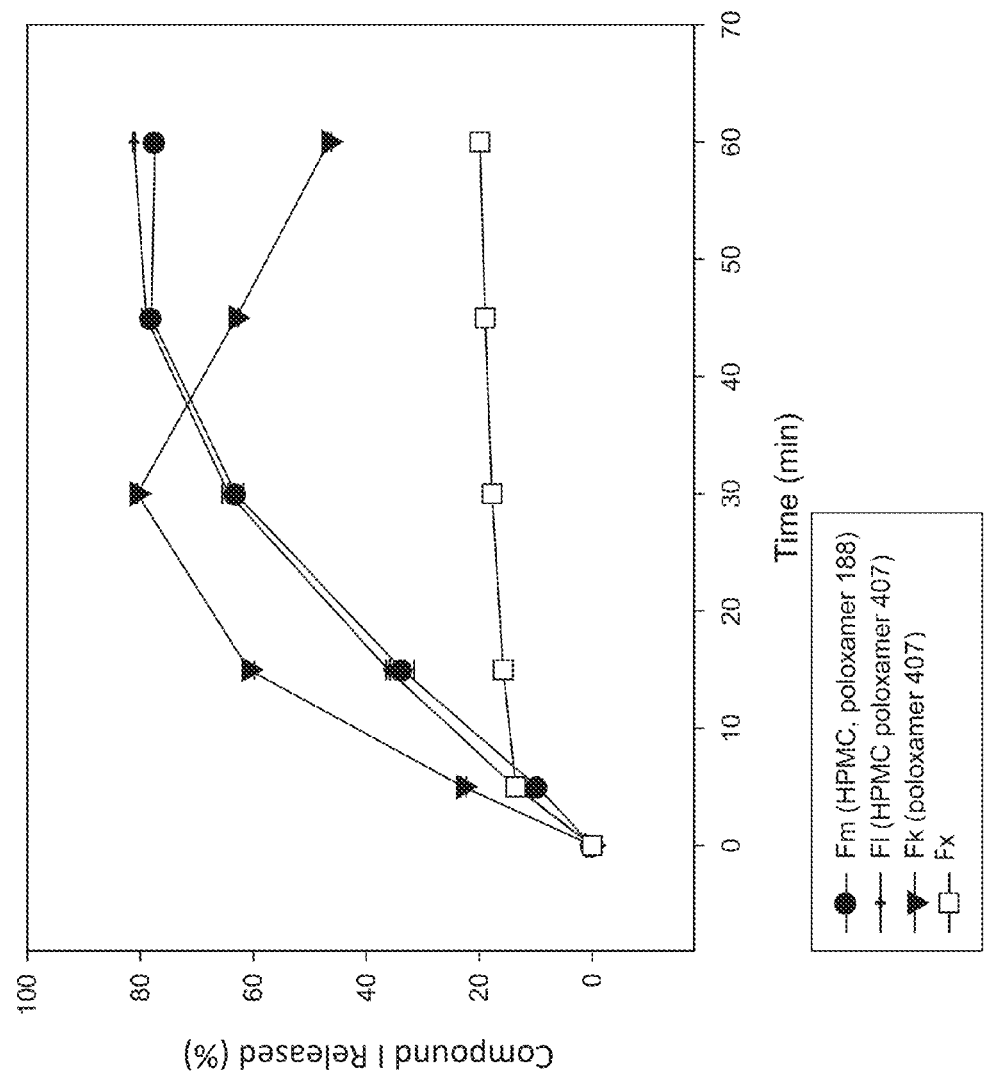
FIG. 3 is a graph depicting dissolution profiles of Formulations Fk, Fl, Fm, and Fx in pH 4.5, 50 mM Acetate Buffer Containing 1% CTAB.

[a]Equivalent to 200 mg/tablet of the compound of Formula I free base
[b]Purified water is used in granulation and coating processes and removed during processing
[c]Represents a theoretical weight gain of 3.0% onto the tablet core weight The dissolution profiles of all four formulations are shown in FIG. 3. In Formulation Fx, 20% of the compound of Formula I was dissolved within one hour. In contrast, the dissolution of the compound of Formula I in all Formulations Fk, Fl, and Fm was 80% within one hour. Among Formulations Fk, Fl, and Fm, Fk dissolved faster and reached peak dissolution at 30 min. From 30-60 min, the amount of the compound of Formula I in Formulation Fk decreased quickly. Compared to Formulation Fk, Formulations Fl and Fm dissolved slower and reached the peak at 45 min, but the amount of the compound of Formula I in solution was not decreased before 60 min. These results indicated that HPMC is critical in maintaining the supersaturation.

Example B4

Effect of Mannitol

This Example demonstrates the effect of mannitol in the dry granulation tablet prepared according to Example B1 above. The components of the formulations used in this Example, and the amounts of such components, are summarized in Table 7 below.

TABLE 7

Composition of formulations used

| | Component | Composition (%) MCC | Mannitol |
|---|---|---|---|
| Intragranular | Monohydrate, bis-mesylate salt of Formula IA | 39.48[1] | 39.48[1] |
| | Microcrystalline Cellulose 105 | 13.27 | — |
| | Mannitol SD 100 | — | 13.27 |
| | Crospovidone XL | 10.00 | 10.00 |
| | Kleptose | 20.00 | 20.00 |
| | HPMC E3 LV | 10.00 | 10.00 |
| | Lutrol 68 | 3.00 | 3.00 |
| | Aerosil 200 | 1.00 | 1.00 |
| | Magnesium Stearate | 0.50 | 0.50 |
| Extragranular | MCC 102 | 2.00 | — |
| | Crospovidone XL | 10.00 | 2.00 |
| | Magnesium Stearate | 0.75 | 0.75 |

[1]Equivalent to 25% free base

The formulations were tested using standard USP disintegration apparatus in 0.01 N HCl at 37° C. The percentage of the tablet remaining at different time points was visually estimated, and the results are summarized in Table 8 below. As seen in Table 8, a lower percentage of the tablet remained over the course of 30 minutes (i.e., a greater percentage of the tablet disintegrated after 10 minutes) when mannitol was used compared to microcrystalline cellulose. Thus, this Example demonstrates that mannitol increased the erosion rate of the tablet.

TABLE 8

Disintegration study results

| | % Remaining | |
|---|---|---|
| Time (minutes) | Microcrystalline Cellulose 5696-62 | Mannitol 5696-63 |
| 0 | 100 | 100 |
| 5 | 90 | 80 |
| 10 | 80 | 50 |
| 15 | 45 | 25 |
| 20 | 25 | 10 |
| 25 | 10 | 5 |
| 30 | 5 | 0 |

Example B5

Pharmacokinetic Study in Dog Model

This Example demonstrates the pharmacokinetic effects of administering the Formulation Fx (summarized in Example B3 above) and Formulations Fm and Fl to pentagastrin- or famotidine-pretreated dogs.

Pentagastrin pretreatment (6 µg/kg intramuscular injection 30 minutes prior to test formulation dosing) in fasted dogs was used to simulate fasting gastric pH in humans. Famotidine pretreatment (20 mg orally 1 hour prior to test formulation dosing) in fasted dogs was used to simulate human gastric pH when acid suppressant was co-dosed with test formulation. The results of this study are summarized in Table 9 below.

TABLE 9

PK data of the compound of Formula I tablet formulations in dogs

| Dose (mg) | Dog Pretreatment | Formulation | F (%) Mean | AUC0-24 (µM · hr) Mean | SD | Cmax (µM) Mean | SD | Tmax (hr) Mean | SD |
|---|---|---|---|---|---|---|---|---|---|
| 100 | pentagastrin | Fx | 34 | 11 | 1.8 | 1.6 | 0.2 | 2.7 | 1.2 |
| 100 | famotidine | | 0.2 | 0.06 | 0.01 | 0.02 | 0.002 | 1.7 | 0.6 |
| 100 | pentagastrin | Fm | 13 | 4.1 | 1.4 | 0.8 | 0.2 | 1.8 | 0.4 |
| 100 | famotidine | | 15 | 4.9 | 4.2 | 0.7 | 0.5 | 4.9 | 9.4 |
| 100 | famotidine | Fl | 2.2 | 0.66 | 0.25 | 0.13 | 0.06 | 2.0 | 2.0 |

Figure 11:
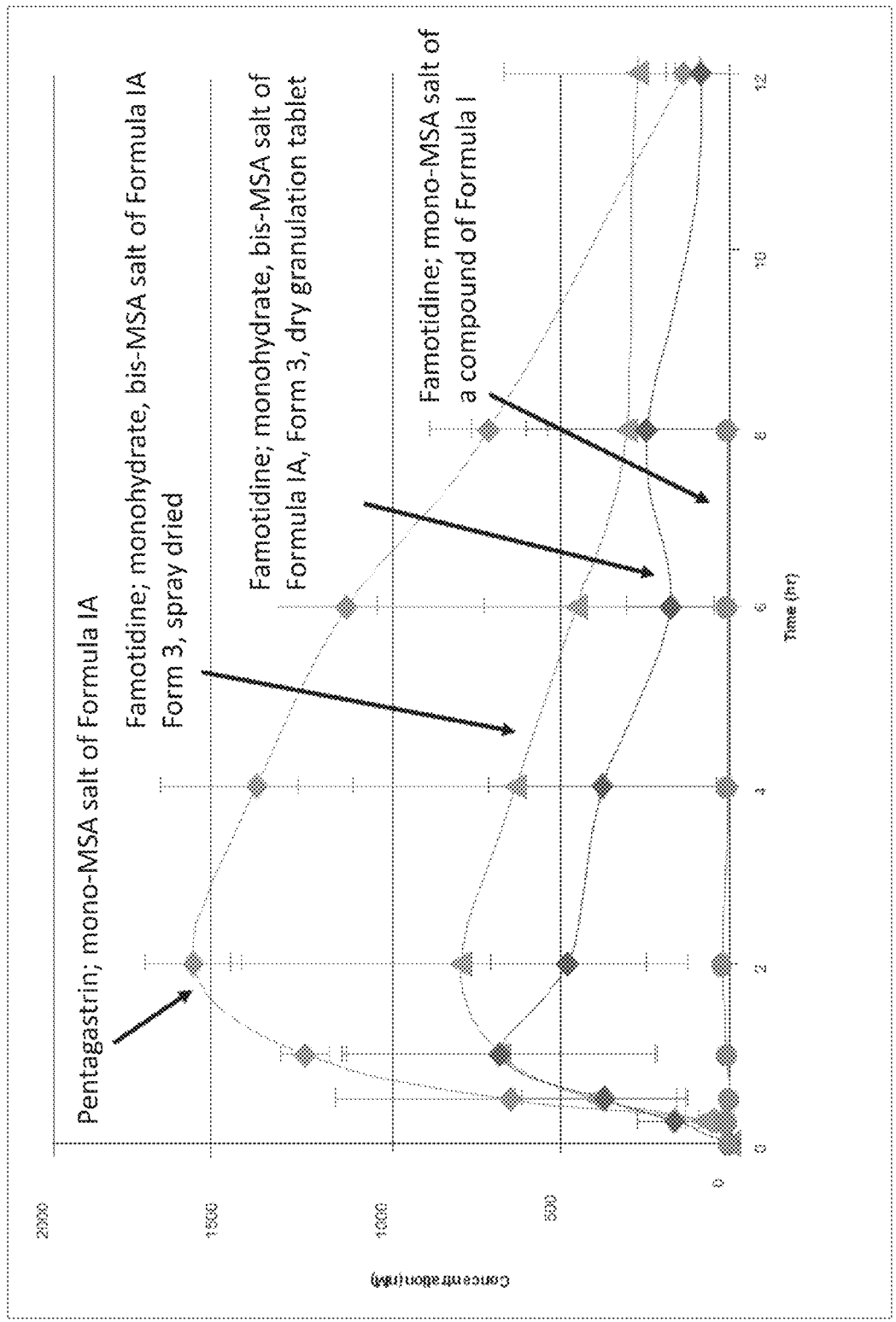
FIG. 11 is a graph depicting exposure in pentagastrin- and famotidine-pretreated dogs administered with Formulation Fx (tablet comprising a mono-mesylate salt of Formula IIA, incorporated by wet granulation), Formulation 1 (tablet comprising a monohydrate, bis-mesylate salt of the compound of Formula I, incorporated by dry granulation), or Formulation 2 (tablet comprising a bis-mesylate salt of the compound of Formula I, incorporated as a solid dispersion).

As shown in this table, for Formulation Fx, the exposure in famotidine-pretreated dogs decreased by more than 100 folds compared to in pentagastrin-pretreated dogs. In contrast, as seen in FIG. 11, Formulation Fm was observed to increase exposure in famotidine-pretreated dogs by about 75-fold. Furthermore, the exposure in famotidine-pretreated dogs was observed to be similar to the exposure in pentagastrin-pretreated dogs, which suggest that Formulation Fm could minimize the drug-drug-interaction with acid suppressants in human.

Example B6

Stability Studies

This Example demonstrates the stability of Formulation Fd, described in Example B2 above.

Figure 4:
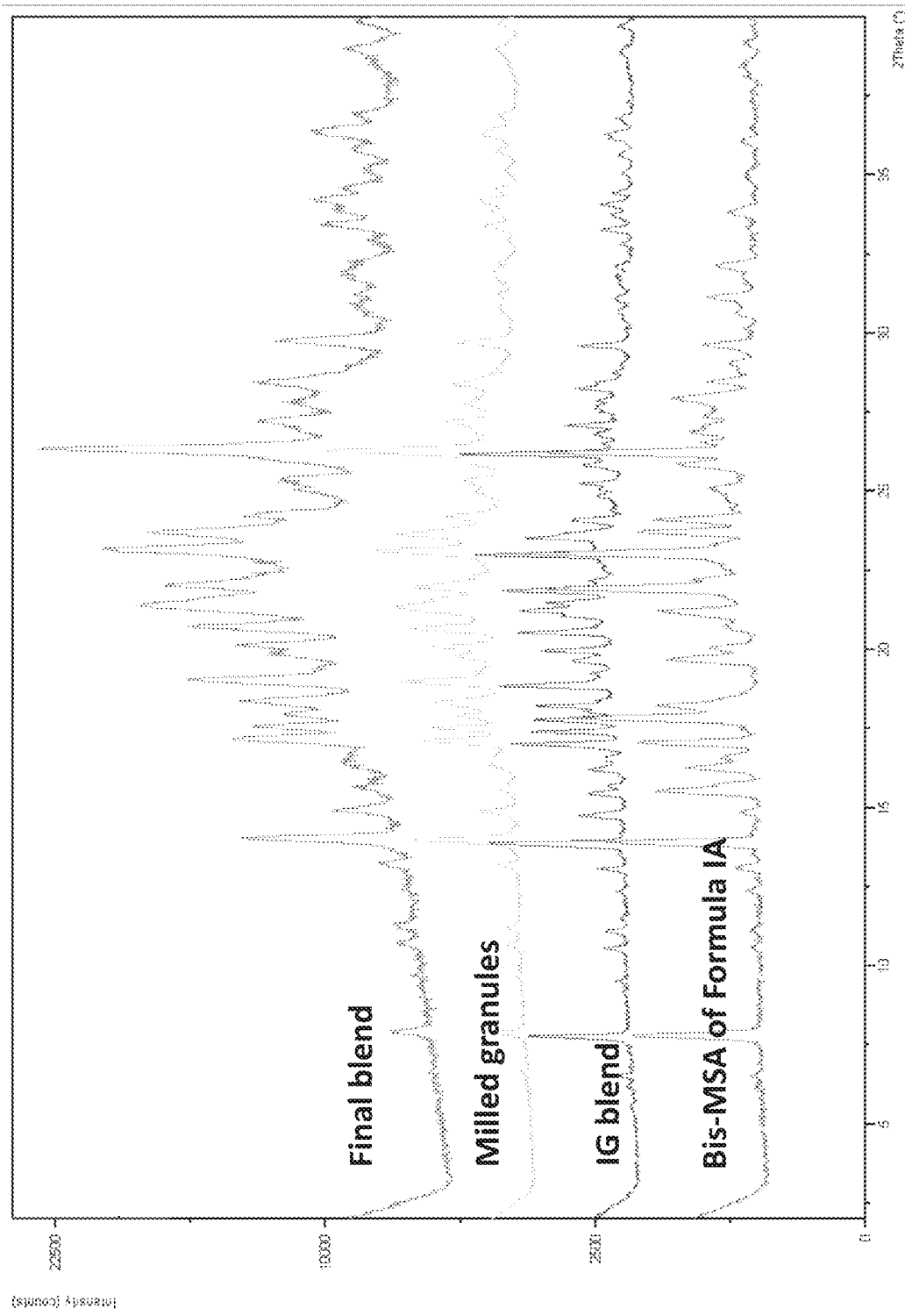
FIG. 4 is an XRPD pattern of a monohydrate, bis-mesylate salt of Formula IA and the intragranular blend, the milled granules, and the final blend of Formulation 1 prepared using the same monohydrate, bis-mesylate salt of Formula IA.

The physical stability of a bis-mesylate salt of Formula IA during processing was examined by powder X-ray diffraction (XRPD) and no form change was observed as shown in FIG. 4.

The chemical and physical stability of the tablets during storage was also studied. Ten tablets were packaged in each 100 mL high density polyethylene (HDPE) bottle containing 0 or 3 g silica gel desiccant. The bottles were capped with a polypropylene screw cap fitted with an induction-sealed, aluminum-faced liner. The bottles were kept at the following conditions: 25° C./60% RH, 40° C./75% RH, and 60° C. The tablets were analyzed by HPLC for chemical stability and by XRPD for physical stability.

As shown in Table 10 below, the tablets are chemically stable.

TABLE 10

Stability data of dry granulation tablet

| Conditions | Time point | Strength % | Compound of Formula I AN % | Total Impurity % | RRT 0.55 | RRT 0.70 | RRT 0.74 | RRT 0.93 | RRT 1.29 |
|---|---|---|---|---|---|---|---|---|---|
|  | Initial | 100.2 | 99.6 | 0.3 | — | trace | — | — | 0.32 |
| 25/60, | 1 month | 99.4 | 99.5 | 0.4 | — | trace | — | — | 0.37 |
| 3 g desiccant | 3 months | 100.0 | 99.7 | 0.3 | — | — | — | — | 0.33 |
| 40/75, | 2 weeks | 100.0 | 99.5 | 0.4 | — | — | — | — | 0.37 |
| 3 g desiccant | 1 month | 99.1 | 99.5 | 0.4 | trace | trace | — | trace | 0.36 |
|  | 3 months | 99.4 | 99.5 | 0.4 | trace | — | 0.05 | trace | 0.37 |
| 40/75, | 2 weeks | 99.2 | 99.4 | 0.5 | trace | 0.06 | — | 0.06 | 0.37 |
| no desiccant | 1 month | 99.0 | 99.4 | 0.5 | trace | 0.06 | — | 0.08 | 0.35 |
|  | 3 months | 98.4 | 99.5 | 0.5 | 0.08 | — | 0.05 | 0.06 | 0.32 |
| 60 C., | 2 weeks | 99.5 | 99.4 | 0.5 | trace | 0.06 | — | 0.08 | 0.35 |
| no desiccant | 1 month | 98.8 | 99.4 | 0.5 | trace | 0.07 | — | 0.09 | 0.33 |
|  | 3 months | 99.2 | 99.5 | 0.5 | 0.09 | — | 0.06 | 0.07 | 0.28 |

Trace: <0.05%

Ten (10) tablets packaged in 100 mL, white, high density polyethylene HDPE bottles containing three or zero gram Tri-sorb desiccant. Each bottle is capped using a white, continuous thread, child-resistant polypropylene screw cap with an induction sealed, aluminum-faced liner.

At 25° C./60% RH, no new degradants were observed while only RRT 1.29 impurity increased slightly. At 40° C./75% RH after 3 months, only 0.1% increase of total impurity was observed in the presence of desiccant while 0.2% increase was observed in the absence of desiccant. At 60° C. in the absence of desiccant, the stability was similar to at 40° C./75%. XRPD was performed at 3 month time point and no form change was observed (data not shown).

C. Solid Dispersion Formulation of a bis-mesylate salt of Formula IA ("Formulation 2")

The following Examples are directed to the solid dispersion formulation of Form 3, the monohydrate, bis-mesylate salt of Formula IA (such as the monohydrate thereof), which was prepared according to Example A above. It should be understood that solid dispersion tablet of the bis-mesylate salt of Formula IA may also be generally referred herein as "Formulation 2".

Example C1

Spray Drying and Tableting Process

This example demonstrates the preparation of a tablet comprising a spray-dried dispersion of the bis-mesylate salt of Formula IA.

Bis-mesylate salt of Formula IA was combined with hypromellose 2910 and purified water, and spray dried, followed by secondary drying when necessary. The quantitative composition of the feed solution and resulting spray-dried powder is shown in Table 11 below.

TABLE 11

Representative composition of a bis-mesylate salt of Formula IA feed solution and spray-dried powder

| Component | Feed Solution (% w/w) | Spray-Dried Powder (% w/w) |
|---|---|---|
| Monohydrate, Bis-mesylate Salt of Formula IA (Form 3) | 7.34$^a$ | 49.5$^b$ |

TABLE 11-continued

Representative composition of a bis-mesylate salt of Formula IA feed solution and spray-dried powder

| Component | Feed Solution (% w/w) | Spray-Dried Powder (% w/w) |
|---|---|---|
| HPMC E3 | 7.5 | 50.5$^c$ |
| Water | QS | — |
| Total | 100.0 | 100.0 |

$^a$Equivalent to 5.0% of the compound of Formula I as a free base in the feed solution.
$^b$Equivalent to 33.7% of the compound of Formula I as a free base in the bulk powder.
$^c$The ratio of the compound of Formula I as a free base to HPMC E3 is 1:1.5 (w/w).

The 15% solids feed solution showed acceptable viscosity (~10 cP) and chemical stability at ambient conditions in both glass and stainless steel containers, as shown in Table 12 below.

TABLE 12

Chemical stability of a bis-mesylate salt of Formula IA aqueous spray-dry feed solution (15% solids)

| | Glass Beaker | | Stainless Steel Beaker | |
|---|---|---|---|---|
| Time (days) | Compound of Formula I (% AN) | Total Imp/Deg (% AN) | Compound of Formula I (% AN) | Total Imp/Deg (% AN) |
| 0 | 99.66 | 0.34 | 99.66 | 0.34 |
| 1 | 99.77 | 0.23 | 99.74 | 0.26 |
| 8 | 99.79 | 0.21 | 99.82 | 0.18 |
| 14 | 99.69 | 0.31 | 99.75 | 0.25 |

Over the course of the feed solution stability experiment, the pH remained constant at ~1.3 and no precipitation or gelling was observed. The spray drying process was assessed using an Anhydro MS35 spray dryer. Solid-state properties of the spray-dried powder are outlined in Table 13 below. All of the feasibility batches had similar particle size, water content, and high $T_g$ values ranging from 135° C. to 140° C.

TABLE 13

Solid-state characteristics of the spray-dried feasibility batches

| Characteristic | Compound of Formula I: HPMC E3 Spray-Dried Powder |
|---|---|
| Particle Size Range (PLM) | 5-50 µm |
| Water Content (KF) | 3-5% |
| Bulk Density (g/mL)$^a$ | 0.27 |
| Tap Density (g/mL)$^a$ | 0.31 |
| $T_g$ (mDSC) | 135° C.-140° C. |

The resulting solid dispersion (33.7% w/w of the compound of Formula I) was blended and milled with mannitol, poloxamer 188, crospovidone, and colloidal silicon dioxide, which was then blended with magnesium stearate, crospovidone, and microcrystalline cellulose and compressed to form a tablet.

Figure 8A:
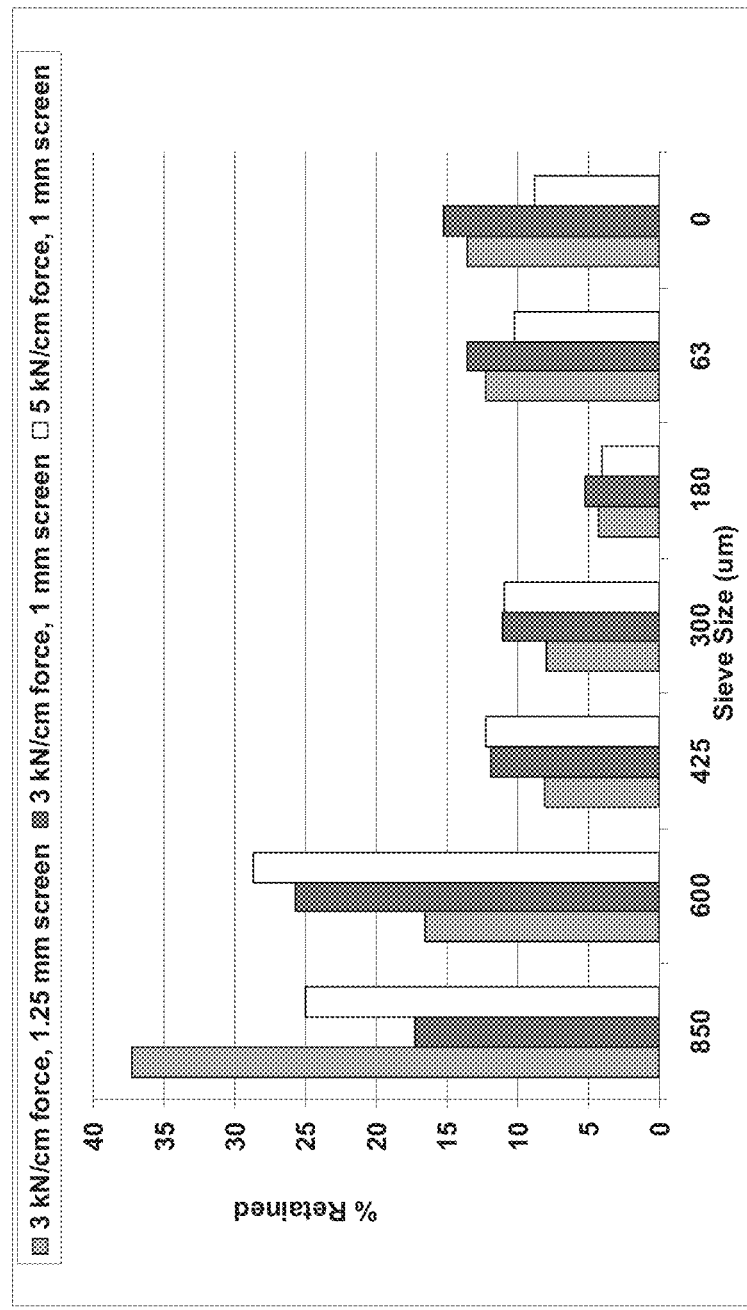
FIG. 8A is a graph comparing the particle size distribution obtained by sieve analysis of the final blends of Formulation 2 (the solid dispersion tablet of a bis-mesylate salt of Formula IA) prepared using various roller compaction process parameters.

Process optimization focused on the effect of two key parameters, compaction force and mill screen size, on the roller compaction process. Approximately 1.8 kg of intragranular powder blend was prepared and then divided into three sub-lots for roller compaction using different compaction forces (3 or 5 kN/cm) and mill screen sizes (1 or 1.25 mm). The following parameters were kept used: left smooth, right knurled rollers, 2 mm gap, and roller speed of 3 rpm. Final blends of each sub-lot were prepared and characterized for particle size, flowability by Flodex, bulk and tap density, and compression profile. The results are summarized in Table 14 and FIG. 8A.

TABLE 14

Processing parameters and characterization of the final blends of Formulation 2

| Compaction Force (kN/cm) | Screen (mm) | Mean particle size (µm) | Flodex (mm) | Bulk Density (g/mL) | Tap Density (g/mL) |
|---|---|---|---|---|---|
| 3 | 1.25 | 379 | 14 | 0.50 | 0.61 |
| 3 | 1 | 311 | 14 | 0.46 | 0.67 |
| 5 | 1 | 421 | 12 | 0.52 | 0.67 |

Figure 8B:
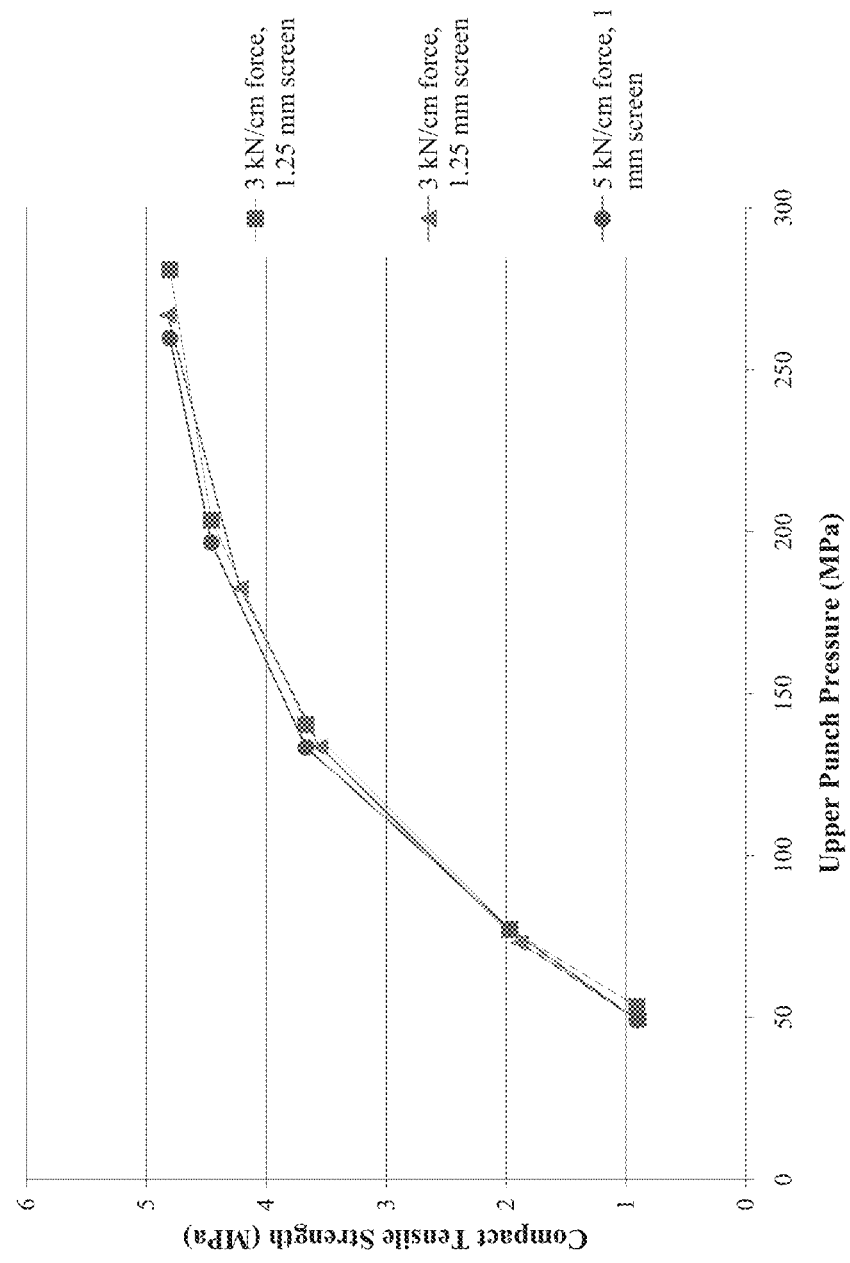
FIG. 8B is a graph depicting compression profiles of various blends of Formulation 2 prepared using various process parameters (including, for example, roller compaction process parameters).

When screen size was kept at 1 mm, the higher compaction force of 5 kN/cm resulted in larger mean particle size, higher bulk and tap density, and better flow. As shown in FIG. 8B, all of the blends were highly compressible.

The composition of this final formulation is listed in Table 15 below.

TABLE 15

Representative composition of solid dispersion tablet of a bis-mesylate salt of Formula IA, 200 mg (Formulation 2)

| Components | Composition % w/w | mg/unit | Compendial Reference | Function |
|---|---|---|---|---|
| Compound of Formula I Solid Dispersion, 33.7% w/w, Bulk Powder | 59.35 | 593.50$^a$ | HSE | Active |
| Mannitol (Pearlitol 100 SD) | 22.40 | 224.0 | USP/Ph. Eur. | Diluent |
| Crospovidone (Polypasdone XL) | 10.00 | 100.0 | NF/Ph. Eur. | Disintegrant |
| Poloxamer 188 (Lutrol Micro 68) | 3.00 | 30.0 | NF/Ph. Eur. | Surfactant |
| Colloidal Silicon Dioxide (Aerosil 200) | 1.00 | 10.0 | HSE | Glidant |
| Microcrystalline Cellulose (Avicel PH 102) | 3.00 | 30.0 | NF/Ph. Eur. | Diluent |
| Magnesium Stearate (Hyqual Code 5712) | 1.25 | 12.5 | NF/Ph. Eur. | Lubricant |
| Tablet Core Weight | 100.00 | 1000.0 | | |
| Opadry II Blue 85F90616 | 3.00 | 30.0$^c$ | HSE | Film coat |
| Purified Water$^b$ | — | — | USP/Ph. Eur. | Solvent |
| Total Tablet Weight | | 1030.0 | | |

$^a$Equivalent to 200 mg/tablet the compound of Formula I free base
$^b$Purified water is used for coating and is removed during the process
$^c$Represents a theoretical weight gain of 3.0% onto the tablet core weight Example C2

Polymer Screening

This Example demonstrates the effect of various polymers used in the spray-dry formulation prepared according to the protocol set forth in Example C1 above.

Spray-dried powders were prepared from the monohydrate, bis-mesylate salt of the compound of Formula I (Form 3) using a 1:2 ratio of the compound of Formula I as free base:Polymer ratios of 1:2 (w/w) with the polymers listed in Table 16 below.

TABLE 16

Physical stability of spray-dried mixtures of polymers with monohydrate, bis-mesylate salt of Formula IA (Form 3)

| Polymer | Compound of Formula I (free base):Polymer ratio (w/w) | XRPD After Open Storage at 40° C./75% RH for 4 weeks |
|---|---|---|
| No polymer | N/A | Crystallized$^a$ |
| PVP K29-32 | 1:2 | Crystallized |
| PVP VA-64 | 1:2 | Crystallized |
| HPMC E3 | 1:2 | No change |
| HPB-CD | 1:2 | Crystallized$^a$ |
| HPMC E3 and HPB-CD | 1:1:1 | Crystallized$^a$ |

$^a$Samples crystallized after 2 weeks.

Physical stability of the spray-dried powder was assessed after storage at 40° C./75% RH open condition using X-Ray Powder Diffraction (XRPD). As seen in the table above, hydroxypropylmethylcellulose (HPMC) was surprisingly observed to be the only polymer tested found to prevent crystallization.

Example C3

Disintegration Study

This Example demonstrates the effect of various excipients for use in the spray-dry solid dispersion formulation for the bis-mesylate salt of Formula IA. The type and range of excipients screened is outlined in Table 17 below.

TABLE 17

List of excipients used in solid dispersion tablet formulation screening

| Function | % w/w | Excipients |
|---|---|---|
| Disintegrant | 8-13% | Croscarmellose Sodium (Ac-Di-Sol) |
| | | Crospovidone (Polyplasdone XL) |
| Surfactants | 3% | Poloxamer 188 |
| | | Poloxamer 407 |
| Diluents | 19-28% | Mannitol 160C |
| | | Mannitol SD100 |
| | | MCC 101 |
| | | MCC 102 |
| | | Lactose FastFlo316 |
| | | Dextrose |
| | | Sucrose |
| | | Ludiflash |
| | | F-Melt |
| | | Advantose |
| | | GalenIQ |

Formulations were screened using standard USP disintegration apparatus in both water and 0.01 N HCl at 37° C. The percentage of the tablet remaining over time was visually estimated, and results are summarized in Table 18 below.

Tablets made with crospovidone eroded faster and showed faster dissolution rate in 0.01N HCl than those made with Ac-di-sol. Additionally, as shown in the table above, simple sugars such as dextrose and sucrose were observed to increase the erosion rate. The dissolution of the mannitol formulation (F1) and the dextrose formulation (F6) were compared using dissolution testing. FIG. 9 showed results comparing the incorporation of different sugars on dissolution rate.

Example C4

Pharmacokinetic Study in Dog Model

This Example compares the pharmacokinetic effects of administering various solid dispersion formulations to famotidine-pretreated dogs. The formulations screened in famotidine-pretreated dogs are outlined in Table 19 below.

TABLE 18

Composition of formulations used for diluent screening and the disintegration test results

| Component | F1 % w/w | F2 % w/w | F3 % w/w | F4 % w/w | F5 % w/w | F6 % w/w | F7 % w/w | F8 % w/w |
|---|---|---|---|---|---|---|---|---|
| Intragranular | | | | | | | | |
| Compound of Formula I Solid Dispersion, 33.7% w/w | 62.5[a] | 62.5[a] | 62.5[a] | 62.5[a] | 62.5[a] | 62.5[a] | 62.5[a] | 62.5[a] |
| Mannitol | 19.25 | | | | | | | |
| Ludiflash | | 19.25 | | | | | | |
| F-Melt | | | 19.25 | | | | | |
| Advantose | | | | 19.25 | | | | |
| GalenIQ | | | | | 19.25 | | | |
| Dextrose | | | | | | 19.25 | | |
| Sucrose | | | | | | | 19.25 | |
| Lactose FastFlo 316 | | | | | | | | 19.25 |
| Crospovidone XL | 5 | 5 | 5 | 5 | 5 | 5 | 5 | 5 |
| Poloxamer 407 | 3 | 3 | 3 | 3 | 3 | 3 | 3 | 3 |
| Aerosil 200 | 1 | 1 | 1 | 1 | 1 | 1 | 1 | 1 |
| MgS | 0.5 | 0.5 | 0.5 | 0.5 | 0.5 | 0.5 | 0.5 | 0.5 |
| Extragranular | | | | | | | | |
| Crospovidone XL | 5 | 5 | 5 | 5 | 5 | 5 | 5 | 5 |
| MCC 102 | 3 | 3 | 3 | 3 | 3 | 3 | 3 | 3 |
| MgS | 0.75 | 0.75 | 0.75 | 0.75 | 0.75 | 0.75 | 0.75 | 0.75 |
| totals | 100 | 100 | 100 | 100 | 100 | 100 | 100 | 100 |
| % remaining after 10 min in disintegration test | 90 | 100 | 100 | 60 | 60 | 80 | 90 | 100 |
| % remaining after 30 min in disintegration test | 60 | 90 | 90 | 30 | 30 | 30 | 40 | 60 |

[a] Equivalent to 20% of the compound of Formula I free base. Actual compound of Formula I solid dispersion amount was adjusted based on the drug content factor (DCF) with a concomitant adjustment to the amount of diluent.

TABLE 19

Composition of solid dispersion tablet formulations administered to famotidine pre-treated dogs at a dose of 100 mg

| | | Composition (% w/w) | | | |
|---|---|---|---|---|---|
| | Component | Formulation A | Formulation B | Formulation C | Formulation D |
| Intragranular | Bis-mesylate salt of Formula IA:HPMC Solid Dispersion | 62.5[1] | 62.5[1] | — | 62.5[1] |
| | Compound of Formula I: HPMC:TPGS Solid Dispersion | — | — | 62.5[1] | — |
| | Mannitol (Pearlitol 160C) | 19.25 | 19.25 | 22.25 | — |
| | Mannitol (Pearlitol SD 100) | — | — | — | 19.25 |
| | Crospovidone (Polyplasdone XL) | 10.0 | 3.0 | 3.0 | 5.0 |
| | Poloxamer 407 (Lutrol micro 127) | — | 3.0 | — | — |
| | Poloxamer 188 (Lutrol micro 68) | 3.0 | — | — | 3.0 |
| | Colloidal Silicon Dioxide (Aerosil 200) | 1.0 | 1.0 | 1.0 | 1.0 |
| | Magnesium Stearate (Hyqual Code 5712) | 0.5 | 0.5 | 0.5 | 0.5 |
| Extragranular | Crospovidone (Polyplasdone XL) | 3.0 | 10.0 | 10.0 | 5.0 |
| | Microcrystalline Cellulose (Avicel PH 102) | — | — | — | 3.0 |
| | Magnesium Stearate (Hyqual Code 5712) | 0.75 | 0.75 | 0.75 | 0.75 |
| Total | | 100 | 100 | 100 | 100 |

[1]Equivalent to 20% the compound of Formula I free base. Actual bis-mesylate salt of Formula IA solid dispersion amount was adjusted based on DCF with a concomitant adjustment to the amount of mannitol.

The PK data for this study is summarized in Table 20 below.

TABLE 20

Summary of PK data for solid dispersion tablets (e.g., tablets comprising solid dispersion) dosed at 100 mg in famotidine-pretreated dogs (n = 6)

| Dose (mg) | Dog Pretreatment | Formulation | F (%) Mean | AUC$_{0-24}$ (µM · hr) Mean | AUC$_{0-24}$ (µM · hr) SD | Cmax (µM) Mean | Cmax (µM) SD | Tmax (hr) Mean | Tmax (hr) SD |
|---|---|---|---|---|---|---|---|---|---|
| 100 | famotidine | Formulation A | 6.5 | 2.1 | 1.1 | 0.4 | 0.2 | 1.8 | 0.4 |
| 100 | famotidine | Formulation B | 3.1 | 1.0 | 0.5 | 0.2 | 0.05 | 2.1 | 1.0 |
| 100 | famotidine | Formulation C | 7.1 | 2.3 | 1.0 | 0.3 | 0.1 | 3.2 | 0.7 |
| 100 | famotidine | Formulation D | 20 | 6.4 | 7.8 | 0.8 | 0.5 | 1.7 | 0.5 |

As seen in the table above, during initial disintegration screening, it was observed that formulations containing Poloxamer 407 eroded slightly faster than those containing Poloxamer 188. Similarly, increasing the amount of crospovidone in the extragranular portion improved erosion rate. Formulation C was dosed in order to test the effect of incorporating a surfactant (TPGS) in the spray feed solution. Formulation D was prepared using Mannitol SD100 as filler and MCC102 in the extragranular portion to improve process-ability. The PK data presented in the table above shows that Formulation D resulted in the highest bioavailability in famotidine-pretreated dogs of the formulations tested. In addition, Formulation D was observed to have no pH effect.

Results outlined in Table 21 below show that the bioavailability of formulation D in pentagastrin-pretreated dogs was observed to be very similar to that in famotidine-pretreated dogs. Additionally, as seen in FIG. 11, Formulation D was observed to increase exposure in famotidine-pretreated dogs by about 100-fold.

TABLE 21

PK performance in pretreated dogs (n = 6) of Formulation D compared to Formulation Fx

| Dose (mg) | Dog Pretreatment | Formulation | F (%) Mean | AUC$_{0-24}$ (µM · hr) Mean | SD | Cmax (µM) Mean | SD | Tmax (hr) Mean | SD |
|---|---|---|---|---|---|---|---|---|---|
| 100 | pentagastin famotidine | Formulation Fx (Mono-Mesylate Salt of the compound of Formula I, 20% drug load) | 34 0.2 | 11 0.06 | 1.8 0.01 | 1.6 0.02 | 0.2 0.002 | 2.7 1.7 | 1.2 0.6 |
| 100 | pentagastrin famotidine | Formulation D (Bis-mesylate salt of Formula IA, 20% drug load, free base) | 18 20 | 6.1 6.4 | 1.8 7.8 | 1.1 0.8 | 0.1 0.5 | 2.3 1.7 | 0.8 0.5 |

Example C5

Stability Studies

This Example demonstrates the stability of the solid dispersion tablet prepared according to Example C1 above.

Figure 6:
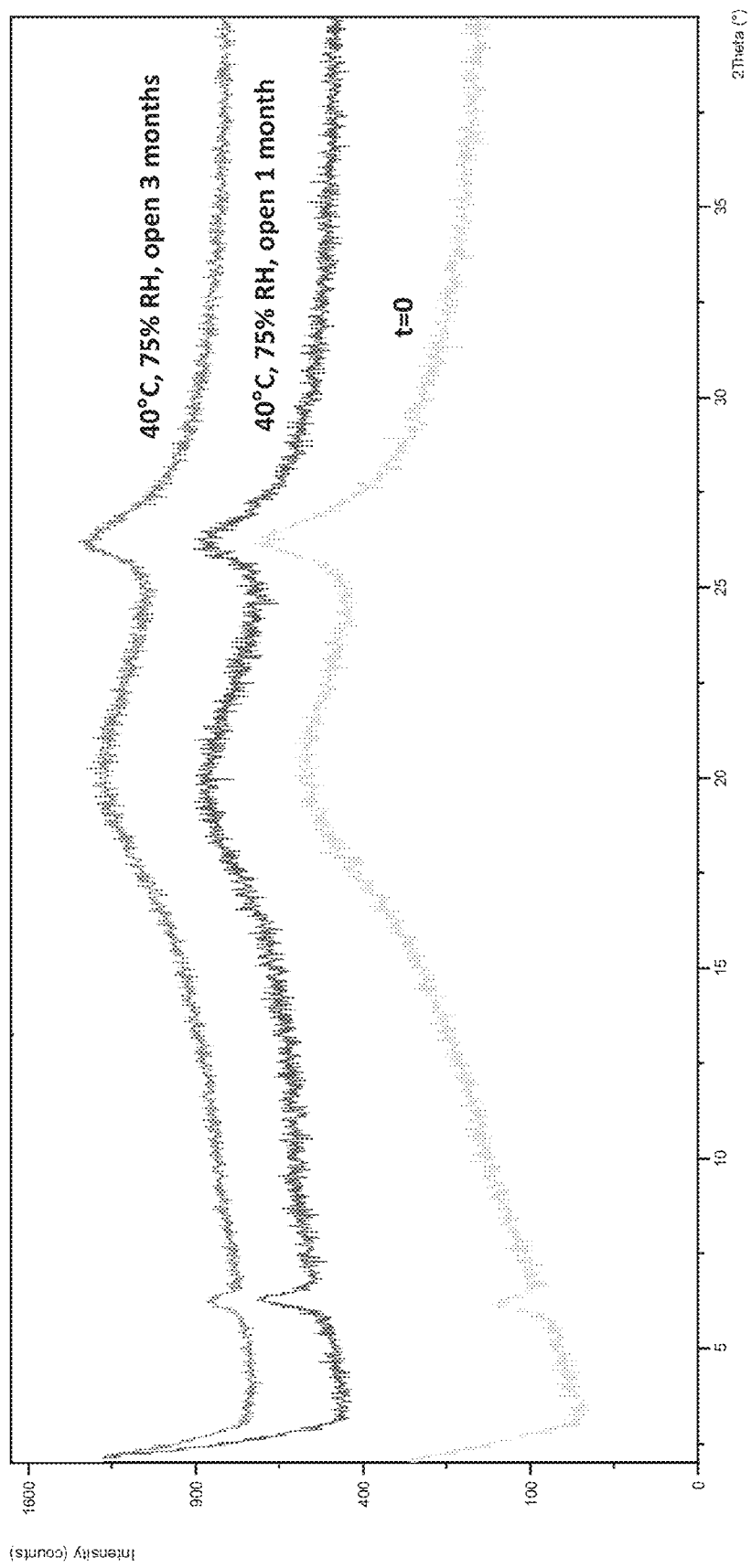
FIG. 6 depicts XRPD patterns of the compound of Formula I: HPMC solid dispersion after open storage at 40° C./75% relative humidity (RH).
Figure 7:
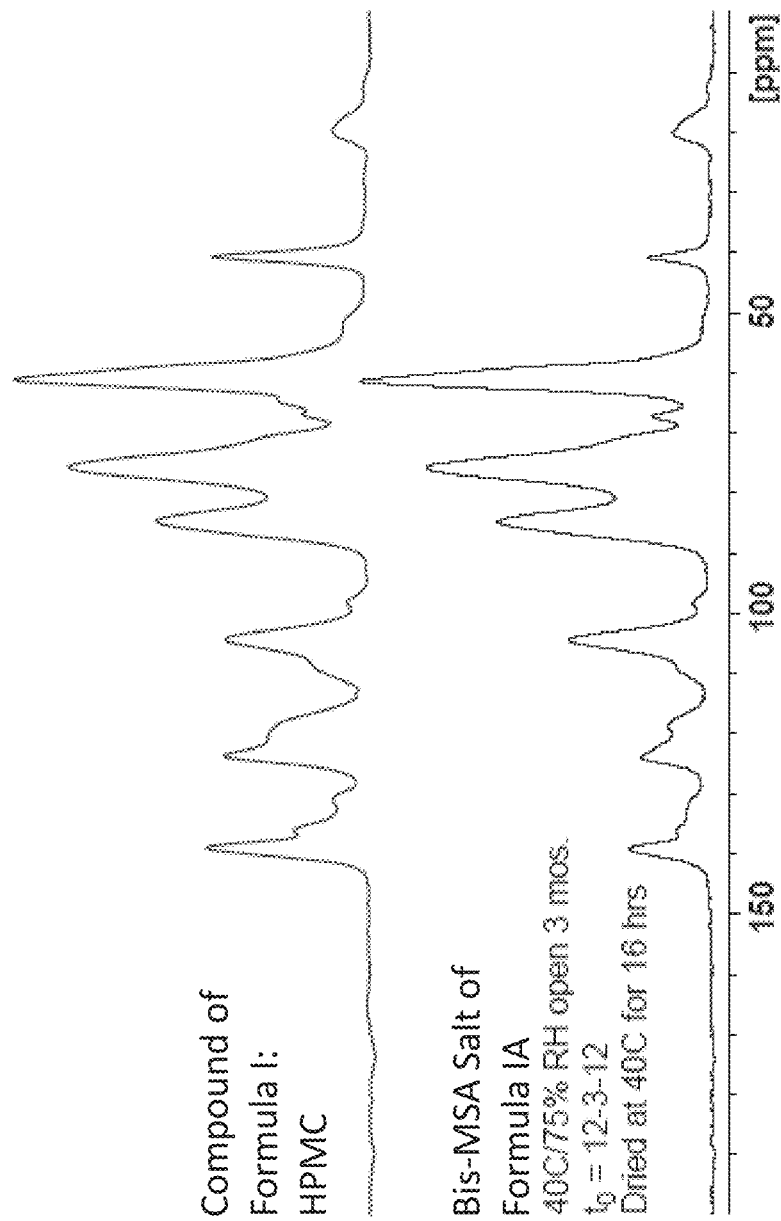
FIG. 7 is a $^{13}C$ SSNMR spectrum of the compound of Formula I: HPMC solid dispersion after open storage at 40° C./75% RH.

The chemical and physical stability of the compound of Formula I: HPMC solid dispersion prepared according to Example C1 was assessed after storage for up to three months at 40° C./75% RH open conditions. Physical stability was monitored using both XRPD and $^{13}$C SSNMR. As shown in FIG. 6, the XRPD pattern did not change over time. Similarly, the $^{13}$C SSNMR spectra, shown in FIG. 7, did not show any evidence of crystallization after three months storage at 40° C./75% RH open conditions. Chemical stability results outlined in Table 22 show that the compound of Formula I:HPMC solid dispersion is chemically stable after 1 month storage at various conditions.

TABLE 22

Chemical stability of the compound of Formula I:HPMC solid dispersion after 1 month storage at various conditions

| Storage Condition | Compound of Formula I (% AN) | Total Imp/Deg (% AN) |
|---|---|---|
| t = 0 | 100.0 | trace |
| 5° C. | 100.0 | trace |
| 25° C./60% RH | 99.9 | trace |
| 40° C./75% RH | 99.9 | trace |
| 60° C. | 99.8 | 0.12 |

For all samples, 5 grams of powder were stored in heat-sealed aluminum pouch with 0.25 g desiccant.
N/D = not detected
trace = <0.05%

Figure 5:
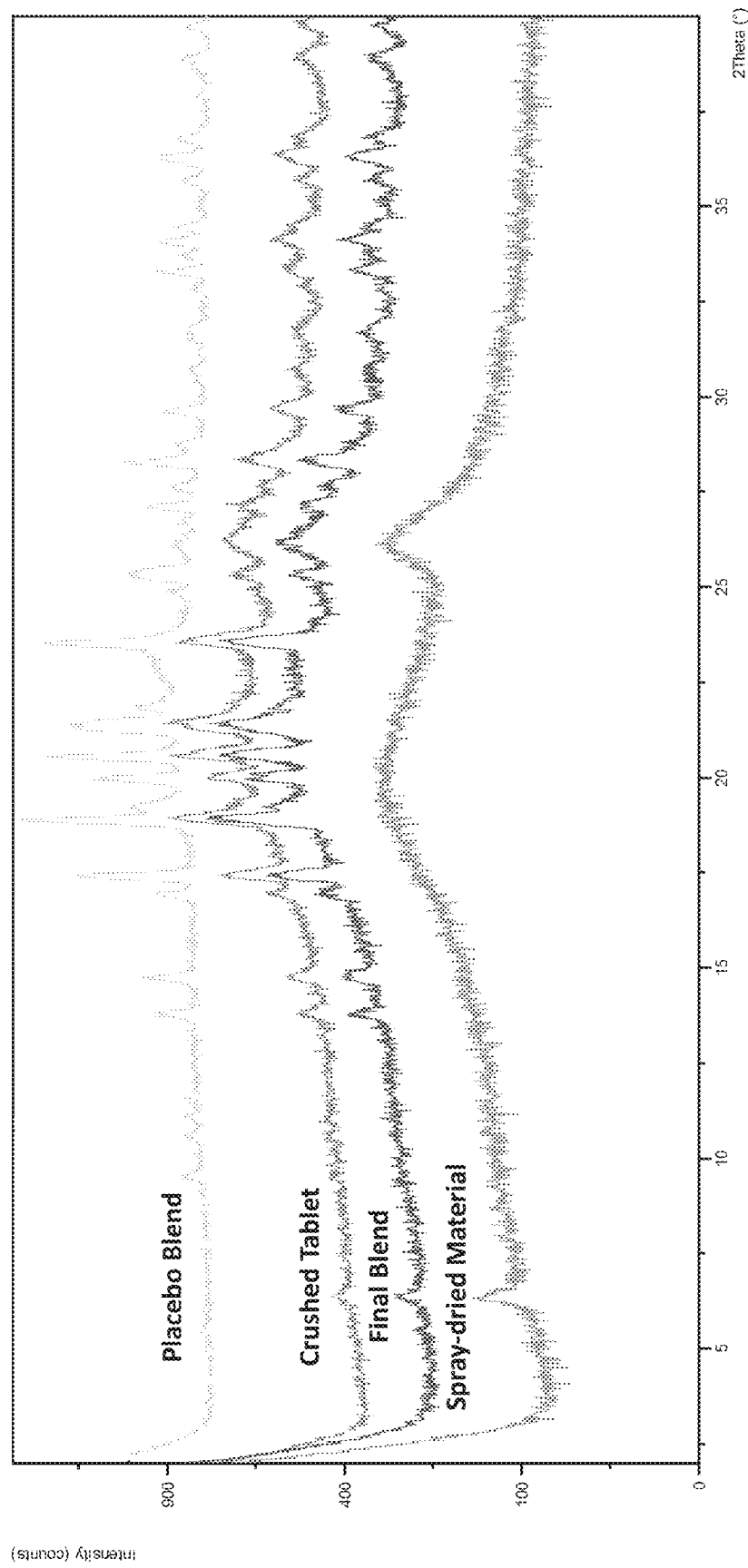
FIG. 5 depicts XRPD patterns of the spray-dried dispersion of the compound of Formula I, and the final blend and tablet of Formulation 2 prepared using the spray-dried dispersion.

The physical stability of the bis-mesylate salt of Formula IA solid dispersion during processing was monitored using XRPD analysis. As shown in FIG. 5, the XRPD pattern of the solid dispersion did not change over the course of tablet manufacturing.

The chemical and physical stability of a development lot of tablets was assessed using HPLC and XRPD. Twenty (20) tablets were packaged in 120-mL HDPE bottles with and without desiccant. Results presented in Table 23 below show that the solid dispersion tablet formulation is stable after 3 months storage at various conditions.

TABLE 23

Development stability data of a bis-mesylate salt of Formula IA solid dispersion tablet, 200 mg (Formulation 2)

| Condition | Timepoint | Strength (%) | Compound of Formula I % AN | Total Deg/Imp (%) | RRT 0.55 | RRT 0.64 | RRT 0.71 | RRT 0.73 | RRT 0.93 | RRT 1.30 | RRT 1.32 |
|---|---|---|---|---|---|---|---|---|---|---|---|
| Initial | t = 0 | 100.5 | 99.9 | 0.1 | — | — | 0.05 | — | — | — | — |
| 5° C., 3 g desiccant | 1 month | 99.1 | 99.7 | 0.3 | trace | — | 0.06 | — | — | 0.14 | — |
|  | 3 months | 100.3 | 100.0 | — | — | — | — | — | — | — | — |
| 25° C./60% RH, 3 g desiccant | 1 month | 100.5 | 99.9 | 0.1 | trace | — | 0.07 | — | — | 0.16 | — |
|  | 3 months | 99.6 | 100.0 | 0.1 | trace | — | — | — | — | — | — |
| 40° C./75% RH, 3 g desiccant | 1 month | 100.5 | 99.7 | 0.3 | 0.07 | — | 0.12 | — | 0.06 | 0.08 | 0.08 |
|  | 3 months | 96.3 | 99.7 | 0.3 | 0.06 | 0.05 | 0.04 | 0.14 | 0.06 | — | — |

TABLE 23-continued

Development stability data of a bis-mesylate salt of Formula IA solid dispersion tablet, 200 mg (Formulation 2)

| Condition | Timepoint | Strength (%) | Compound of Formula I % AN | Total Deg/Imp (%) | RRT 0.55 | RRT 0.64 | RRT 0.71 | RRT 0.73 | RRT 0.93 | RRT 1.30 | RRT 1.32 |
|---|---|---|---|---|---|---|---|---|---|---|---|
| 40° C./75% RH, no desiccant | 1 month | 100.5 | 99.5 | 0.5 | 0.07 | | 0.20 | 0.05 | 0.08 | 0.13 | — | trace: <0.05%
Twenty (20) tablets are packaged in a 120-mL white, high density polyethylene (HDPE) bottle containing zero or three gram silica gel desiccant and polyester coil. Each bottle is capped using a white, continuous thread, child-resistant polypropylene screw cap with an induction sealed, aluminum-faced liner.

Figure 10:
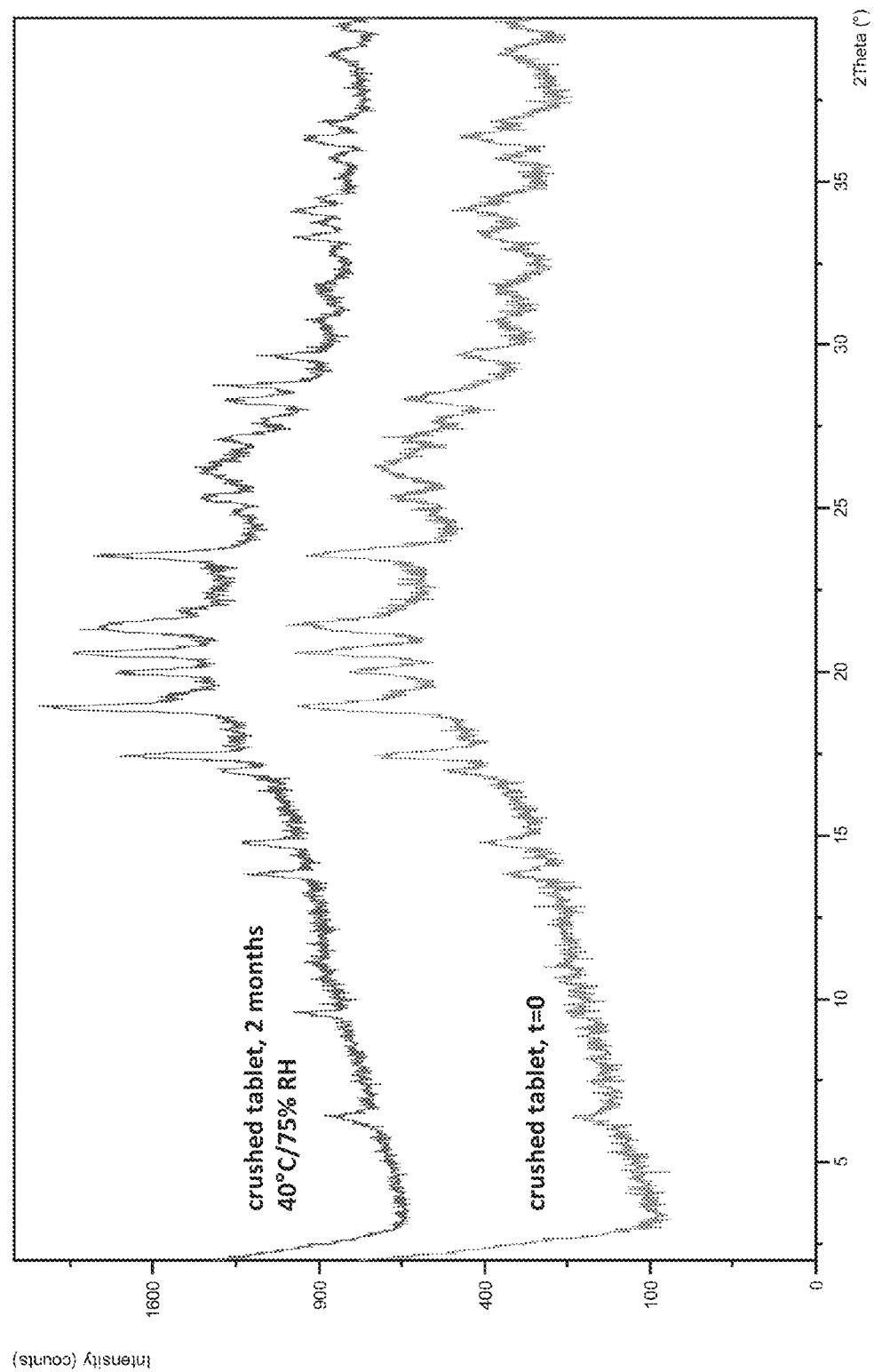
FIG. 10 is an XRPD pattern of a tablet comprising the compound of Formula I incorporated as a solid dispersion after storage at 40° C./75% RH with desiccant.

At 25° C./60% RH, no new degradation products or growth in total impurities was observed. At 40° C./75% RH after 1 month, only 0.1% increase of total impurity was observed in the presence of desiccant while 0.2% increase was observed in the absence of desiccant. After three months storage at 40° C./75% RH with desiccant, the total impurity level did not change. The main degradation products observed at this condition are RRT 0.71 and RRT 0.73. The solid dispersion tablets (e.g., tablets comprising solid dispersion) were also found to be physically stable during storage, as shown in FIG. 10.

Example C6

Spray Drying Manufacturing Process

This Example demonstrates the preparation of a spray-dried dispersion using a spray drying process.

A solid dispersion of a bis-mesylate salt of the compound of Formula I were prepared by combining polymorph Form 3, a monohydrate, bis-mesylate salt of the compound of Formula I with hypromellose 2910, and purified water. Additional methanesulfonic acid (in the quantities specified in Table 24 below) was added to the feed solutions to create solid dispersions with greater than two molar equivalents methanesulfonic acid. The resulting feed solutions were spray dried. The quantitative composition of the feed solution and resulting spray-dried powders is shown in Tables 24-25 below.

TABLE 24

Representative composition of spray drying feed solution and spray-dried powder

| Component | Feed Solution (% w/w) | Spray-Dried Powder (% w/w) |
|---|---|---|
| Formula I (free base, added as monohydrate, bis-mesylate)[a] | 5.0 | 32.4-34.0 |
| Methanesulfonic acid[b] | 2.2-2.9 | 19.0-15.0 |
| HPMC E3[c] | 7.5 | 48.6-51.0 |
| Water | QS | — |
| Total | 100.0 | 100.0 |

[a]Spray drying solution prepared from monohydrate, bis-mesylate salt of the compound of Formula I (Form 3). Equivalent amount of free base present is shown in Table above.
[b]Total methanesulfonic acid present includes methanesulfonic acid and monohydrate, bis-mesylate salt of the compound of Formula I (Form 3) plus any additional methanesulfonic acid added during feed solution preparation.
[c]The ratio of the compound of Formula I as a free base to HPMC E3 is 1:1.5 (w/w).

TABLE 25

Representative composition of spray drying feed solutions

| | Feed Solution Composition (% w/w) | | | |
|---|---|---|---|---|
| Component | 1.9 molar eq. MSA | 2.1 molar eq. MSA | 2.3 molar eq. MSA | 2.5 molar eq. MSA |
| Formula I (free base, added as monohydrate, bis-mesylate)[a] | 5.0 | 5.0 | 5.0 | 5.0 |
| Methanesulfonic acid[b] | 2.3 | 2.5 | 2.7 | 2.9 |
| HPMC E3[c] | 7.5 | 7.5 | 7.5 | 7.5 |
| Water | QS | QS | QS | QS |
| Total | 100.0 | | | |

[a]Spray drying solution prepared from monohydrate, bis-mesylate salt of the compound of Formula I (Form 3). Equivalent amount of free base present is shown in Table above.
[b]Total methanesulfonic acid present includes methanesulfonic acid and monohydrate, bis-mesylate salt of the compound of Formula I (Form 3) plus any additional methanesulfonic acid added during feed solution preparation.
[c]The ratio of the compound of Formula I as a free base to HPMC E3 is 1:1.5 (w/w).

TABLE 26

Representative composition of spray-dried powder

| | Spray-Dried Powder Composition (% w/w) | | | |
|---|---|---|---|---|
| Component | 1.9 molar eq. MSA | 2.1 molar eq. MSA | 2.3 molar eq. MSA | 2.5 molar eq. MSA |
| Formula I (free base, added as monohydrate, bis-mesylate)[a] | 33.9 | 33.4 | 32.9 | 32.4 |
| Methanesulfonic acid[b] | 15.3 | 16.6 | 17.8 | 19.0 |
| HPMC E3[c] | 50.8 | 50.0 | 49.3 | 48.6 |
| Total | 100.0 | | | |

[a]Spray drying solution prepared from monohydrate, bis-mesylate salt of the compound of Formula I (Form 3). Equivalent amount of free base present is shown in Table above.
[b]Total methanesulfonic acid present includes methanesulfonic acid and monohydrate, bis-mesylate salt of the compound of Formula I (Form 3) plus any additional methanesulfonic acid added during feed solution preparation.
[c]The ratio of the compound of Formula I as a free base to HPMC E3 is 1:1.5 (w/w).

Figure 13:
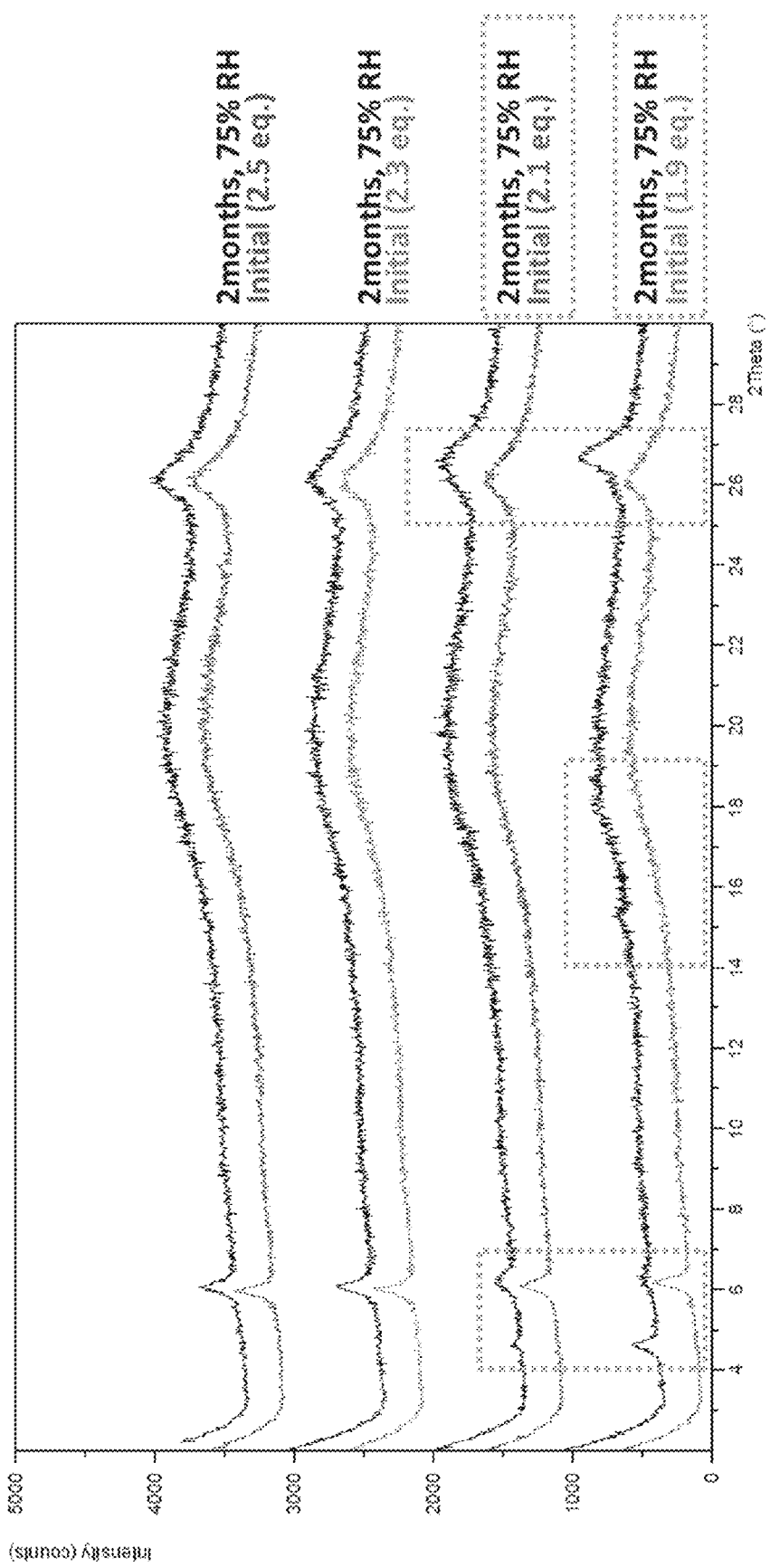
FIG. 13 are XRPD patterns of solid dispersion samples made up of a bis-mesylate salt of a compound of Formula I (as prepared in Example C6) after open storage at room temperature/75% relative humidity (RH).
Figure 14A:
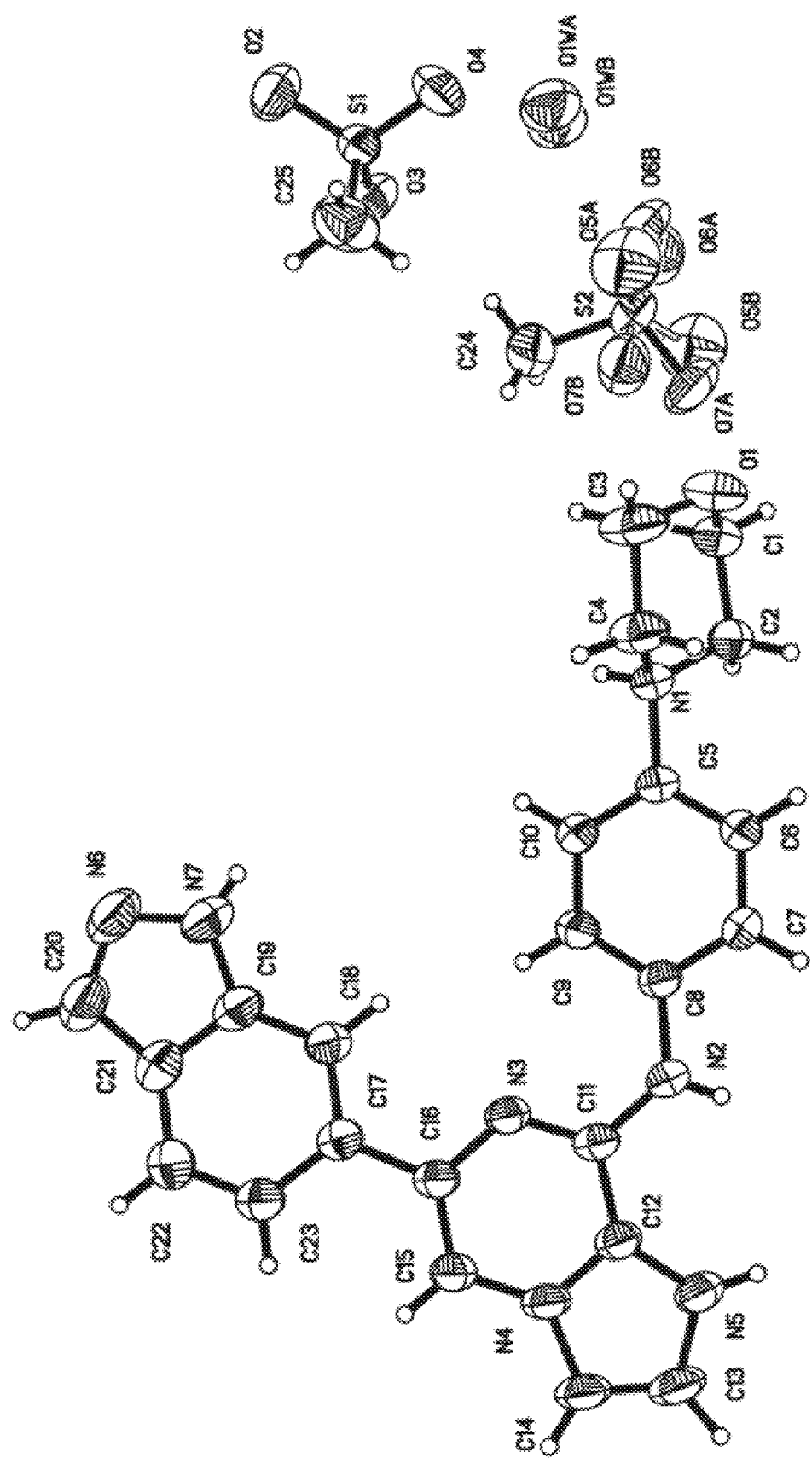
FIG. 14A shows a view of polymorph Form 3 from the crystal structure showing the numbering scheme employed.
Figure 14B:
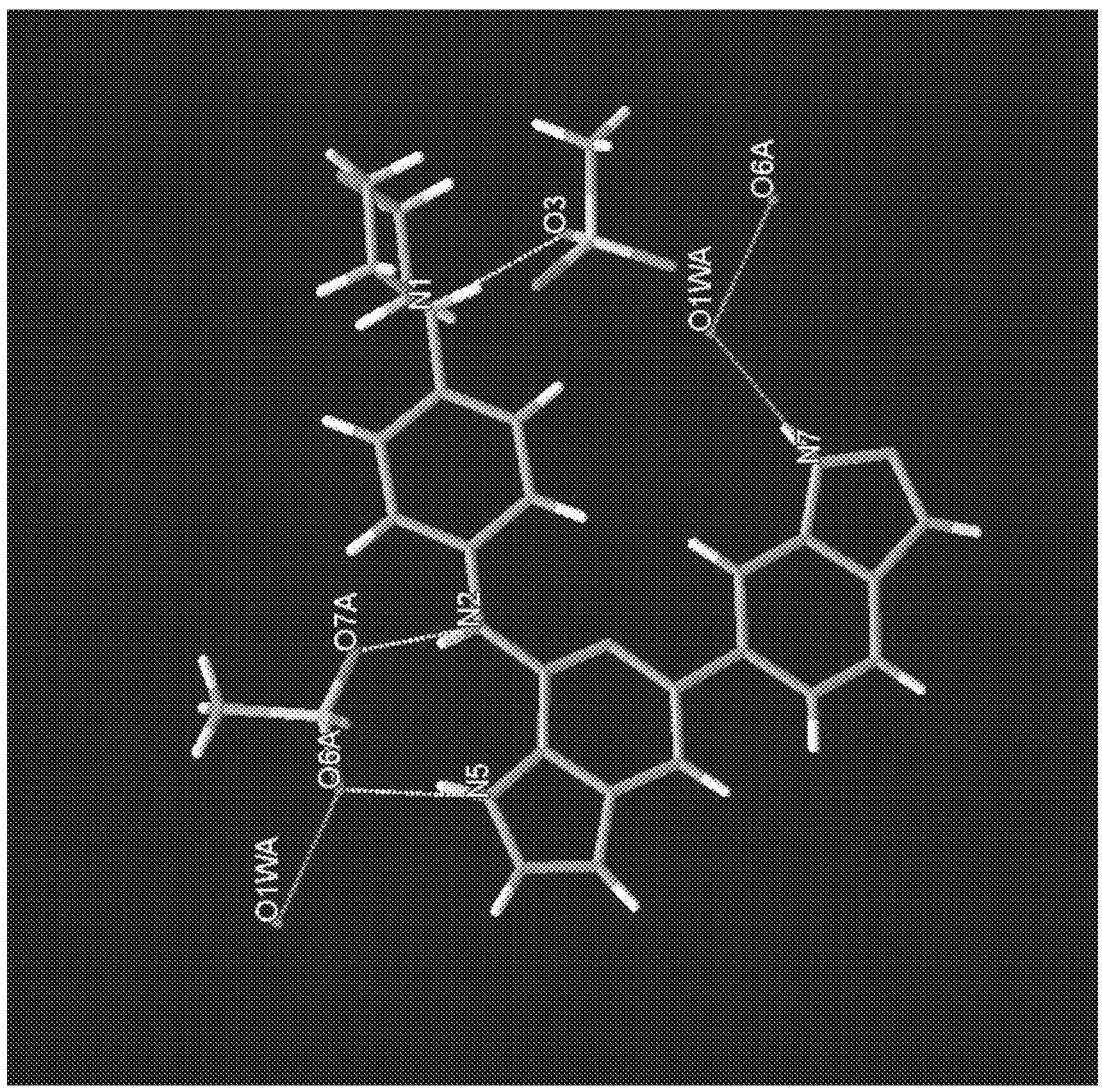
FIG. 14B illustrates the hydrogen bonding interactions of polymorph Form 3.
Figure 14C:
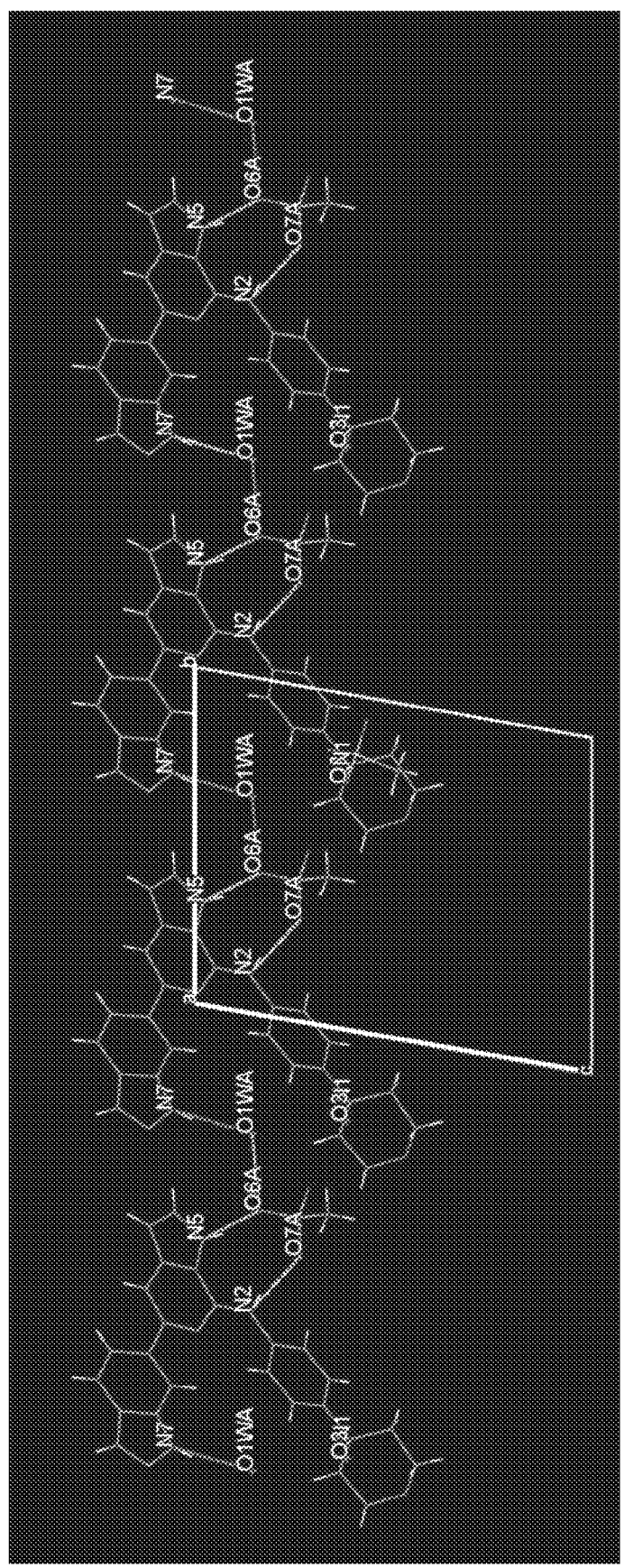
FIG. 14C illustrates the infinite chains of polymorph Form 3, mesylate and water molecules viewed down the crystallographic a axis.
Figure 14D:
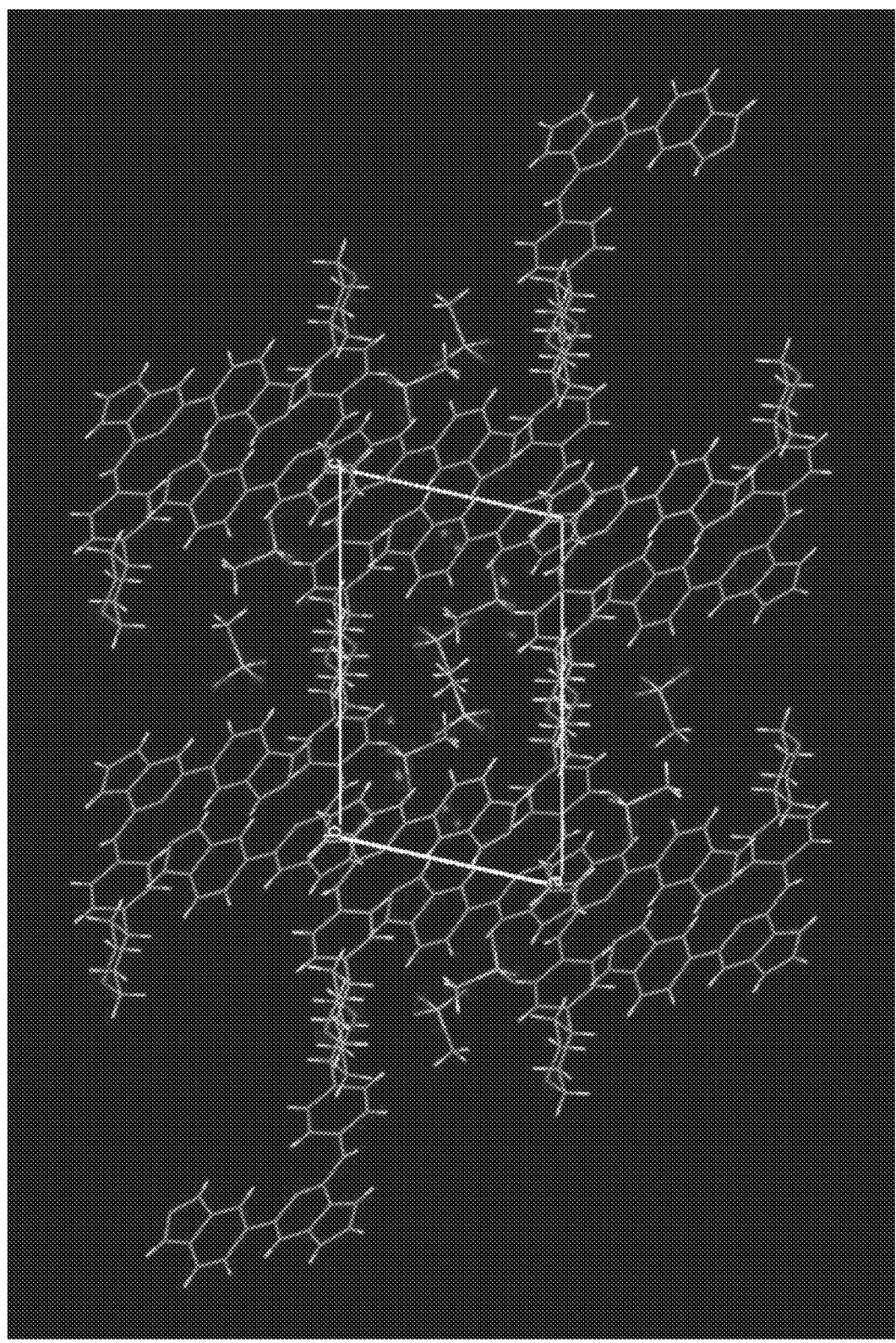
FIG. 14D illustrates the packing of polymorph Form 3 down the crystallographic b axis.

Physical stability of the spray-dried powder was assessed after storage at room temperature/75% RH open condition using X-Ray Powder Diffraction (XRPD). As seen in Table 27 below and FIG. 13, increasing the amount of methanesulfonic acid present was unexpectedly observed to prevent form change.

TABLE 27

Physical stability of bis-mesylate salt of the compound of Formula I solid dispersion samples as a function of methanesulfonic acid content

| Molar Equivalents Methanesulfonic Acid | XRPD Pattern of Samples Stored for 2 months at Room Temperature/75% RH Under Open Conditions |
|---|---|
| 1.9 | Changes observed |
| 2.1 | Changes observed |
| 2.3 | No change observed |
| 2.5 | No change observed |

D. Comparative Studies

Example D1

Effect of Antacids

This Example compares the drug-drug-interaction with antacids, omeprazole and famotidine, in Formulations Fx, 1 and 2 described above.

Each formulation was administered in the dosages indicated in Table 28 below to omeprazole or famotidine pretreated dogs. Pharmacokinetic parameters were measured. As seen in the results summarized in Table 28 below, less effect of acid reduction on exposure was observed with Formulations 1 and 2 compared to Formulation Fx.

TABLE 28

% GLS Means Ratio Exposure, With::Without Acid Reduction (90% CI)

| Parameter | Formulation Fx 900 mg BID + Omeprazole (N = 8) | Formulation 1 800 mg BID + Omeprazole (N = 11) | Formulation 2 800 mg BID + Omeprazole (N = 11) |
|---|---|---|---|
| $AUC_{tau}$ (ng · h/mL) | 9 (4, 20) | 44 (37, 52) | 36 (27, 49) |
| $C_{max}$ (ng/mL) | 7 (3, 16) | 48 (39, 58) | 40 (30, 54) |
| $C_{tau}$ (ng/mL) | 10 (4, 21) | 39 (32, 47) | 33 (23, 47) |

| Parameter | Formulation Fx 100 mg BID + Famotidine (N = 11) | Formulation 1 800 mg BID + Famotidine (N = 11) | Formulation 2 800 mg BID + famotidine (N = 13) |
|---|---|---|---|
| $AUC_{tau}$ (ng · h/mL) | 74 (47, 116) | 58 (48, 70) | 83 (75, 91) |
| $C_{max}$ (ng/mL) | 78 (53, 116) | 59 (48, 73) | 83 (75, 92) |
| $C_{tau}$ (ng/mL) | 70 (38, 128) | 56 (46, 68) | 81 (73, 90) |

Figure 12:
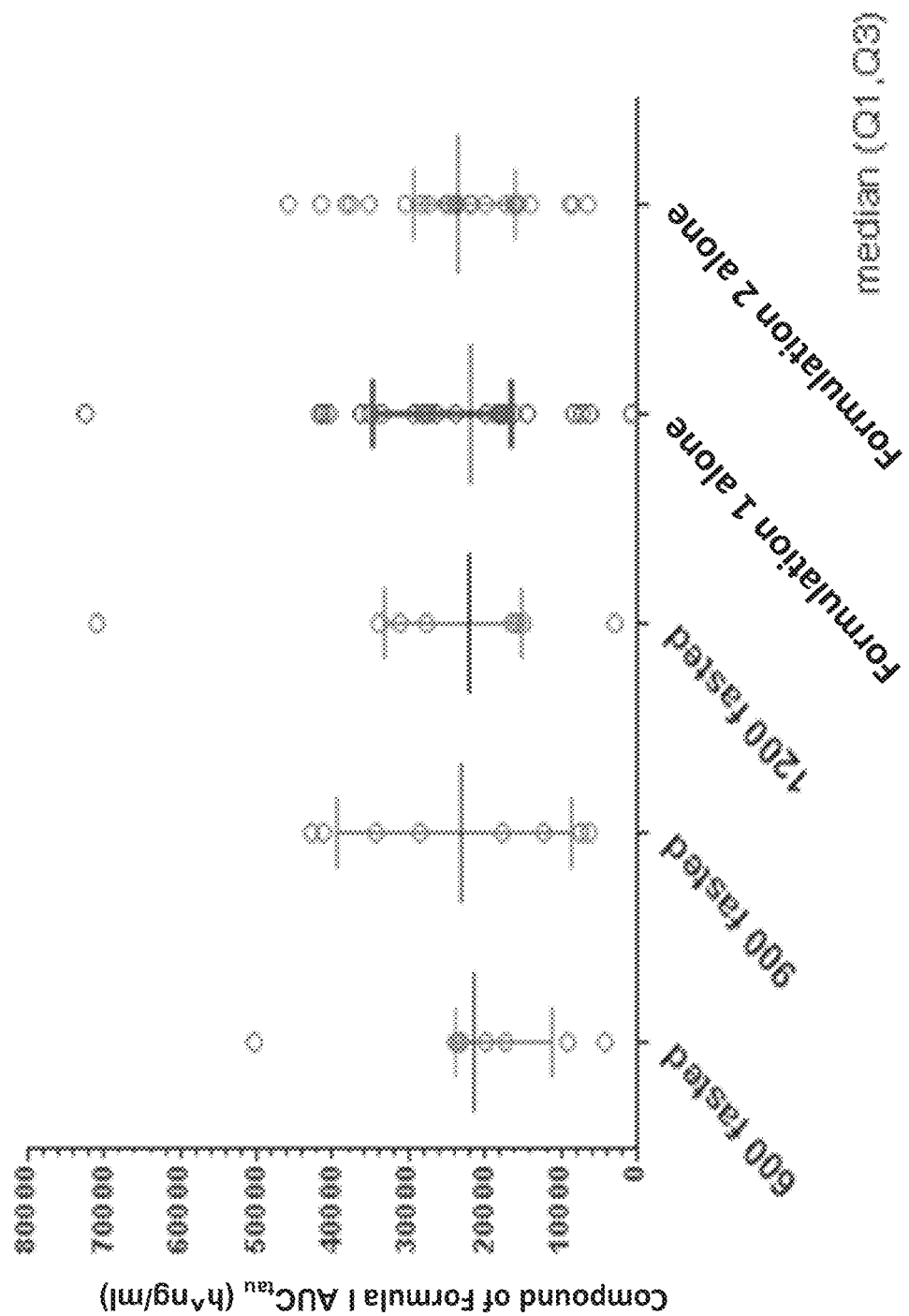
FIG. 12 is a graph comparing pharmacokinetic variability between Formulations Fx, 1 and 2.

Additionally, variability of exposure of the three formulations was determined, and the results were summarized in FIG. 12. As seen in this figure, less variability of exposure with Formulation 2 was observed compared to the other formulations tested.

Example D2

Human Study

Formulation 1 (as described in Example B1) and Formulation 2 (as described in Example C1) were dosed in healthy human volunteers for 6 days at 800 mg b.i.d. On day 7 to 11, in addition to the formulation of a bis-mesylate salt of Formula IA administered, each subject was also dosed with either 20 mg omeprazole q.d. with the am dosing of the compound of Formula I or 40 mg famotidine q.d. with the am dosing of the compound of Formula I. All dosing was performed in fasted condition.

Throughout this specification, various patents, patent applications and other types of publications (e.g., journal articles) are referenced. The disclosure of all patents, patent applications, and publications cited herein are hereby incorporated by reference in their entirety for all purposes.

E. Other Studies

Example E1

Comparison of Intrinsic Dissolution Rates

This example compares the intrinsic dissolution rates of (i) a compound of Formula I (e.g., as a free base) (referred to in this example as Compound 1), (ii) a mono-mesylate salt of a compound of Formula I (referred to in this example as Compound 2), and (iii) polymorph Form 3, which is a polymorph of a monohydrate, bis-mesylate salt of a compound of Formula I (referred to in this example as Compound 3).

Intrinsic dissolution measurements were conducted using a rotating disk apparatus. Disks of Compound 1, Compound 2 and Compound 3 were separately prepared by directly compressing 100 mg of a powder of the respectively compounds in a die at a pressure of 2500 psi for 2 minutes using a hydraulic press (Carver Press, Fred Carver, NJ, USA). The exposed surface area for the resulting disks was 0.5 cm². A USP dissolution apparatus maintained at 37±0.5° C. was used for the dissolution study. Each dissolution vessel contained 500 mL of aqueous dissolution medium of 0.05 N HCl or pH 6.8 20 mM phosphate buffer with 1% cetyltrimetrylammonium bromide (CTAB). The disk holder (die) was half-immersed into the dissolution medium and rotated at 100 rpm. Samples were withdrawn at specified time intervals and the amount of compound dissolved was determined by HPLC.

The amount of compound dissolved at each time point was plotted versus time and the observed dissolution rate (mg/min) was obtained from the slope of the plot. The observed dissolution rate was divided by the surface area of the compound disk (0.5 cm²) to obtain the intrinsic dissolution rate.

The results from this comparative study are summarized in Table 29 below.

TABLE 29

| Physicochemical Properties | Compound 1 | Compound 2 | Compound 3 |
|---|---|---|---|
| Intrinsic dissolution rate in pH 1.3 0.05N HCl with 0.9% NaCl (mg/min/cm²) | 0.00046 | 2.5 | n.d. |
| Intrinsic dissolution rate in pH 6.8 20 mM phosphate with 1% CTAB (mg/min/cm²) | n.d. | 0.003 | 1.2 | n.d. = not determined

What is claimed is:

1. A composition comprising:
(i) a bis-mesylate salt of a compound of Formula I:

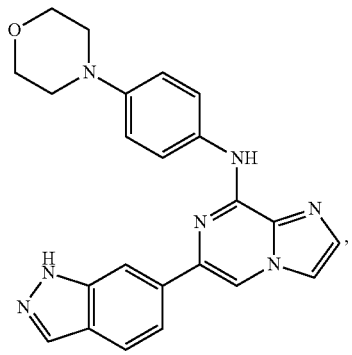

or a hydrate thereof, and
(ii) hydroxypropylmethylcellulose.

2. The composition of claim 1, wherein the bis-mesylate salt is a monohydrate, bis-mesylate salt of the compound of Formula I.

3. The composition of claim 1, wherein the bis-mesylate salt is a polymorph having an X-ray diffraction pattern comprising 2θ-reflections, plus or minus 0.2 degrees 2θ, at 7.7, 12.9, 17.7, and 18.1.

4. The composition of claim 3, wherein the bis-mesylate salt is a polymorph having an X-ray diffraction pattern further comprising 2θ-reflections, plus or minus 0.2 degrees 2θ, at 13.8, 16.9, 22.9 and 26.1.

5. The composition of claim 1, further comprising methanesulfonic acid.

6. The composition of claim 1, wherein the bis-mesylate salt of the compound of Formula I is dispersed within a polymer matrix of the hydroxypropylmethylcellulose.

7. The composition of claim 1, further comprising water.

8. The composition of claim 1, wherein the composition is a feed solution for spray drying.

9. The composition of claim 1, wherein the composition is a spray-dried powder.

10. The composition of claim 9, wherein the powder is non-crystalline.

11. The composition of claim 9, wherein the powder is characterized by an X-ray diffraction pattern comprising 2θ-reflections, plus or minus 0.2 degrees 2θ, at 6.3 and between 26.1 to 26.6.

12. The composition of claim 1, wherein the composition is a tablet.

13. The composition of claim 12, further comprising at least one diluent, binder, disintegrant, surfactant, glidant, or lubricant, or any combinations thereof.

14. The composition of claim 13, wherein one of the at least one diluent is mannitol.

15. The composition of claim 12, further comprising any one or more of crospovidone, poloxamer, colloidal silicon dioxide, magnesium stearate, and microcrystalline cellulose.

16. A composition comprising:
(i) a compound of Formula I:

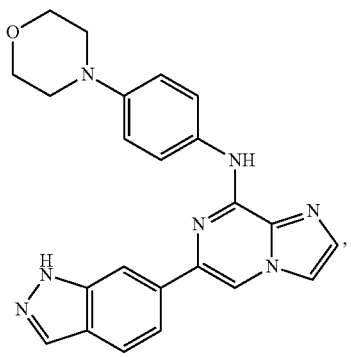

or a cation thereof;
(ii) methanesulfonic acid, or an anion thereof; and
(iii) hydroxypropylmethylcellulose.

17. The composition of claim 16, wherein the methanesulfonic acid, or an anion thereof, and the compound of Formula I, or a cation thereof, are present in the composition in a molar ratio of the methanesulfonic acid, or an anion thereof, to the compound of Formula I, or a cation thereof, of between 2:1 and 3:1.

18. The composition of claim 16, wherein the composition comprises a polymer matrix obtainable from the hydroxypropylmethylcellulose.

19. The composition of claim 18, wherein the compound of Formula I, or a cation thereof, and the methanesulfonic acid, or an anion thereof, are dispersed within the polymer matrix.

20. The composition of claim 16, further comprising water.

21. The composition of claim 16, wherein the composition is a feed solution for spray drying.

22. The composition of claim 16, wherein the composition is a spray-dried powder.

23. The composition of claim 22, wherein the powder is non-crystalline.

24. The composition of claim 23, wherein the powder is characterized by an X-ray diffraction pattern comprising 2θ-reflections, plus or minus 0.2 degrees 2θ, at 6.3 and between 26.1 to 26.6.

25. The composition of claim 16, wherein the composition is a tablet.

26. The composition of claim 25, further comprising at least one diluent, binder, disintegrant, surfactant, glidant, or lubricant, or any combinations thereof.

27. The composition of claim 26, wherein one of the at least one diluent is mannitol.

28. The composition of claim 16, further comprising any one or more of crospovidone, poloxamer, colloidal silicon dioxide, magnesium stearate, and microcrystalline cellulose.

29. A unit dosage form comprising the composition of claim 1.

30. A unit dosage form comprising the composition of claim 16.

31. A composition comprising:
(i) a bis-mesylate salt of a compound of Formula I:

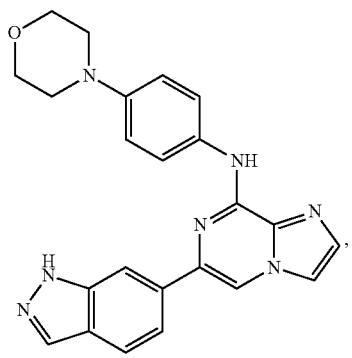

or a hydrate thereof, wherein the bis-mesylate salt is a polymorph having an X-ray diffraction pattern comprising 2θ-reflections, plus or minus 0.2 degrees 2θ, at 7.7, 12.9, 17.7, and 18.1, and
(ii) hydroxypropylmethylcellulose, wherein the a bis-mesylate salt of a compound of Formula I, or a hydrate thereof, is dispersed within a polymer matrix of the hydroxypropylmethylcellulose.

32. The composition of claim 31, further comprising water.

33. The composition of claim 32, wherein the composition is a feed solution for spray drying.

34. The composition of claim 31, wherein the composition is a spray-dried powder.

35. The composition of claim 34, wherein the powder is non-crystalline.

36. The composition of claim 35, wherein the composition is a tablet.

37. The tablet of claim 36, further comprising at least one diluent, binder, disintegrant, surfactant, glidant, or lubricant, or any combination thereof.

38. The composition of claim 37, wherein one of the at least one diluent is mannitol.

39. The composition of claim 38, further comprising at least one component selected from the group of crospovidone, poloxamer, colloidal silicon dioxide, magnesium stearate, and microcrystalline cellulose.

40. The composition of claim 3, wherein the bis-mesylate salt is a polymorph having an X-ray diffraction pattern further comprising 2θ-reflections, plus or minus 0.2 degrees 2θ, at 13.8, 16.9, 22.9 and 26.1.

41. The composition of claim 1, wherein the hydroxypropylmethylcellulose comprises from about 1% w/w to about 50% w/w of the composition.

42. The composition of claim 1, wherein the hydroxypropylmethylcellulose comprises from about 5% w/w to about 25% w/w of the composition.

43. The composition of claim 1, wherein the hydroxypropylmethylcellulose comprises from about 10% w/w to about 20% w/w of the composition.

44. The composition of claim 16, wherein the hydroxypropylmethylcellulose comprises from about 1% w/w to about 50% w/w of the composition.

45. The composition of claim 16, wherein the hydroxypropylmethylcellulose comprises from about 5% w/w to about 25% w/w of the composition.

46. The composition of claim 16, wherein the hydroxypropylmethylcellulose comprises from about 10% w/w to about 20% w/w of the composition.

47. The composition of claim 31, wherein the hydroxypropylmethylcellulose comprises from about 1% w/w to about 50% w/w of the composition.

48. The composition of claim 31, wherein the hydroxypropylmethylcellulose comprises from about 5% w/w to about 25% w/w of the composition.

49. The composition of claim 31, wherein the hydroxypropylmethylcellulose comprises from about 10% w/w to about 20% w/w of the composition.

50. The composition of claim 31 wherein the bis-mesylate salt of the compound of Formula I, or a hydrate thereof, comprises from about 30% w/w to about 45% w/w of the composition, and hydroxypropylmethylcellulose comprises from about 10% w/w to about 30% w/w of the composition.

51. The composition of claim 50 further comprising mannitol from about 20% w/w to about 30% w/w of the composition.

52. The composition of claim 50 further comprising poloxamer from about 1% w/w to about 5% w/w of the composition.

53. The composition of claim 50 further comprising colloidal silicon dioxide from about 1% w/w to about 2% w/w of the composition.

54. The composition of claim 50 further comprising microcrystalline cellulose from about 1% w/w to about 5% w/w of the composition.

55. The composition of claim 50 further comprising magnesium stearate from about 0.5% w/w to about 2% w/w of the composition.

56. The composition of claim 50 further comprising crospovidone from about 5% w/w to about 15% w/w of the composition.

57. The composition of claim 31, wherein:
a) the bis-mesylate salt of a compound of Formula I, or a hydrate thereof, comprises from about 30% w/w to about 45% w/w of the composition;
b) hydroxypropylmethylcellulose comprises from about 10% w/w to about 30% w/w of the composition;
c) mannitol comprises from about 20% w/w to about 30% w/w of the composition;
d) crospovidone comprises from about 5% w/w to about 15% w/w of the composition;
e) colloidal silicon dioxide comprises from about 1% w/w to about 2% w/w of the composition; and
f) microcrystalline cellulose comprises from about 1% w/w to about 5% w/w of the composition.

* * * * *